United States Patent
Gallego-Perez et al.

(10) Patent No.: US 12,415,058 B2
(45) Date of Patent: Sep. 16, 2025

(54) INTERPENETRATING MICROSTRUCTURES FOR NANOCHANNEL-BASED SAMPLING AND/OR CARGO DELIVERY

(71) Applicant: Ohio State Innovation Foundation, Columbus, OH (US)

(72) Inventors: Daniel Gallego-Perez, Columbus, OH (US); Natalia Higuita-Castro, Columbus, OH (US); Lingqian Chang, Evanston, IL (US); Chandan Sen, Upper Arlington, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 914 days.

(21) Appl. No.: 17/548,011

(22) Filed: Jan. 18, 2022

(65) Prior Publication Data
US 2022/0134073 A1    May 5, 2022

Related U.S. Application Data

(63) Continuation-in-part of application No. 16/471,907, filed as application No. PCT/US2017/067630 on Dec. 20, 2017, now Pat. No. 11,235,132.
(Continued)

(51) Int. Cl.
*A61M 37/00* (2006.01)
*A61B 10/00* (2006.01)
*G03F 7/00* (2006.01)

(52) U.S. Cl.
CPC ..... *A61M 37/0015* (2013.01); *A61B 10/0045* (2013.01); *G03F 7/0035* (2013.01);
(Continued)

(58) Field of Classification Search
CPC ...... A61M 37/0015; A61M 2037/0023; A61M 2037/003; A61M 2037/0038;
(Continued)

(56) References Cited

U.S. PATENT DOCUMENTS 6,312,612 B1    11/2001    Sherman et al.
6,623,457 B1    9/2003    Rosenberg
(Continued)

FOREIGN PATENT DOCUMENTS

JP    2010/505518    2/2010
WO    2004076339 A2    9/2004
(Continued)

OTHER PUBLICATIONS

Notice of Preliminary Rejection issued Aug. 26, 2022, by Korean Patent Office, Korean Patent Application No. 10-2019-7021274.
(Continued)

*Primary Examiner* — Eric F Winakur
*Assistant Examiner* — Hy Khanh Doan
(74) *Attorney, Agent, or Firm* — Thomas | Horstemeyer, LLP

(57) ABSTRACT

Provided herein are devices and methods for topically and controllably delivering cargo or collecting samples into or from biological tissues, particularly the skin. These devices permit delivery of cargo and collection of samples from cell layers deep within a tissue. These devices include microstructure arrays comprising nanochannels. Also disclosed is a device comprising a one or more microstructure arrays encased in a frame.

21 Claims, 53 Drawing Sheets

Specification includes a Sequence Listing.

Related U.S. Application Data

(60) Provisional application No. 62/438,256, filed on Dec. 22, 2016.

(52) U.S. Cl.
CPC .............. *A61B 2010/008* (2013.01); *A61M 2037/0023* (2013.01); *A61M 2037/003* (2013.01); *A61M 2037/0038* (2013.01); *A61M 2037/0053* (2013.01); *A61M 2037/0061* (2013.01)

(58) Field of Classification Search
CPC .. A61M 2037/0053; A61M 2037/0061; A61B 10/0045; A61B 2010/008; G03F 7/0035; B33Y 80/00
See application file for complete search history.

(56) References Cited

U.S. PATENT DOCUMENTS

| | | | |
|---|---|---|---|
| 7,344,499 B1* | 3/2008 | Prausnitz | A61B 5/150022 600/347 |
| 2002/0133129 A1 | 9/2002 | Arias et al. | |
| 2003/0045837 A1 | 3/2003 | Delmore et al. | |
| 2004/0019331 A1 | 1/2004 | Yeshurun | |
| 2004/0164454 A1 | 8/2004 | Gartstein et al. | |
| 2007/0275521 A1 | 11/2007 | Fu | |
| 2012/0058506 A1 | 3/2012 | Gao et al. | |
| 2013/0165861 A1 | 6/2013 | Ross | |
| 2014/0148870 A1 | 5/2014 | Burnett | |
| 2016/0106965 A1 | 4/2016 | Baker et al. | |

FOREIGN PATENT DOCUMENTS

| | | |
|---|---|---|
| WO | 2004/021273 A2 | 1/2005 |
| WO | 2008042404 A2 | 4/2008 |

OTHER PUBLICATIONS

Office Action issued by the Japanese Patent Office for application 2019-534295, dated Jul. 6, 2021.
International Search Report for Application PCT/US2017/067630, mailed Apr. 6, 2018.
International Search Report and Written Option issued by the European Patent Office for EP 17885274, mailed Oct. 5, 2020.
Office Action issued by the Brazilian Patent Office for application BR112019012924-3, dated May 5, 2021.

* cited by examiner

Nanochanneled substrate

Selective surface etching to define interpenetrating micro structures

- TNT method
- Direct cargo delivery to the outermost cell layer only

- DTN method

- Direct cargo delivery at multiple levels

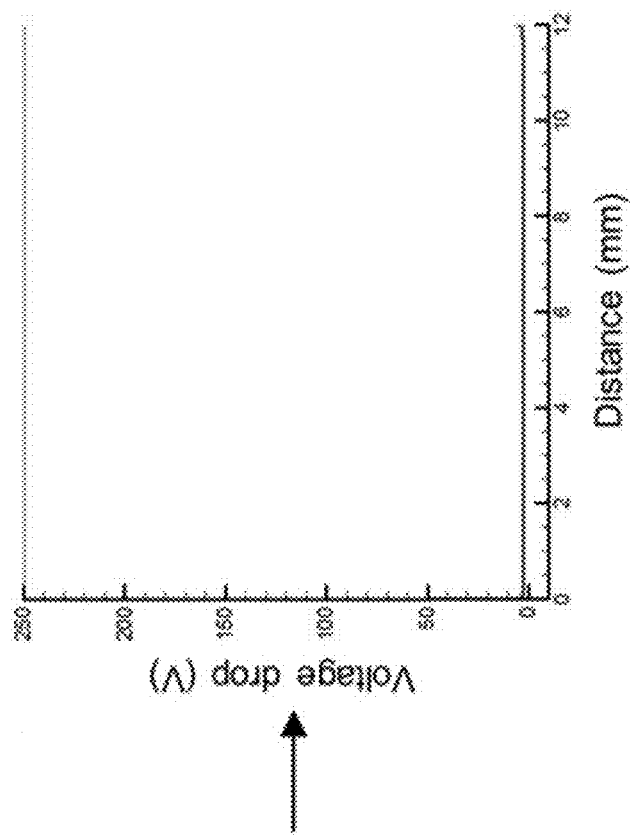
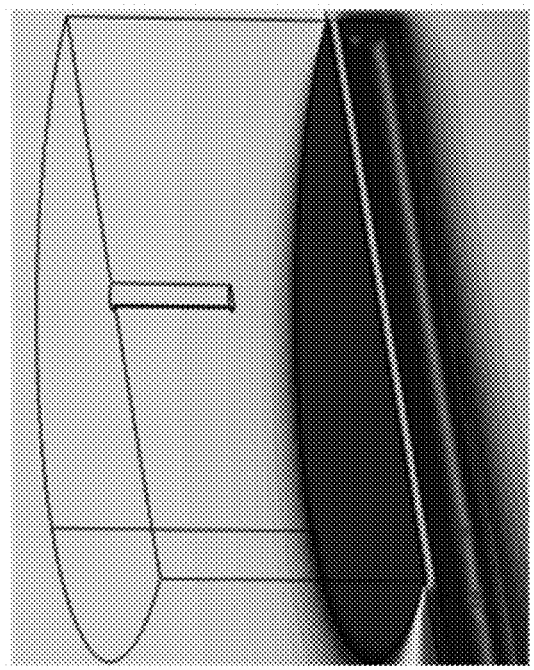
FIGURE 8B
FIGURE 8C a) pyramidal
b) conical
c) dwarf conical

SEQUENCE LISTING

<160> NUMBER OF SEQ ID NOS: 29

<210> SEQ ID NO 1
<211> LENGTH: 21
<212> TYPE: DNA
<213> ORGANISM: Artificial Sequence
<220> FEATURE:
<223> OTHER INFORMATION: Synthetic Construct

<400> SEQUENCE: 1
ctctgctgcc tcctggcttc t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
cgaggcggat cacaagcaat a                                              21

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
tcaatgggcg ggggtcgtt                                                 19

<210> SEQ ID NO 4
<211> LENGTH: 23
<212> TYPE: DNA
<213> ORGANISM: Artificial Sequence
<220> FEATURE:
<223> OTHER INFORMATION: Synthetic Construct

<400> SEQUENCE: 4
gcggtctggc agtaaaaact atc                                            23

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
gtgaaacagc attgctgtca ctt                                            23

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
cgacgaggga tcctacgac                                                 19

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
cttcctctgc cctcgaac                                                 18

<210> SEQ ID NO 8
<211> LENGTH: 22
<212> TYPE: DNA
<213> ORGANISM: Artificial Sequence
<220> FEATURE:
<223> OTHER INFORMATION: Synthetic Construct

<400> SEQUENCE: 8
ggtggagttc aagtccatct ac                                            22

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tggcgtccac gtagtagtag                                               20

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct

<400> SEQUENCE: 10
atacaagagc tgttcagctg tc                                            22

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gtcgtgcata tttgccactg                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
ggaccagtcc ccgaagcagc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
agtggagcag ctggcctgga                                               20

```
<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
agcgctgtga acgcttgcct                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
catgagaggc cctcccggct                                                    20

<210> SEQ ID NO 16
<211> LENGTH: 17
<212> TYPE: DNA
<213> ORGANISM: Artificial Sequence
<220> FEATURE:
<223> OTHER INFORMATION: Synthetic Construct

<400> SEQUENCE: 16
ccgtccagct cgaccag                                                       17

<210> SEQ ID NO 17
<211> LENGTH: 18
<212> TYPE: DNA
<213> ORGANISM: Artificial Sequence
<220> FEATURE:
<223> OTHER INFORMATION: Synthetic Construct

<400> SEQUENCE: 17
gatcacatgg tcctgctg                                                      18

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
gtgcaacgag cagggcgagt                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
ggagccaccg cgcacagaat                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 20
gctggtgcag agcggcaaga                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
agacggcggt aggtggcgat                                                   20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
tacacgggcg agggcatgga                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
tcacttgggc ccctgggctt                                                   20

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
gtgtgatggg attccctgga ccta                                              24

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
cctgagctcc agcttctcca tctt                                              24

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
aggccaggtg gtggacgtgt                                                   20

<210> SEQ ID NO 27
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
cacgctggac ctgcttgggg                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
gtgcagtgcc agcctcgtcc                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
gcaccggcct caccccattt                                          20
```

INTERPENETRATING MICROSTRUCTURES FOR NANOCHANNEL-BASED SAMPLING AND/OR CARGO DELIVERY

CROSS-REFERENCE TO RELATED APPLICATIONS

This application is a continuation-in-part of copending application Ser. No. 16/471,907, filed Jun. 20, 2019, which is a National Stage of International Application No. PCT/US2017/067630, filed Dec. 20, 2017, which claims benefit of U.S. Provisional Application No. 62/438,256, filed Dec. 22, 2016, which is hereby incorporated herein by reference in its entirety.

BACKGROUND

A common technique for delivering therapeutic agents across or into a biological tissue is the use of nanochannel arrays. However, current nanochannel-based delivery methods can only directly deliver cargo to the outermost cell layer of a tissue, significantly limiting the action range of this technology. Thus, there is a need for nanochannel-based delivery methods that can deliver cargo and/or sample substances from cells from cell layers deep within a tissue.

SUMMARY

Provided herein are devices and methods for topically and controllably delivering cargo and/or collecting samples into or out of biological tissues, particularly the skin. These devices permit delivery of cargo to deeper cell layers of a tissue. These devices include microstructure arrays comprising nanochannels. Also disclosed is a device comprising a one or more microstructure arrays encased in a frame. In some embodiments, the substance is an extracellular material, such as interstitial fluid or an intracellular material.

In some embodiments, the microstructure array includes a planar substrate with a top surface and a bottom surface, a reservoir in fluid communication with the top surface of the planar substrate, and a plurality of microstructures projecting from the bottom surface of the planar substrate. Each of the plurality of microstructures comprises a solid body portion tapering from a base to a distal tip positioned at a height from the bottom of the planar substrate, thereby defining a microstructure surface. Each of the plurality of microstructures also comprises a first delivery/sampling channel extending from the top surface of the planar substrate to a first channel opening within the microstructure surface, thereby fluidly connecting the reservoir to the first channel opening. Each of the plurality of microstructures also comprises a second delivery/sampling channel extending from the top surface of the planar substrate to a second channel opening within the microstructure surface, thereby fluidly connecting the reservoir to the second channel opening.

In some embodiments, the first channel opening is positioned within a first plane parallel to the planar surface and the second channel opening is positioned within a second plane parallel to the planar substrate. In these embodiments, the first plane is distally spaced apart from the second plane. In some of these embodiments, the first plane is distally spaced apart from the second plane by a distance of from 20% to 60% of the height between the distal tip and the bottom of the planar substrate. In other embodiments, the first channel opening is positioned at the distal tip.

In some embodiments, each of the plurality of microstructures further comprises a third delivery/sampling channel extending from the top surface of the planar substrate to a third channel opening within the microstructure surface, thereby fluidly connecting the reservoir to the third channel opening. In some of these embodiments, the first channel opening is positioned at a first plane parallel to the planar substrate, the second channel opening is positioned within a second plane parallel to the planar substrate, the third channel opening is positioned within a third plane parallel to the planar substrate. In these embodiments the first plane is distally spaced apart from the second plane and the second plane is distally spaced apart from the third plane. In some of these embodiments, the first plane is distally spaced apart from the second plane by a distance of from 20% to 60% of the height between the distal tip and the bottom of the planar substrate, and the second plane is distally spaced apart from the third plane by a distance of from 20% to 60% of the height between the distal tip and the bottom of the planar substrate.

In some embodiments the height between the distal tip and the bottom of the planar substrate is from 20 microns to 1000 microns.

In some embodiments the base has a substantially circular shape. In other embodiments the base has a substantially rectangular shape.

In some embodiments the solid body portion is formed from silicon or a silicon-based material, e.g. silicon nitride. In other embodiments the planar substrate is formed from silicon or a silicon-based material. In other embodiments the solid body portion is formed from anodized aluminum oxide. In other embodiments the planar substrate is formed from anodized aluminum oxide.

In some embodiments, the planar substrate further comprises a plurality of delivery channels, each of which extends from the top surface of the planar substrate to a channel opening within the bottom surface of the planar substrate, thereby fluidly connecting the reservoir to the channel opening within the bottom surface of the planar substrate.

Also disclosed is a device comprising a one or more microstructure arrays encased in a frame. In some embodiments, the frame is pliable and/or malleable. In some cases, this allows for application to a curved surface. In some cases, the frame is non-planar. For example, the frame can be a cylinder such that the microstructure arrays are circumferentially arranged around the cylinder. In some cases, a microstructure array is positioned at the distal end of the cylinder. In some of these embodiments, the cylinder defines a lumen, which can function as a reservoir for the microstructure arrays. In these embodiments, an electrode can also be positioned in the lumen.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6a shows a schematic diagram of the TNT process on exfoliated skin tissue. The positive electrode is inserted intradermally, while the negative electrode is put in contact with the cargo solution, A pulsed electric field (250 V, 10 ms pulses, 10 pulses) is then applied across the electrodes to nanoporate exposed cell membranes and inject the cargo directly into the cytosol. Scanning electron micrographs (top) of the TNT platform surface showing the nanopore array. FIG. 6n shows neurofilament (week 8) expression in the skin after ABM TNT treatment. N=3 animals (biological replicates). *p<0.05 (Holm-Sidak method), #0.05<p<0.08 (one-tailed t-test).

FIG. 7a shows double side polished silicon wafer. FIGS. 7b-d show nanochannel patterning and DRIE. FIG. 7e shows scanning electron microscopy (SEM) image of the etched nanochannels. FIG. 7f shows back-side etching of microreservoirs. FIG. 7g shows SEM micrographs and FIGS. 7h and 7i show plots showing etching profiles and etch rates, respectively, under different conditions. FIGS. 7j and 7k show simulation results showing field distribution (j1, k1) and heat dissipation profiles 0, k 2-3) for asymmetric (i.e., T-shape) nanochannel arrays vs. symmetric (i.e., cross-shaped) arrays. Bulk electroporation (BEP) is the current gold standard for non-viral gene delivery in vivo. Gene uptake in BEP, however, is a highly stochastic process, which is not only influenced by non-uniform electric fields, but also downstream and/or more passive processes such as endocytosis and diffusion, respectively (Geng, T. & Lu, C. Lab Chip 13, 3803-3821 (2013). Boukany, P. E. et al. Nat Nanotechnol 6, 747-754 (2011); Gallego-Perez, D. et al. Nanomedicine (2015)). As such, simple approaches that facilitate more active and deterministic gene delivery in vivo are clearly needed. Here cleanroom-based technologies were implemented (i.e., projection lithography, contact photolithography, and deep reactive ion etching—DRIE—) (FIGS. 7a-i)) to fabricate silicon-based TNT devices for active non-viral gene delivery to naturally—(e.g., skin) or surgically-accessible (e.g., skeletal muscle) tissue surfaces in a more deterministic manner. The TNT platforms consisted of a massively-parallel array of clustered nanochannels interconnected to microscale reservoirs that could hold the genetic cargo to be transduced into the tissues. Briefly, arrays of ~400-500 nm channels were first defined on the surface of a ~200 μm thick double-side polished silicon wafer using projection lithography and DRIE. Simulation studies suggest that such asymmetric T-shape array provides some inherent advantages in terms of electric field distribution and heat dissipation compared to a more symmetric nanopore distribution, with asymmetric clusters of nanochannels exhibiting less inactive zones (FIG. 7j1, k1, stars), while at the same time reducing by 20-25% the peak and valley temperatures (FIGS. 7j2-3, k2-3). This was then followed by contact lithography-based patterning and DRIE-mediated drilling of an array of microreservoirs juxtaposing the nanochannels. Finally, the platform surface was passivated with a thin insulating layer of silicon nitride.

FIGS. 8a-h show simulation results of in vivo nanochannel-based electroporation vs. bulk electroporation (BEP). FIG. 8a shows a schematic diagram illustrating the experimental set-up. FIGS. 8b and 8c show simulated voltage distribution under a 250 V stimulation. FIGS. 8d-f show a simulation of transmembrane potential for single-cell bulk electroporation. FIG. 8g shows a poration profile for a cell in direct contact with the nanochannel (cell 1) compared to cells far away from the nanochannels (cell 2 and cell 3). FIG. 8h shows profiles in TNT vs. BEP.

FIG. 9a shows a schematic diagram illustrating the experimental set-up. MCAO stroke is first induced. This is then followed by ABM TNT treatment and EV isolation from dorsal skin prior to intracranial injection of EVs. FIGS. 9b and 9c show MRI imaging and quantification showing a significant reduction in the infarcted volume only 7 days after EV injection. FIG. 9d shows immunofluorescence imaging 21 days after stroke induction showing DCX+ cells/processes projecting from the Subventricular (SVZ) zone towards the infarcted area (white arrows). DCX+ cells in control brains were found mostly lining the walls of the SVZ zone. *p<0.05 (Holm-Sidak method).

FIG. 10b shows Col1A1-GFP mouse models showing skin cells of either K14 or Col1A1 origin (green/GFP) also expressing the Tuj1 neuronal marker. (FIG. 10a.1, FIG. 10b.1) Cellular elements that were immunoreactive for both the GFP tracer and Tuj1 were further analyzed by LCM/qRT-PCR. The results indicate that such double-positive elements had significantly high neuronal marker gene expression and moderate to markedly reduced skin cell marker gene expression. *$p<0.05$ (Holm-Sidak method). Lineage tracing experiments with a K14-Cre reporter mouse model, where Keratin 14 positive (K14+) cells undergo cre-mediated recombination of the ROSA locus ultimately switching from tdTomato expression to eGFP, confirmed that the newly-induced neurons partly originated from K14+ skin cells. Experiments with a Col1A1-eGFP mouse model, where cells with an active Col1A1 promoter express eGFP, showed a number of Collagen/eGFP+ cells from the dermis in a transition phase to Tuj1+. LCM was used to capture and further characterize the gene expression profile of cellular elements from the transgenic mouse model sections that were both GFP+ and Tuj1+, which would correspond to cells that were of K14 origin but now express a neuronal marker, or cells that have an active collagen promoter (e.g., fibroblasts) transitioning to a neuronal fate. The results indicated that such elements indeed exhibited increased expression of pro-neuronal markers, and reduced expression of the cell-of-origin marker (i.e., K14, Col1A1).

FIG. 14A shows an embodiment with conical microneedles. FIG. 14B shows an embodiment with pyramidal microneedles. FIG. 14C shows an embodiment with concentrically-arranged cylinders. FIG. 14D shows an embodiment with ridges.

FIG. 24A is a silicon wafer patterned via lithography and deep reactive ion etching (DRIE) to create an array of nanochannels (FIG. 24B). These channels could range in size between ~100-900 nm in diameter, with a pitch between edges ranging around 1-25 times the diameter. FIG. 24C illustrates the backside of the wafer being etched by DRIE to gain fluidic access to the nanochannels (thus creating a through thickness array of nanochannels). FIG. 2D illustrates 2D array of nanochannels being etched into 3D via lithography patterning and anisotropic etching. Such 3D array of nanochannels allows simultaneous and graded cargo delivery at multiple tissue levels/layers. The 3D extrusions in FIG. 24D can range in size (at the base) between ~1 and hundreds of microns, depending on the number of nanochannels (and gap in-between) that need to be accommodated within/across it. In some cases the minimum number of nanochannels per 3D extrusion is 2, and these can be a different heights to be able to enable delivery of cargo at different levels of the tissue. Both nanochannels and/or 3D extrusions can be arranged into hexagonal close packing (HCP) arrays to maximize the active area of the device. Once the 3D extrusion is defined, the surface can be coated with an insulating layer, which could be silicon nitride or silicon dioxide. Additional coatings that could be applied to improve durability include (with compatible seed layers): silicon carbide, titanium nitride, aluminum titanium nitride, and zirconium nitride among others.

FIG. 25A illustrates a substrate with already defined nanochannels subjected to (FIG. 25B) surface micromachining (e.g., through a lithographic approach, or micromilling, for example) to create 3D extrusions of such nanochannel array (FIGS. 25C and 25D). In this case the base substrate could be made of DRIE'd silicon, or anodized alumina, or a tack-etched polymeric membrane (e.g. PET).

FIG. 26A shows that a processed DTN device can be diced into smaller modules. Such modules can be encased within a pliable polymeric frame to enable application on large/curved tissue surfaces. The picture in FIG. 26B shows an array of 3×3 modules being applied on a human arm. FIG. 26B large scale DTN could be used to intervene large/preclinical animal models and clinical models. In this case an ischemic skin flap of a pig was DTN'd with EFF, which induces the formation of (FIG. 26D) new vasculature that can (FIG. 26E) rescue the flapped skin from necrosis (left) by increasing perfusion to that area (right).

DETAILED DESCRIPTION

Definitions

Figure 1:
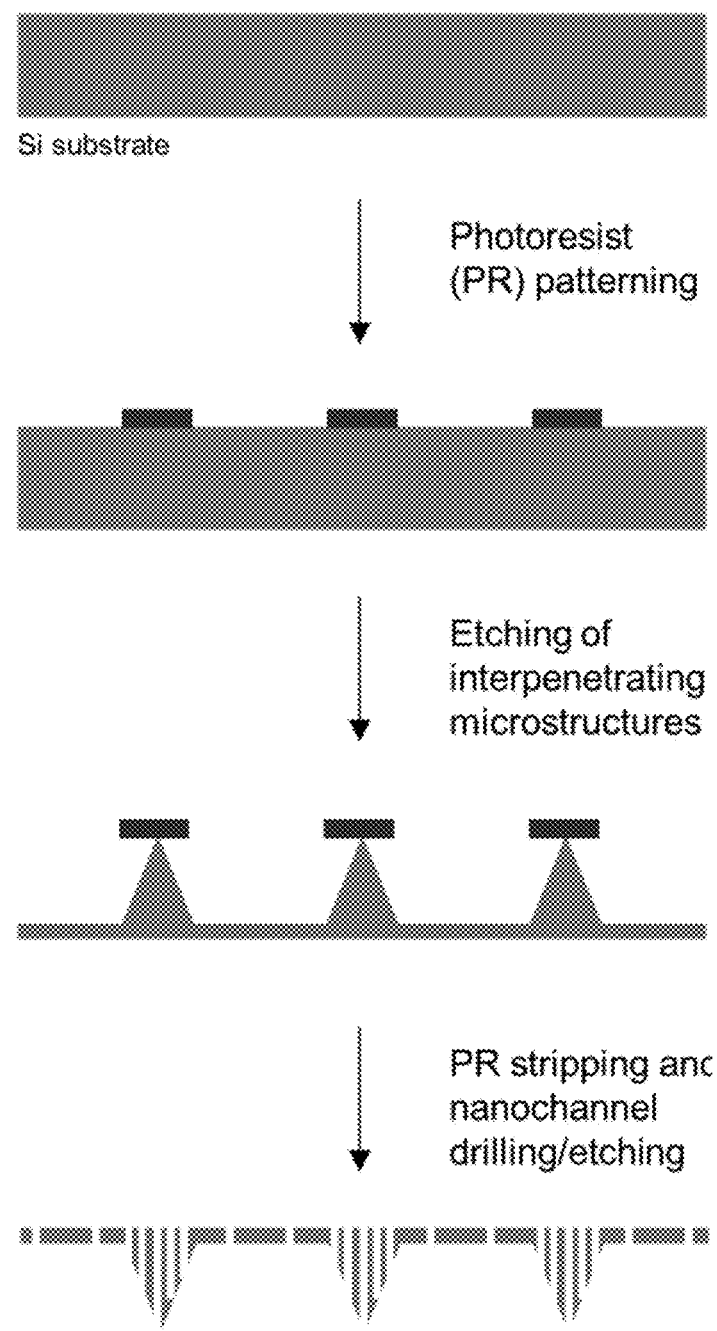
FIG. 1 is a schematic diagram showing the fabrication of arrayed interpenetrating nanochannels from silicon-based materials using photolithographic and etching techniques. First, an array of conical or pyramidal interpenetrating microstructures (approximately 20-500 microns tall) is defined on a silicon substrate using photoresist patterning and wet or dry etching. Subsequently, the silicon substrate is patterned on the back-side with an array of nanowells (approximately 300-1000 nm in diameter) using projection lithography, which is then followed by a highly anisotropic deep reactive ion etch (DRIE) to drill nanochannels through the silicon substrate/interpenetrating microstructures.

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

An "effective amount" is an amount sufficient to effect beneficial or desired results. An effective amount can be administered in one or more administrations, applications or dosages.

The term "carrier" or "pharmaceutically acceptable carrier" means a carrier or excipient that is useful in preparing a pharmaceutical or therapeutic composition that is generally safe and non-toxic, and includes a carrier that is acceptable for veterinary and/or human pharmaceutical or therapeutic use. As used herein, the terms "carrier" or "pharmaceutically acceptable carrier" encompasses can include phosphate buffered saline solution, water, emulsions (such as an oil/water or water/oil emulsion) and/or various types of wetting agents. As used herein, the term "carrier" encompasses any excipient, diluent, filler, salt, buffer, stabilizer, solubilizer, lipid, stabilizer, or other material well known in the art for use in pharmaceutical formulations and as described further below.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "therapeutically effective amount" or "therapeutically effective dose" refer to the amount of a composition, such as glucose-modified insulin bound to a glucose-binding structure, that will elicit the biological or medical response of a tissue, system, animal, or human that is being sought by the researcher, veterinarian, medical doctor or other clinician over a generalized period of time. In some instances, a desired biological or medical response is achieved following administration of multiple dosages of the composition to the subject over a period of days, weeks, or years.

The term "subject" or "recipient" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

Detailed Description

The microstructure array and methods of using the same disclosed herein are useful in transport of material into or across biological barriers. The microstructure array disclosed herein has the ability to deliver substances to different layers of cells within tissue simultaneously (or sequentially) because the microstructures comprise multiple channels which can reach different levels of cells. This is because multiple channels on an angled microstructure allow for different heights of the channels within the microstructure. When the microstructure penetrates tissue, the channels are placed within different layers of cells, and can therefore deliver substances at different levels within the tissue. The microstructure array can be used on the skin (or parts thereof); across the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers can be in humans or other types of animals, as well as in plants, insects, or other organisms, including bacteria, yeast, fungi, and embryos. The microstructure array can be applied to tissue internally with the aid of a catheter or laparoscope. For certain applications, such as for drug delivery to an internal tissue, the devices can be surgically implanted.

Referring to FIG. 1, the microstructure array (100) can comprise: a planar substrate (101) having a top surface (102) and a bottom surface (103); a reservoir (104) in fluid communication with the top surface of the planar substrate; and a plurality of microstructures (105) projecting from the bottom surface of the planar substrate, each of the plurality of microstructures comprising: a solid body portion (106) tapering from a base (107) to a distal tip (108) positioned at a height from the bottom surface of the planar substrate, thereby defining a microstructure surface; a first delivery channel (109) extending from the top surface of the planar substrate to a first channel opening (110) within the microstructure surface, thereby fluidly connecting the reservoir to the first channel opening; and a second delivery channel (111) extending from the top surface of the planar substrate to a second channel opening (112) within the microstructure surface, thereby fluidly connecting the reservoir to the second channel opening.

Each of the delivery channels can be the same or different in scale. In some embodiments, the delivery channels are nanochannels, e.g. having an inner diameter of about 1 to about 999 nm. In some embodiments, the delivery channels are microchannels, e.g. having an inner diameter of about 1 to about 999 µm. The size of the channel can be selected based on the size of the agent to be delivered and/or flow dynamics needed for a given application.

The planar substrate (101) can comprise a plurality of delivery channels (109, 111 for example), each of which extends from the top surface of the planar substrate to a channel opening (110, 112 for example) within the bottom surface (103) of the planar substrate, thereby fluidly connecting the reservoir (104) to the channel opening within the bottom surface of the planar substrate.

Figure 2:
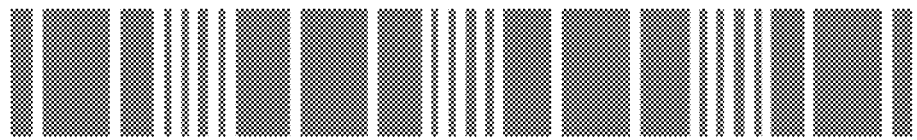
FIG. 2 is a schematic diagram showing an alternative method of fabricating arrayed interpenetrating nanochannels from silicon-based materials using etching techniques. Selective surface etching is used to define interpenetrating microstructures on a pre-made nanochanneled substrate platform.
Figure 2:
Figure 3:
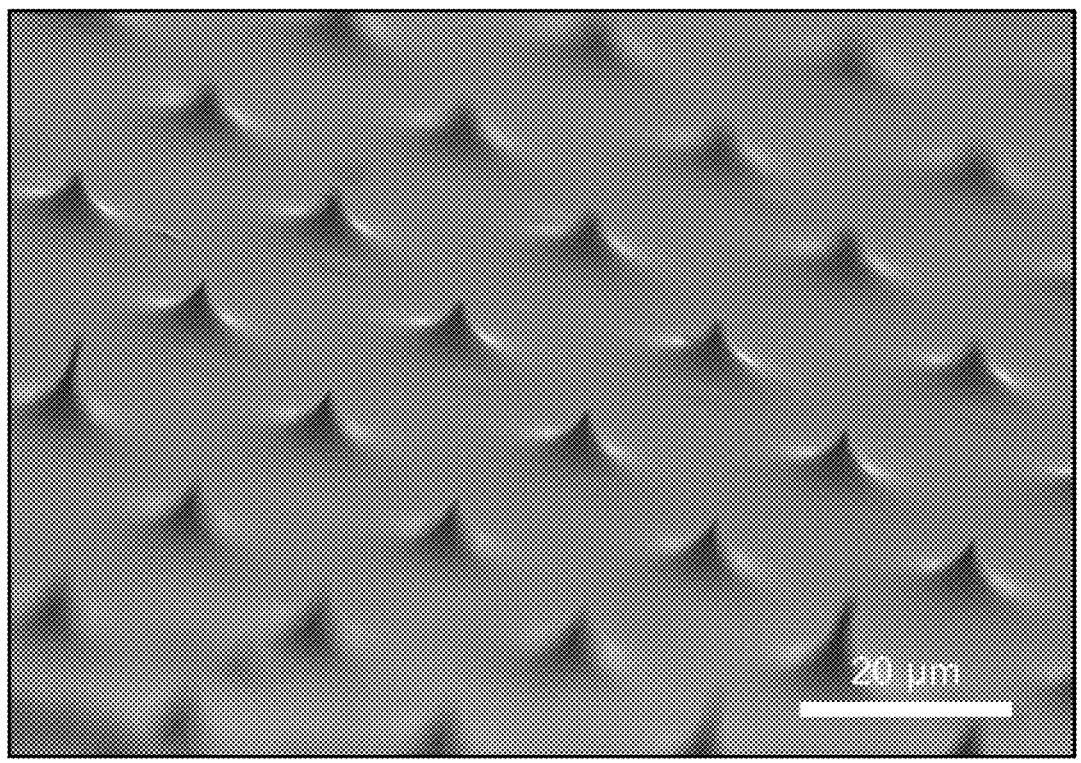
FIG. 3 is a high resolution image showing one embodiment of a microstructure array comprising nanochannels.
Figure 4:
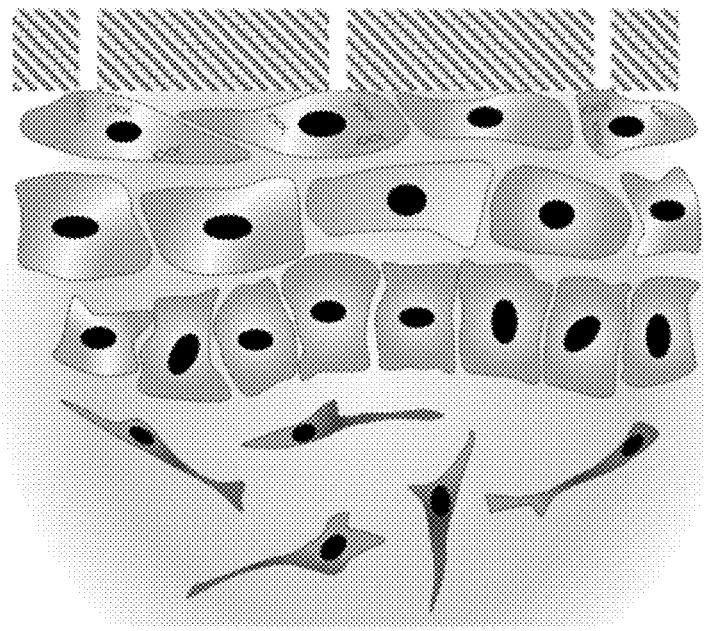
FIG. 4 is a schematic diagram showing the application of traditional nanochannel-based delivery (e.g. TNT) methods.
Figure 5:
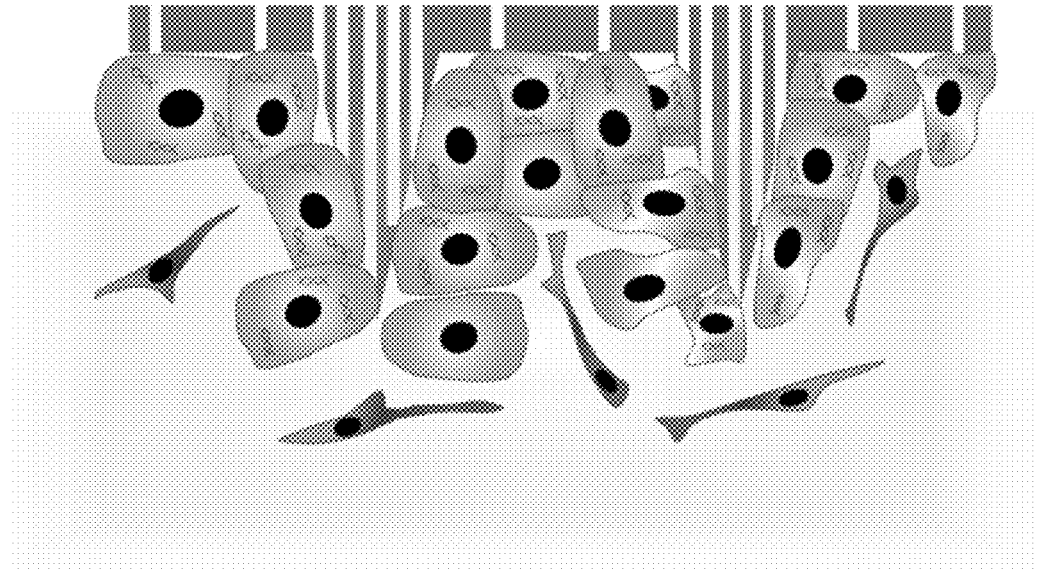
FIG. 5 is a schematic diagram showing the delivery of cargo into/across a biological barrier using an interpenetrating microstructure array comprising nanochannels.

As can be seen in FIGS. 1-2, the microstructure array (100) can be configured such that the first channel opening (110) is positioned within a first plane parallel to the planar substrate (101), wherein the second channel opening (112) is positioned within a second plane parallel to the planar substrate (101), and wherein the first plane is distally spaced apart from the second plane. There can also exist a third channel opening (114) connected to a third channel (113). The planes of each channel and its associated opening can be spaced at regular intervals from each other, or at different intervals. For example, each channel/channel opening can be spaced equally apart from the others. For example, the first and second channel openings can be distally apart by a distance of from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the height of the microstructure. In one example, the first plane can be distally spaced apart from the second plane by a distance of 20% to 60%. This distance can apply to third, fourth, fifth, and more channel openings as well.

The microstructures (105) can comprise 1, 2, 3, 4, 5, 6, 7, 8, 9, 10, 11, 12, or more channels. These channels can act as a conduit between the reservoir and the channel openings. Therefore, the channels can be in fluid communication with the reservoir, such that material placed in the reservoir can travel through the channel and be delivered at the channel openings. The first channel opening (110) can be positioned at the distal tip, with additional channel openings flanking the distal tip. For example, there can be three channel openings on the same microstructure, with one being at the distal tip, and an additional two channel openings (112 and 114) on either side of the distal tip. Multiple channels within the microstructure (105) can run parallel to each other, and can run parallel to the vertical plane of the microstructure, as shown in FIGS. 1 and 2.

Figure 17A:
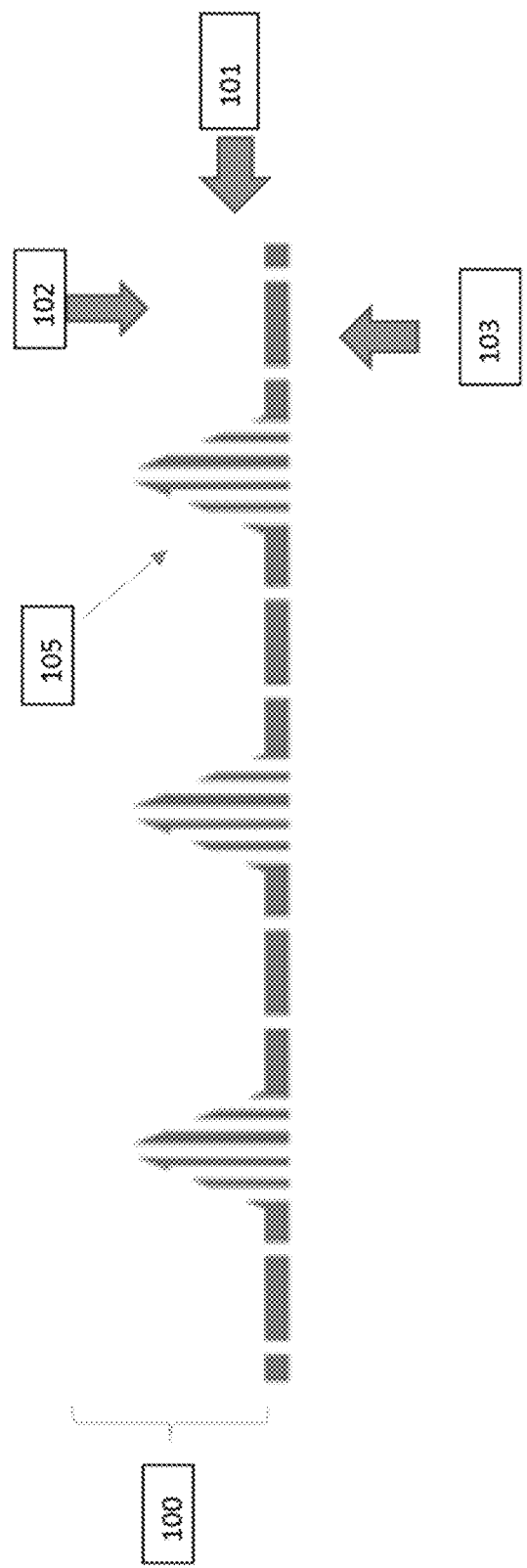
FIGS. 17A and 17B are illustrations of a cross-sectional view of an example microstructure embodiment.
Figure 17B:
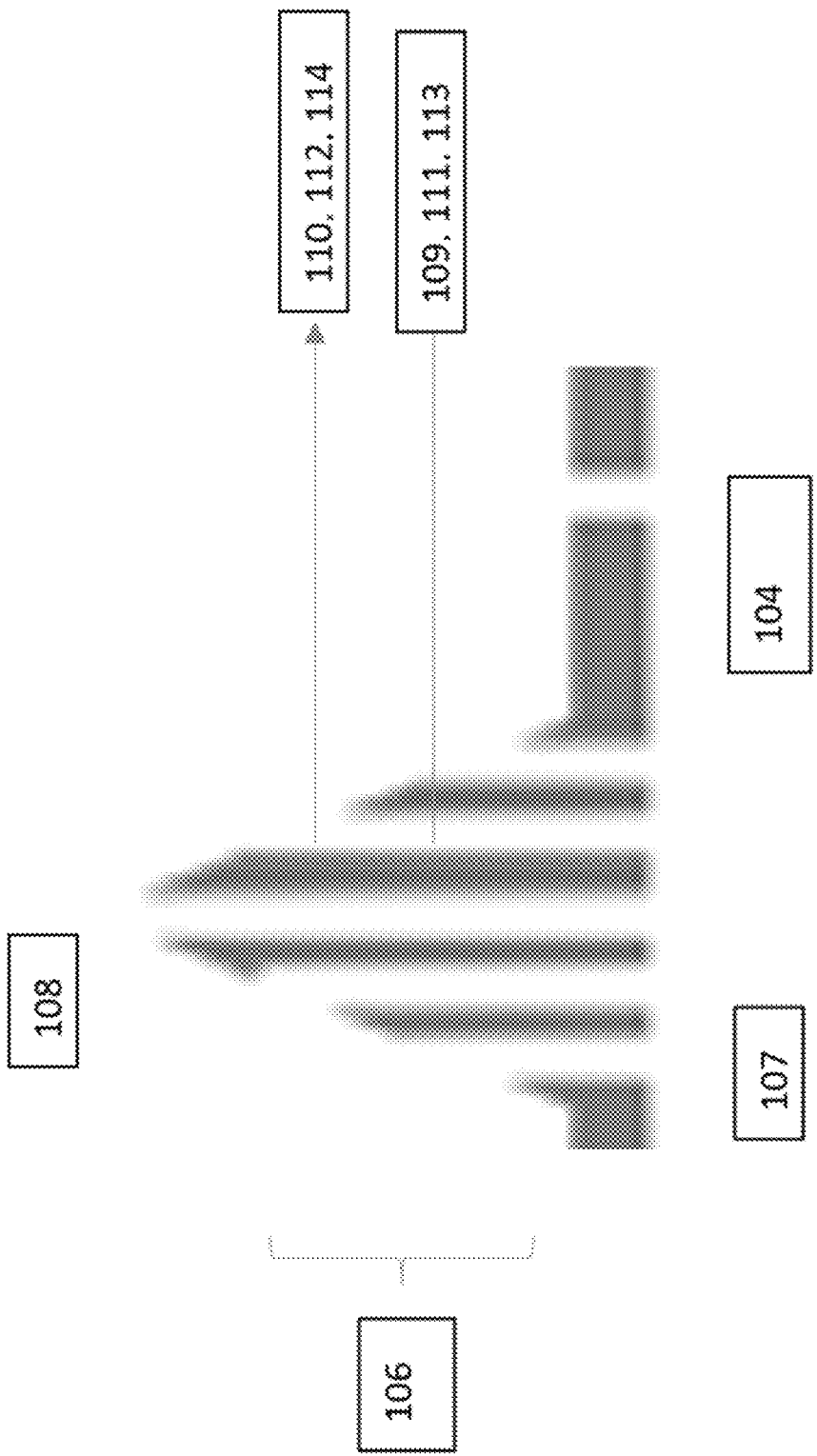

As can be seen in FIGS. 17A and 17B, the height of the solid body portion (106) of the microstructure (105) can be measured from the distal tip (108) of the microstructure to the base (107) of the microstructure, which can be located on the bottom surface (103) of the planar substrate (101). The height of the microstructure surface can be 5, 10, 15, 20, 30, 40, 50, 60, 70, 80, 90, 100, 200, 300, 400, 500, 600, 700, 800, 900, or 1000 microns in length, or more, less, or any amount in between. In one example, the height of the microstructure can be from 100 to 500 microns. As can be seen in FIG. 17A, the height of the microstructure (105) is measured in a plane b which can run perpendicular to the plane of the planar substrate (101).

The base (107) of the microstructure can have any shape, such as a triangle, square, diamond, rectangular, oval, or circle. In a particular embodiment, the base has a circular shape. When the base is a circle, the width of the base (107) of the microstructure (105) can be measured as the diameter of the base of the microstructure where it makes surface contact with the planar substrate (101). The plane a of the base (107) of the microstructure (105) can run parallel with the planar substrate (101), as seen in FIG. 17B. The width of the base can be 5, 10, 20, 30, 40, 50, 60, 70, 80, 90, 100, 200, 300, 400, or 500 microns in length, or more, less, or any amount in between. The width of the base can also be measured in relation to the height of the microstructure, so that, for example, the width of the base of the microstructure can be 10, 20, 30, 40, 50, 60, 70, 80, 90, 100, 150, or 200% of the height, or more, less, or any amount in between.

The distal tip (108) of the microstructure can have any shape, and can be pointed, rounded, slanted, flared, tapered, blunted or combinations thereof, as can be seen in FIG. 14A to 14D. In one embodiment, the microstructure is pointed.

Figure 18:
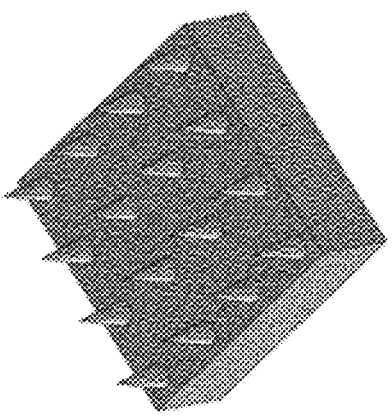
FIG. 18 shows various microstructure shapes.
Figure 18:
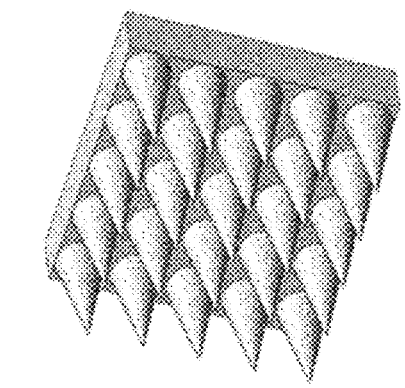
Figure 18:
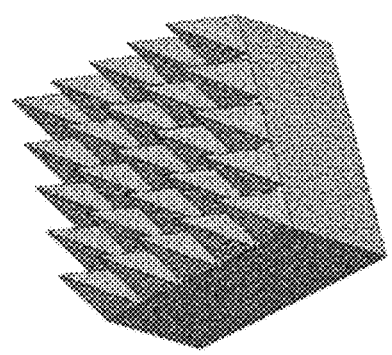
Figure 19:
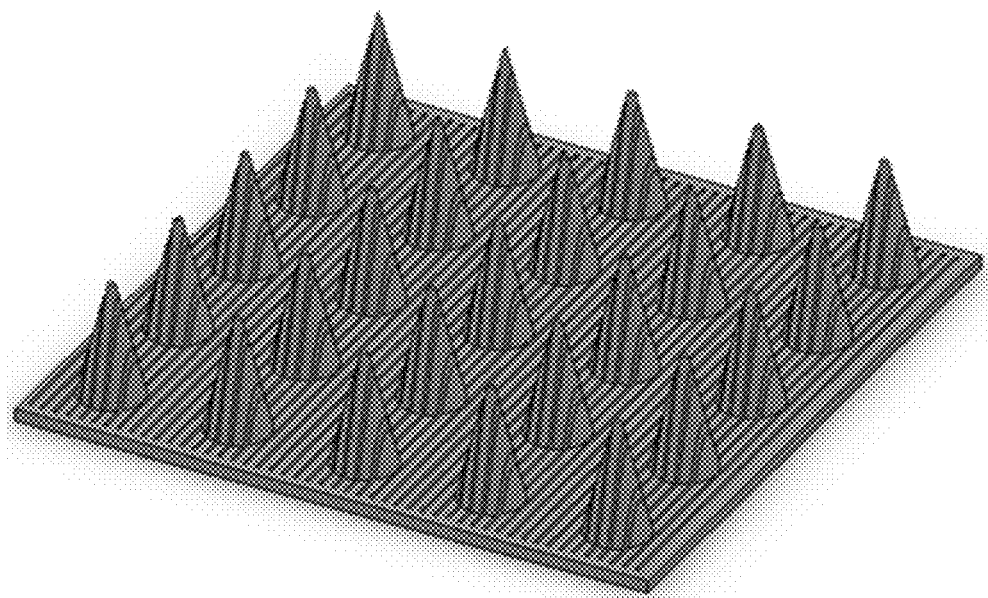
FIG. 19 is a perspective view of a microstructure array embodiment having long slits in the body portion.
Figure 20:
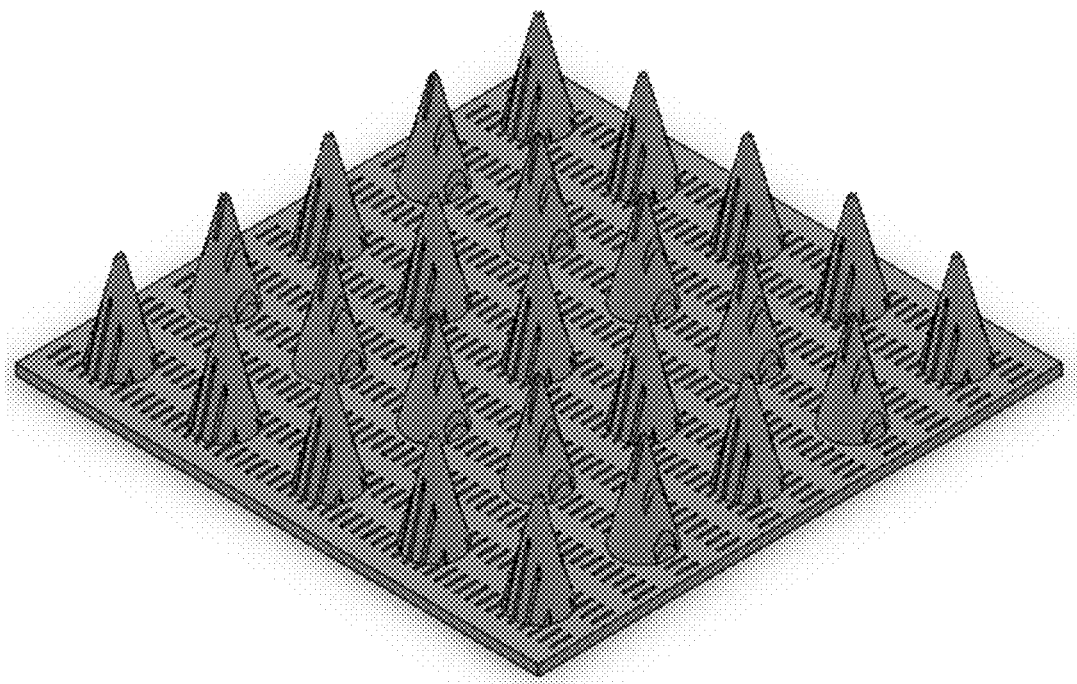
FIG. 20 is a perspective view of a microstructure array embodiment having short/arrayed slits in the body portion.
Figure 21:
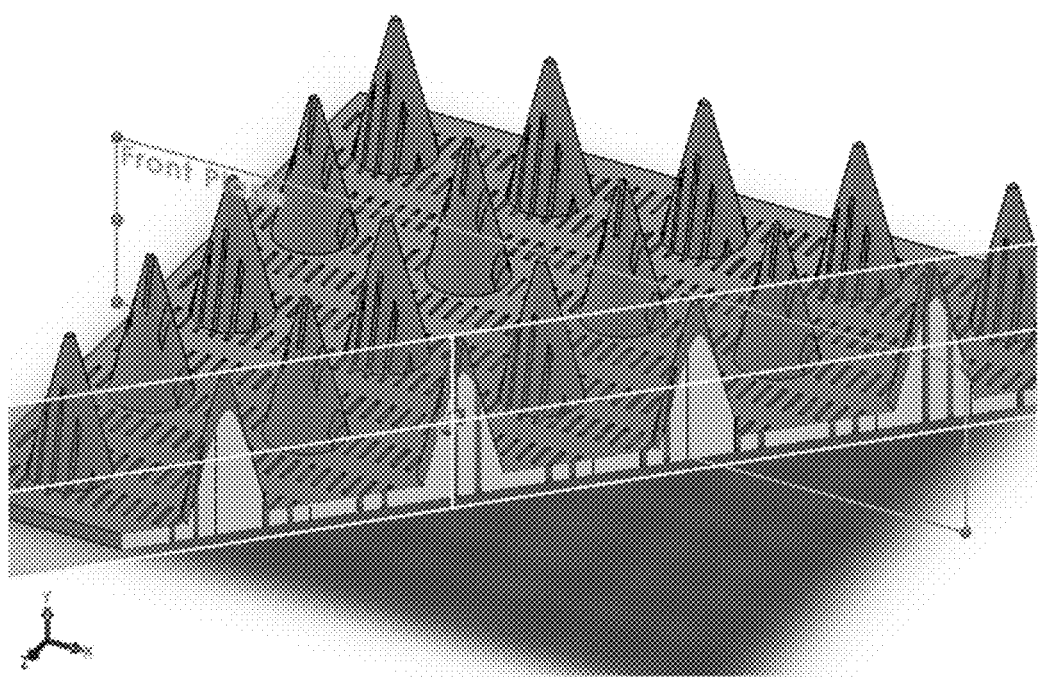
FIG. 21 is a cross-sectional view of the microstructure array embodiment of FIG. 20.

The microstructures can be spaced from each other at either regular intervals, or randomly. If spaced regularly, the microstructures can be 5, 10, 20, 30, 40, 50, 60, 70, 80, 90, 100, 200, 300, 400, 500, or 1000 or more microns apart from each other, as measured from centerline b. The solid body portion (106) of the microstructures can comprise any shape, such as a ridge, a herringbone pattern, a waveform pattern, cones, or pyramids. Examples of cones and pyramids can be seen in FIGS. 14A, 14B, and 18.

In some cases, the microstructures lack an ordered shape or pattern. For example, the disclosed microstructures could be produced by tailored/blank etching of a silicon surface to introduce randomly-distributed microstructures/roughness with sharp tips that can penetrate tissues/living systems.

The delivery channels (109, 111) can have various shapes, such as a cylinder, cuboid, or rectangular prism, for example. The opening of the delivery channel (110, 112) can be circular, rectangular, oval, or square, and as stated above, each microstructure (105) can have multiple channels, which can all have the same geometry, or can have shapes which differ from each other within the same or different microstructures. The delivery channel can have a substantially circular shape forming substantially concentric channels.

The reservoir (104) can comprise any substance to be delivered to a subject through the microstructure channel (109, 111). Conversely, substances can be drawn through the microstructure channel and deposited in the reservoir. The reservoir (104) can be in fluid communication with the microstructure opening (110,112) through the microchannel, which can run through the microstructure. The reservoir can therefore comprise any substance for transdermal administration. In one embodiment, the reservoir (104) is attached to the top surface (102) of the planar substrate, said top surface (102) being opposed to a bottom surface (104) of the planar substrate (101), wherein the microstructures project from the bottom surface.

Figure 22B:
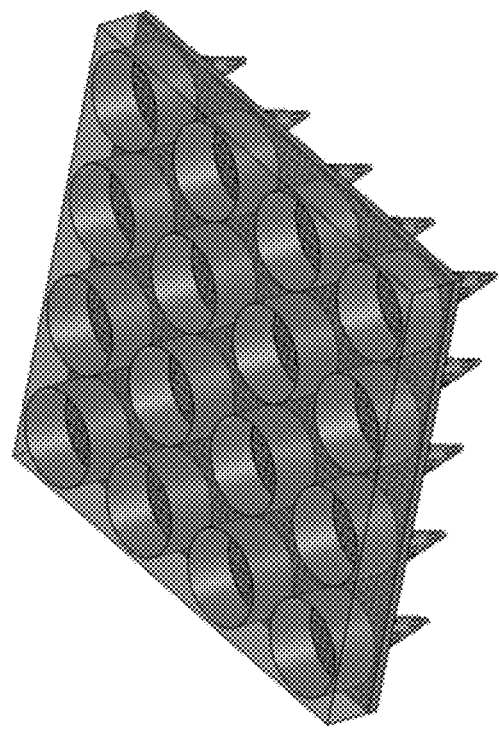
FIGS. 22A and 22B are perspective views of a microstructure array embodiment depicting reservoirs that can be machined into the body portion (FIG. 22A) or fabricated separately in another material and then interfaced with the body portion (FIG. 22B).
Figure 22A:
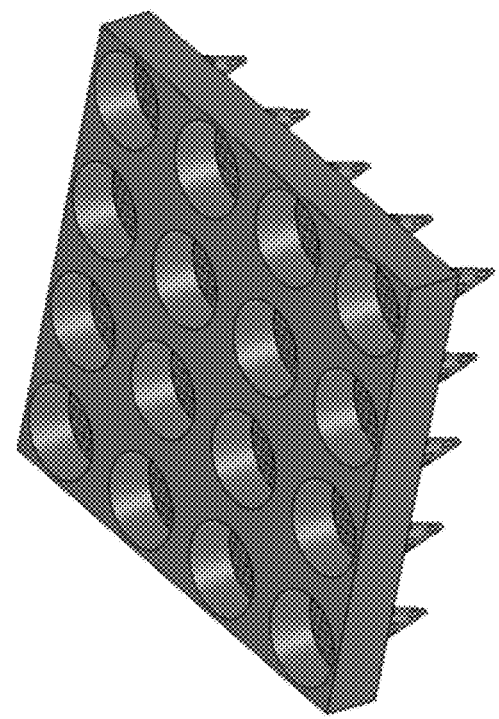

As shown in FIGS. 22A and 22B, the reservoir can be integral with the planar substrate (101) (FIG. 22A), or it can be fabricated separately, e.g. in another material, and then interfaced with the planar substrate (101) (FIG. 22B). The reservoirs can be sized to each feed a plurality of the microstructure channels, or arrayed so that each one feeds a single microstructure. For example, in some embodiments, the microstructure array (100) comprises a single large reservoir, either machined into the planar substrate (101) or interfaced with the planar substrate (101).

The reservoir can comprise a release mechanism for releasing the substance to be delivered, thereby permitting the substance to be transported into and through the at least one channel of the microstructure. The release mechanism may utilize a mechanical force or sheer force, which can be manually, by heat, a chemical reaction, an electric field, a magnetic field, a pressure field, ultrasonic energy, tension, diffusion injection, osmosis, concentration gradient, vacuum, pressure, or a combination thereof. In one embodiment, the reservoir (104) can include a porous material, wherein the substance to be administered is stored in pores of the porous material. In another embodiment, the reservoir is sealed. In one variation of this embodiment, the microstructure array further includes at least one puncturing barb extending from the first surface of the planar substrate, wherein the puncturing barb can be used to puncture the sealed reservoir.

The reservoir can, for example, comprise a feedback component, such that volume or amount of the substance to be transported across the biological barrier can be altered based on the physiological signal. The feedback component can comprise an "on and off" switch, such that when a signal is detected, the reservoir can deliver a substance to the recipient, but when no signal is detected, no substance is delivered. Conversely, the detection of a signal can have the opposite effect, wherein the reservoir defaults to delivery of a substance to the recipient, unless a signal is detected, which causes the reservoir not to release a substance for delivery to the recipient. By way of illustration, the feedback component can detect the presence of a pathogen in the subject, and when the substance is detected, the feedback component can allow for the release of an antibody from the reservoir.

In another example, the feedback component can detect changes in a physiological signal, such as pH or temperature. The feedback component can comprise a "cut off value" such that when the pH or the temperature changes by a certain amount, or reaches a certain numerical value (a pH below 6.5, for example, or a temperature above 99.1, for example), the feedback component allows for a change in the release of the substance, or the amount of the substance released, and subsequently administered to the recipient.

The feedback component can also adjust the amount or volume of the substance released based on the amount of signal detected, so that a greater amount of signal detected can result in a greater amount of substance released, or conversely, a greater amount of signal detected can result in a smaller amount of substance released.

The physiological signal detected can, in one aspect, be any substance present in the subject to which the microstructure array is being administered. For example, the physiological signal can be a biological substance or a drug. The substance can either occur naturally in the recipient, or can be a non-endogenous, or foreign, substance. In another aspect, the physiological response in the subject can comprise physiological environment factors, including pH and temperature. Examples of physiological signals include, but are not limited to, glucose, cholesterol, bilirubin, creatine, metabolic enzymes, hemoglobin, heparin, clotting factors, uric acid, carcinoembryonic antigen or other tumor antigens, reproductive hormones, oxygen, pH, temperature, alcohol, tobacco metabolites, and illegal drugs.

The substance in the reservoir to be delivered to the recipient can be a therapeutic, prophylactic, diagnostic, or theranostic substance. More than one substance can be delivered at a time, or different substances can be delivered sequentially. Different substances can be delivered through different channels at the same time, for example. 2, 3, 4, 5, 6, or more substances can be delivered simultaneously through different channels. Because the channel openings can reach different layers of cells, different substances can be administered to different strata of cells within tissue simultaneously utilizing the microstructure array disclosed herein. Specifically a first substance can be delivered via a first channel to a first layer of cells, and a second substance can be delivered via a second channel to a second layer of cells.

The substance to be delivered can be selected from the group consisting of peptides, proteins, carbohydrates, nucleic acid molecules, lipids, organic molecules, biologically active inorganic molecules, and combinations thereof. For example, a wide range of drugs may be formulated for delivery with the present microneedle devices and methods. As used herein, the terms "drug" or "drug formulation" are used broadly to refer to any prophylactic, therapeutic, diagnostic, or theranostic agent, or other substance that which may be suitable for introduction to biological tissues, including pharmaceutical excipients and substances for tattooing, cosmetics, and the like. The drug can be a substance having biological activity. The drug formulation may include various forms, such as liquid solutions, gels, solid particles (e.g., microparticles, nanoparticles), or combinations thereof. The drug may comprise small molecules, large (i.e., macro-) molecules, or a combination thereof. In representative, not non-limiting, embodiments, the drug can be selected from among amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants, antibiotics, analgesic agents, anesthetics, antihistamines, anti-inflammatory agents, and viruses. The drug may be selected from suitable proteins, peptides and fragments thereof, which can be naturally occurring, synthesized or recombinantly produced. In one embodiment, the drug formulation includes insulin.

The drug formulation may further include one or more pharmaceutically acceptable excipients, including pH modifiers, viscosity modifiers, diluents, etc., which are known in the art.

The reservoir disclosed herein can comprise the substance for release itself, or a means for producing a substance to be transported across the biological barrier reservoir. One example of a means for producing a substance is cells. The cells can be mammalian cells, such as human cells, or can be cells from any other source, which are capable of producing a substance for administration to a recipient. For example, the cells can pancreatic β cells or stem cell-differentiated human pancreatic cells.

The substance, or the means for producing the substance, can be disposed in a reservoir which is semi-permeable, for example. This can allow for the exchange of fluid with the recipient, such that the feedback component can be in fluid communication with the recipient, and thereby detect changes in physiological signal of the recipient. For example, the reservoir can comprise cells, wherein the cells are sensitive to changes in a physiological signal from the recipient. Such physiological changes in the recipient can stimulate the cells to release a substance, or to stop releasing a substance, as described above in regard to the feedback component. In one example, the reservoir can comprise an alginate microgel.

Figure 23:
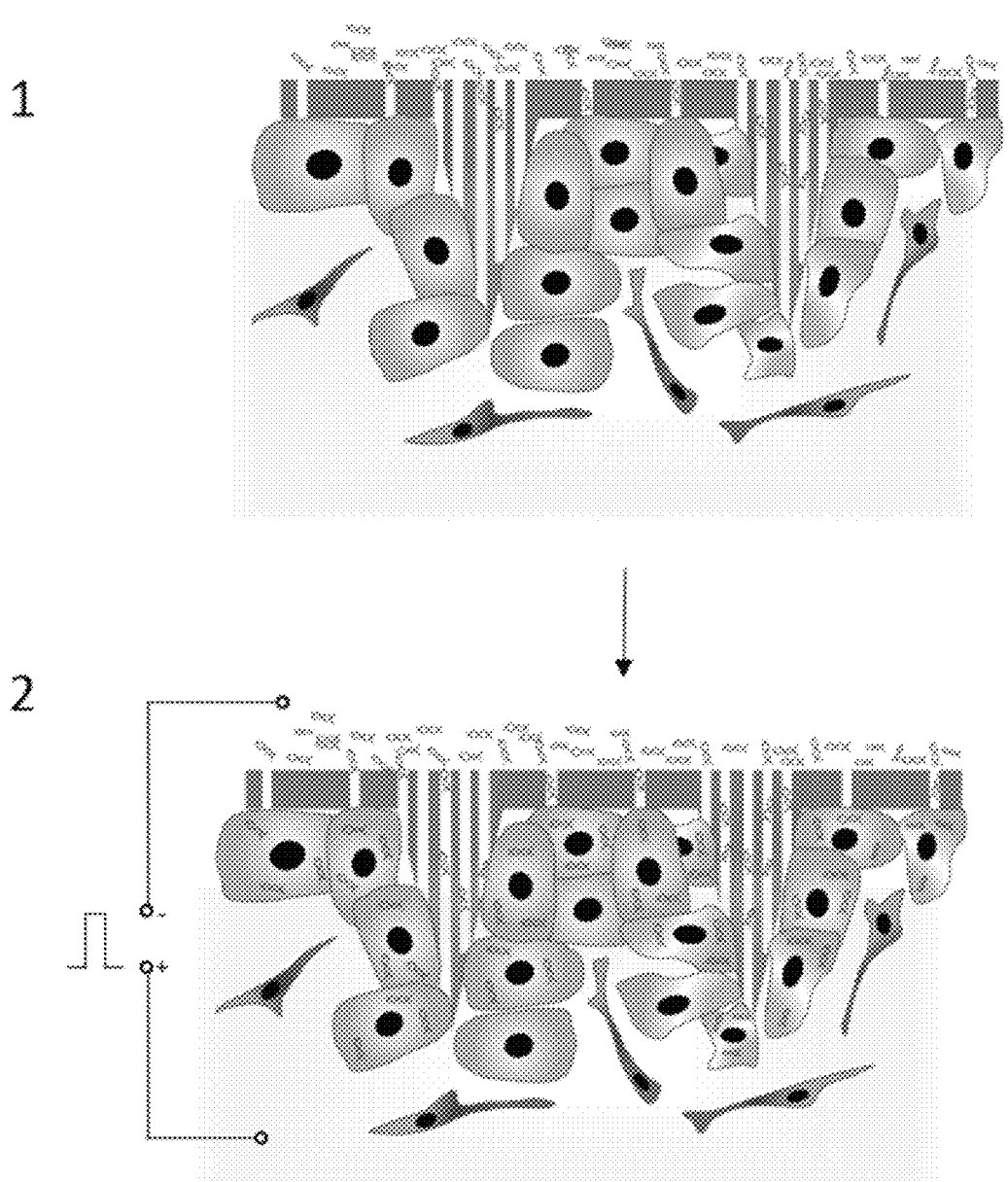
FIG. 23 illustrates an embodiment microstructure viewed as a cross-section and its use for delivery of nucleic acid into skin tissue using electroporation.
Figures 24A, 24B:
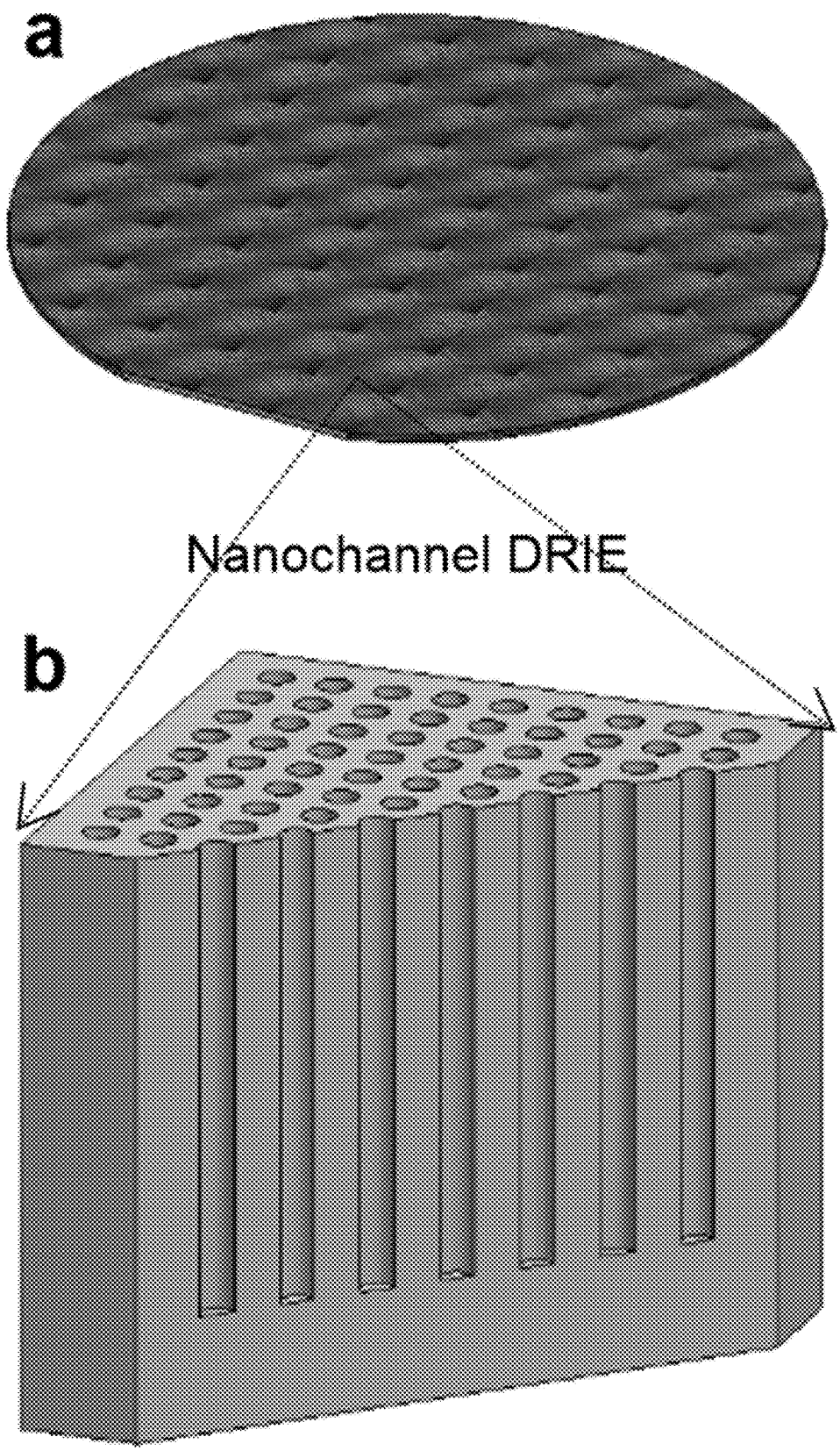
FIGS. 24A to 24D illustrate manufacturing of an embodiments microstructure.
Figure 24C:
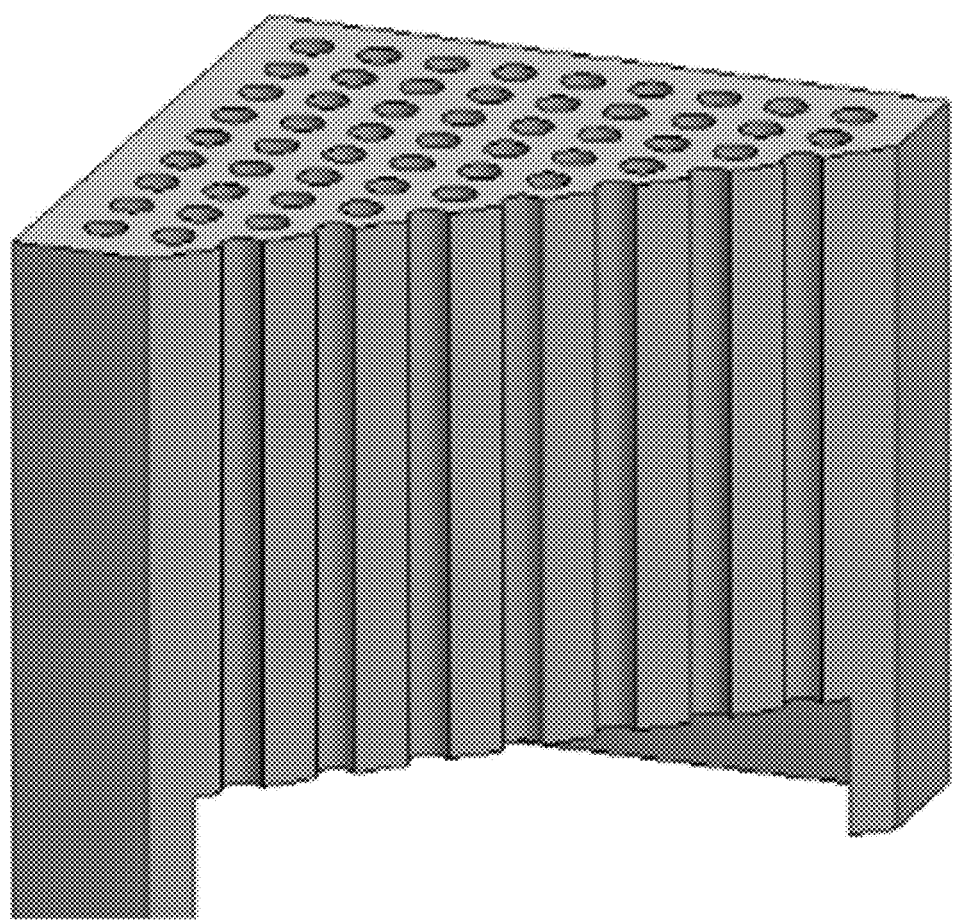
Figure 24D:
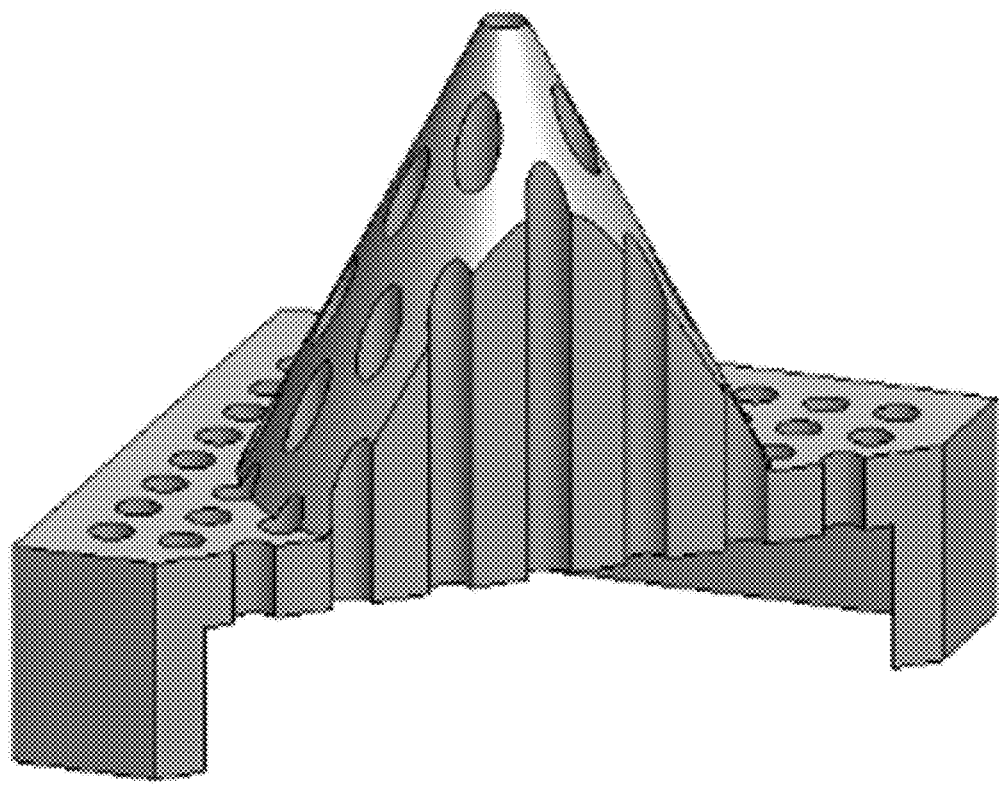
Figure 25A:
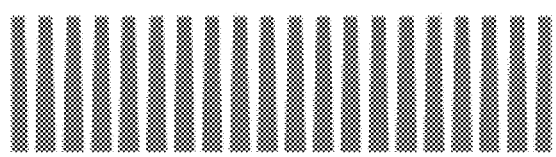
FIG. 25A to 25D illustrate an alternative fabrication approach.
Figure 25B:
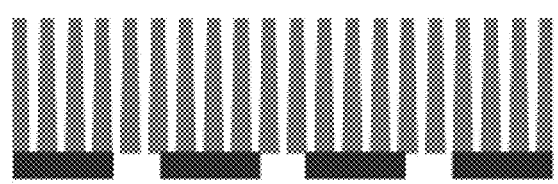
Figure 25C:
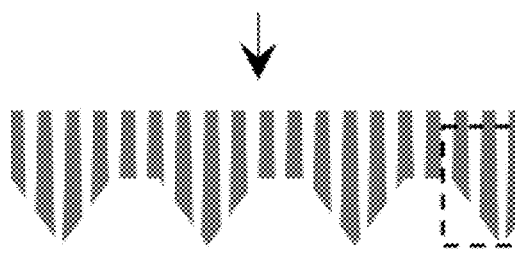
Figure 25D:
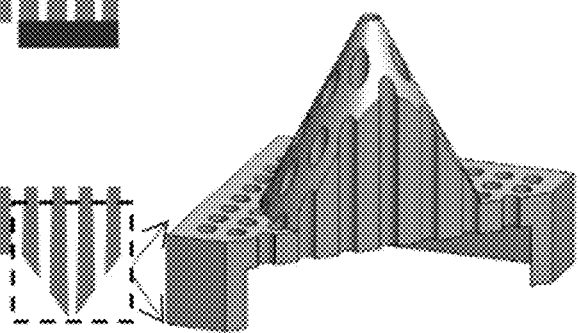
Figure 26A:
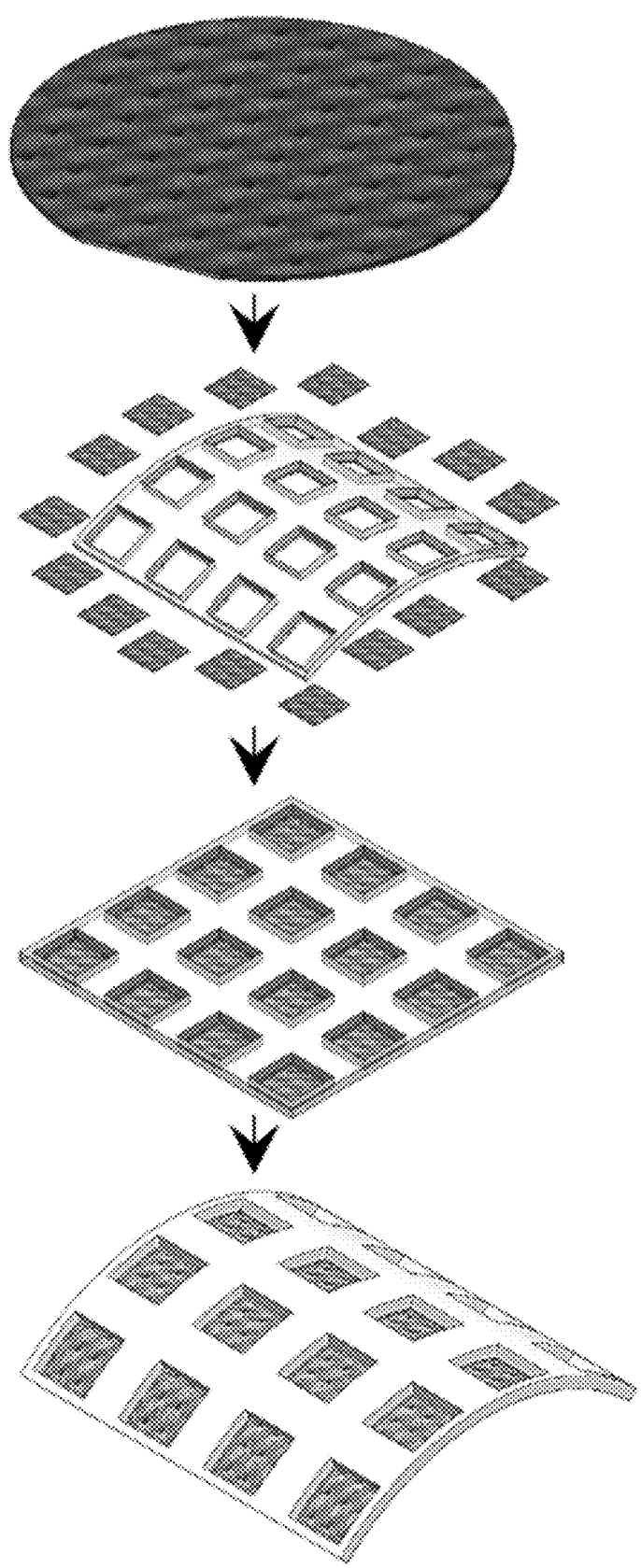
FIGS. 26A to 26E illustrate embodiments for application to large/curved tissue surfaces.
Figure 26B:
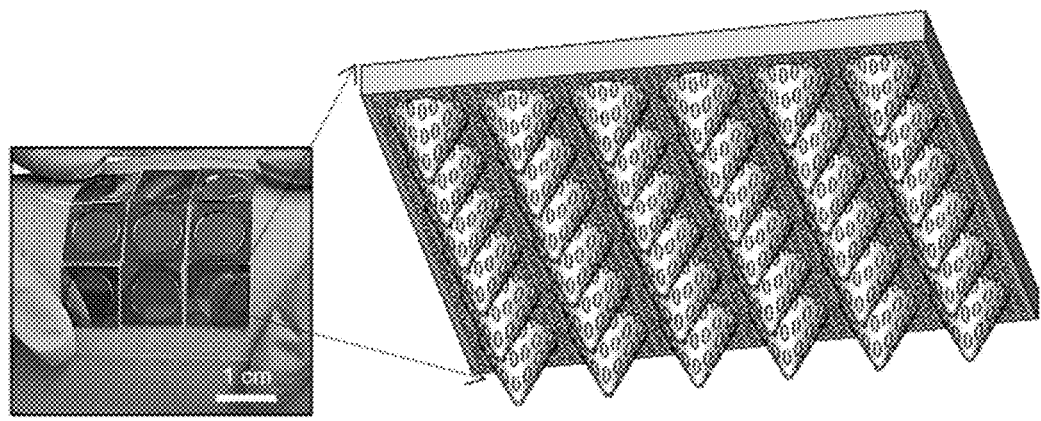
Figure 26C:
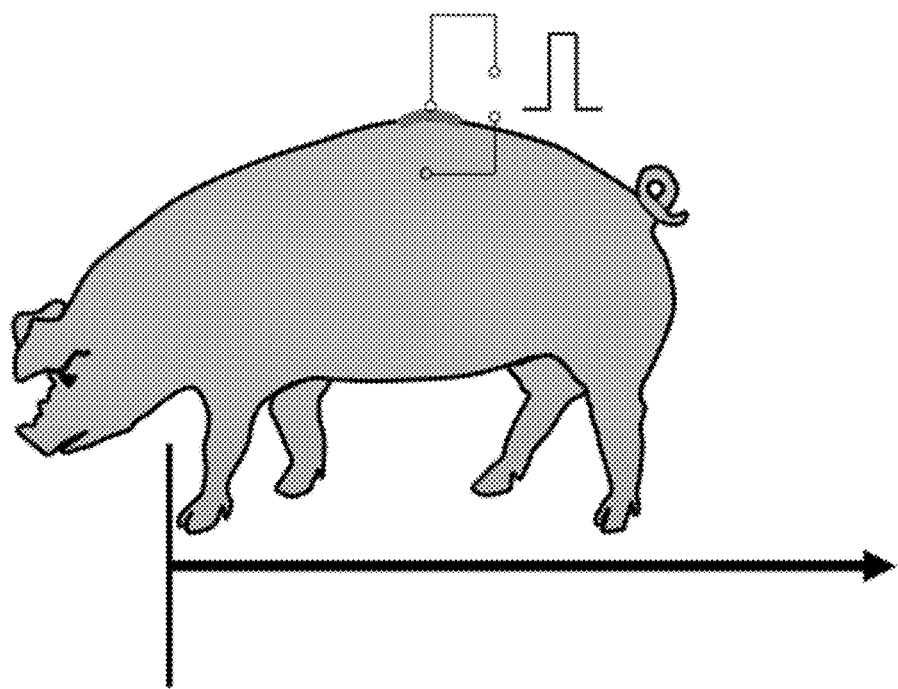
Figure 26D:
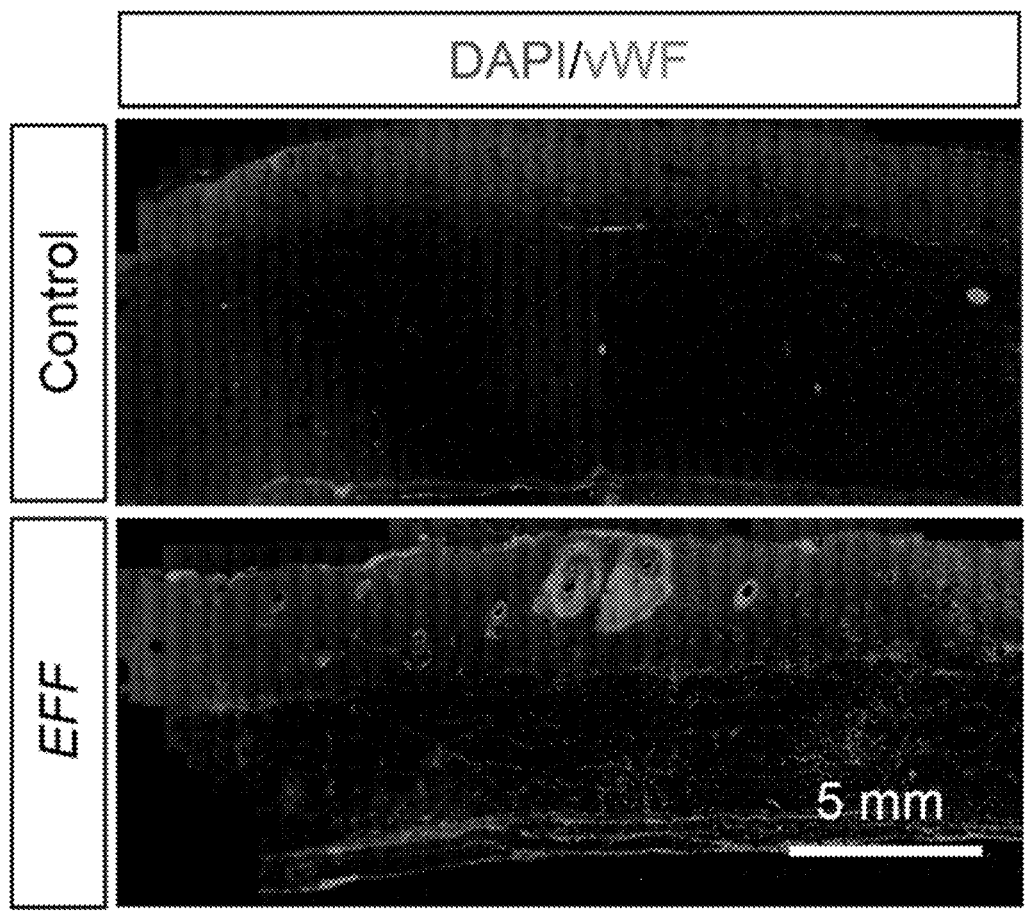
Figure 26E:
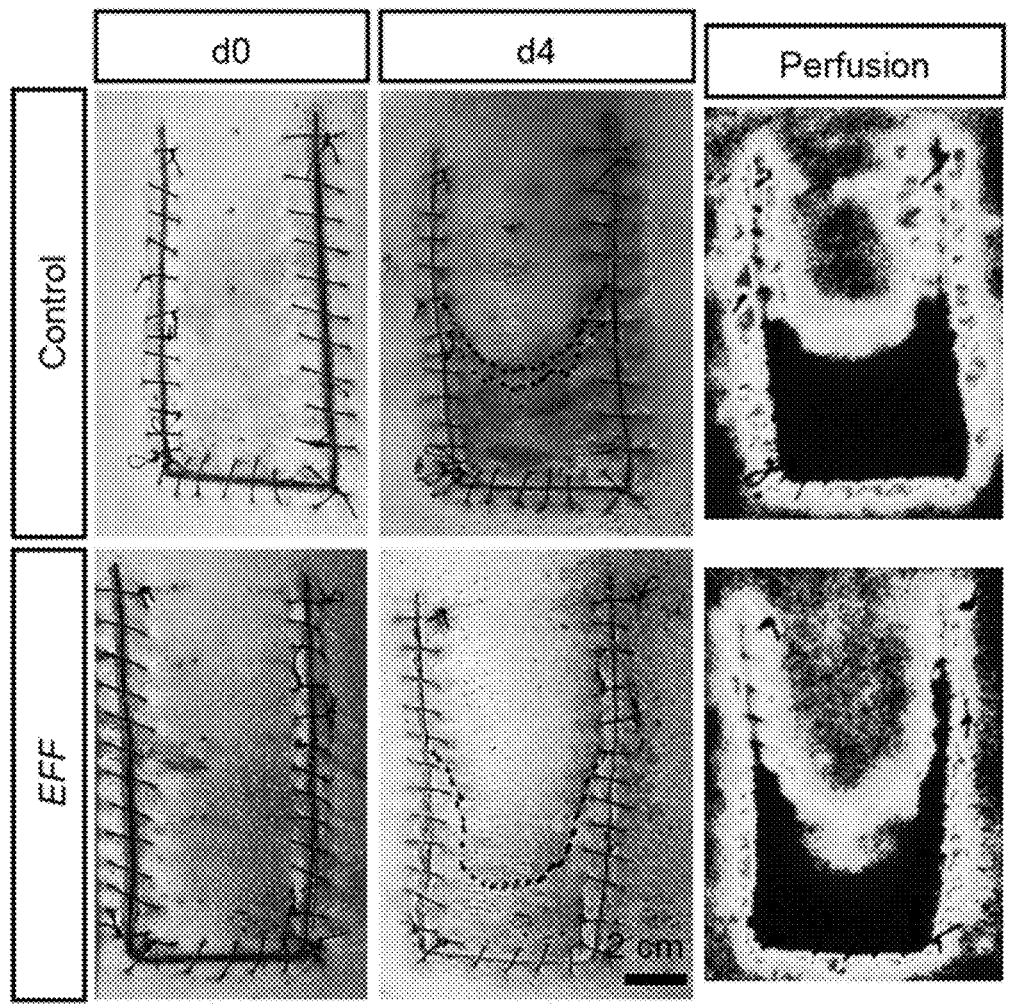
Figure 27A:
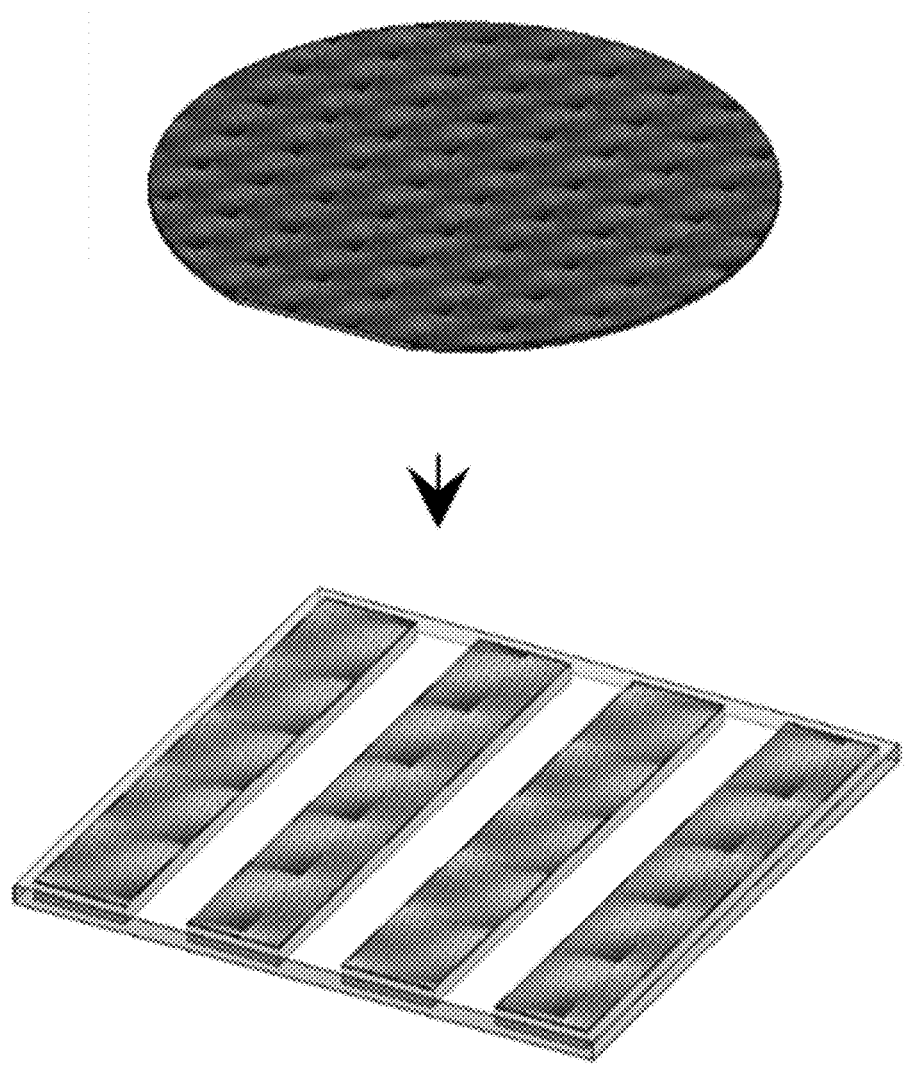
Figure 27B:
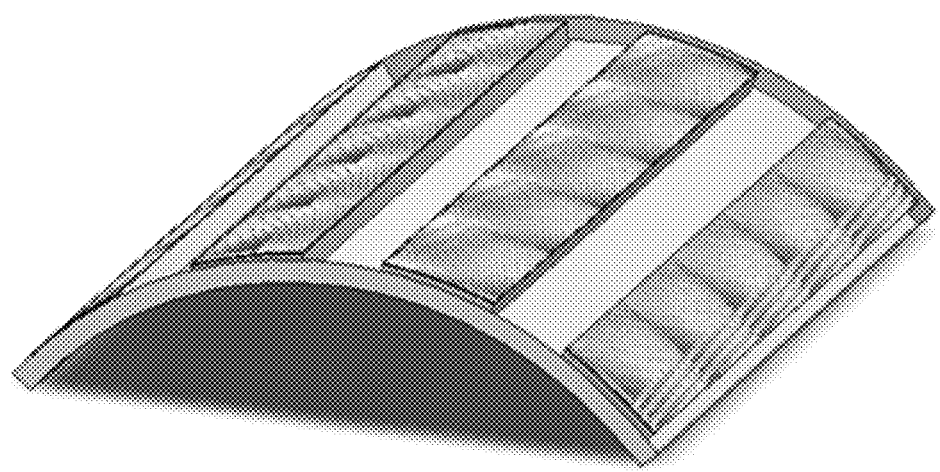
Figure 27C:
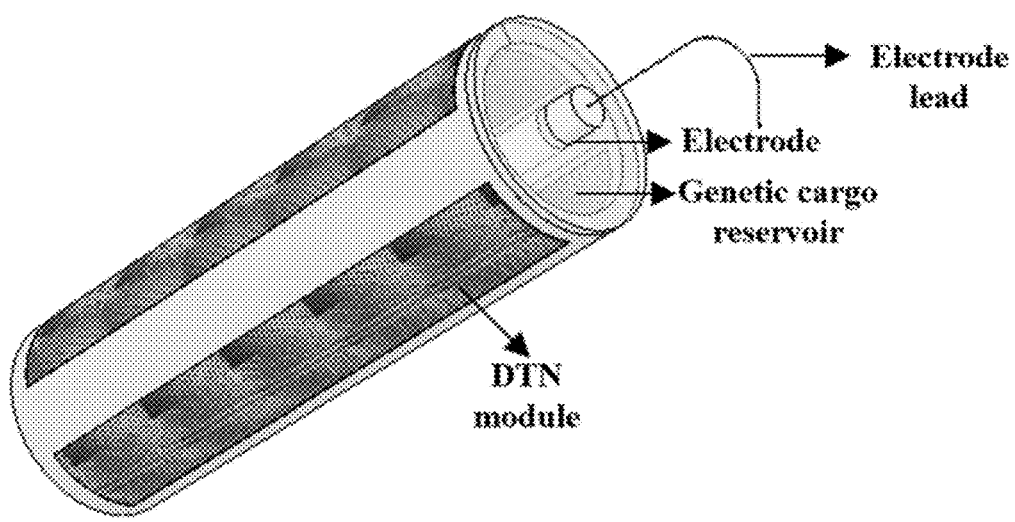
Figure 27D:
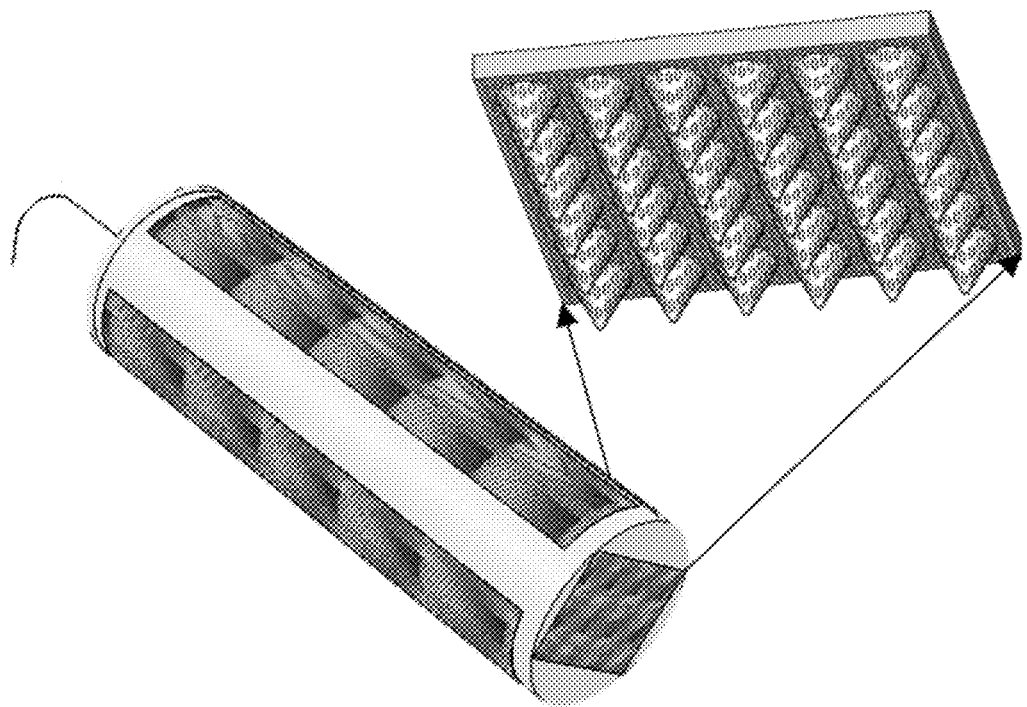
Figure 27E:
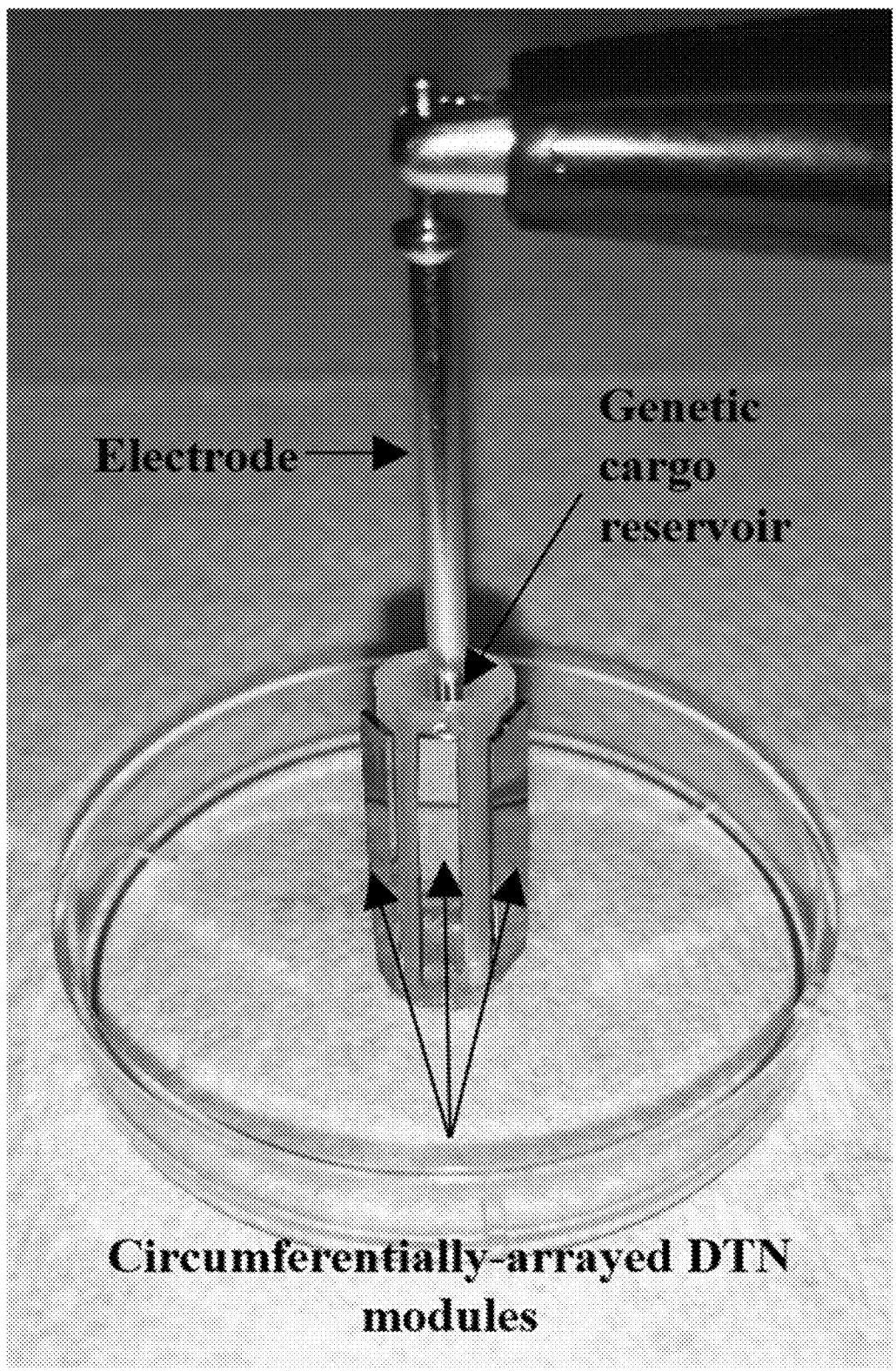
Figure 27F:
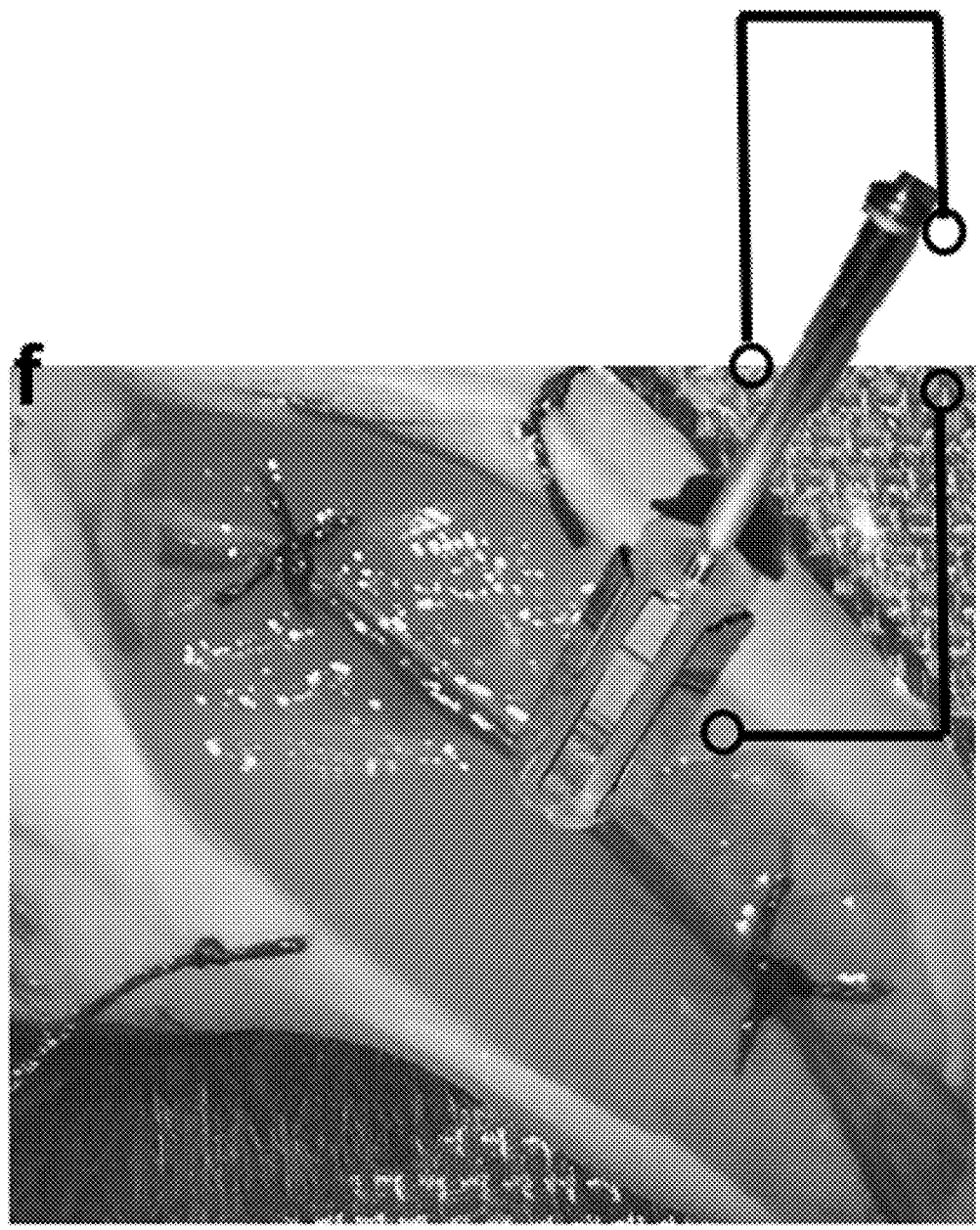
Figure 27G:
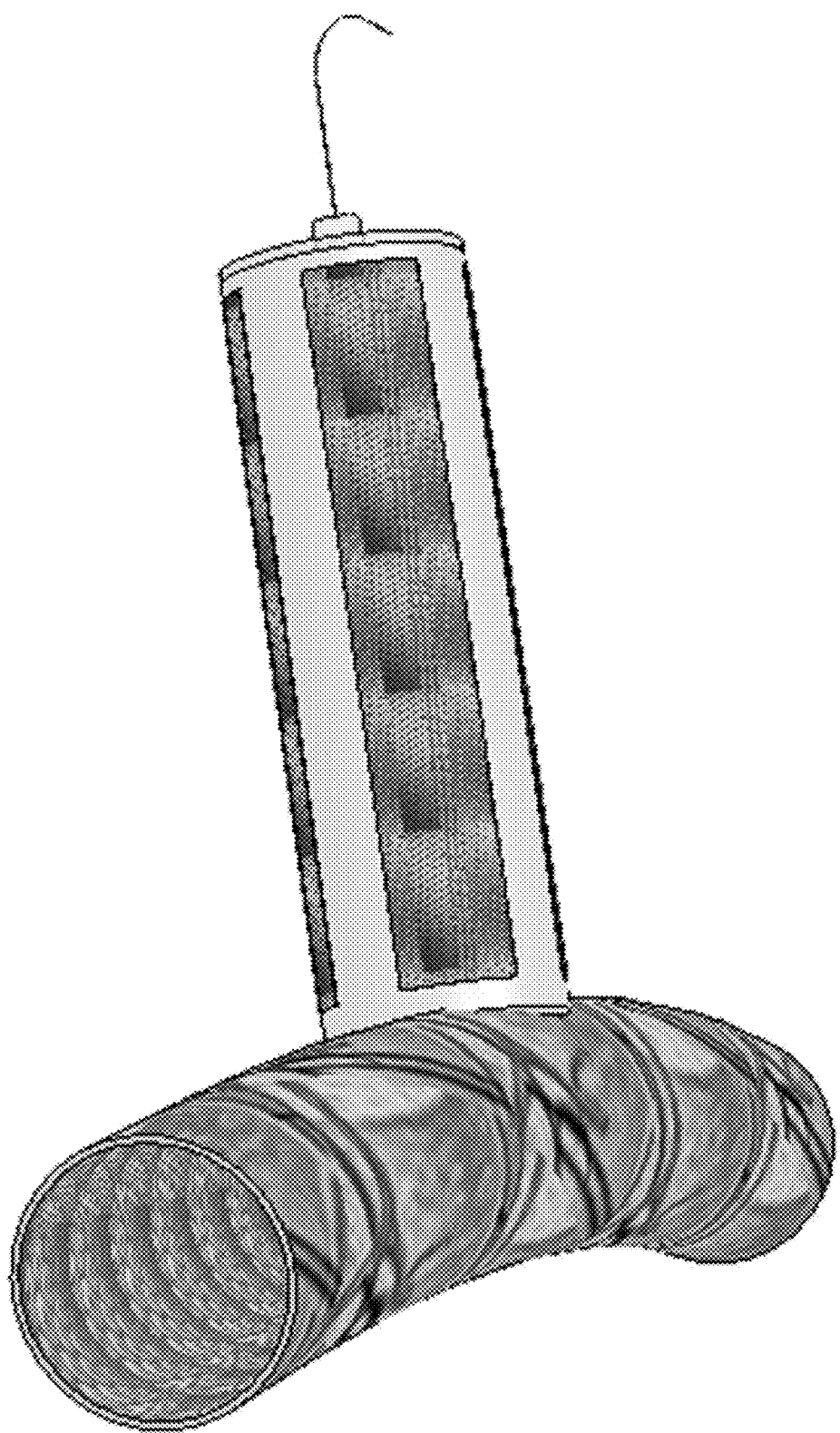
Figure 27H:
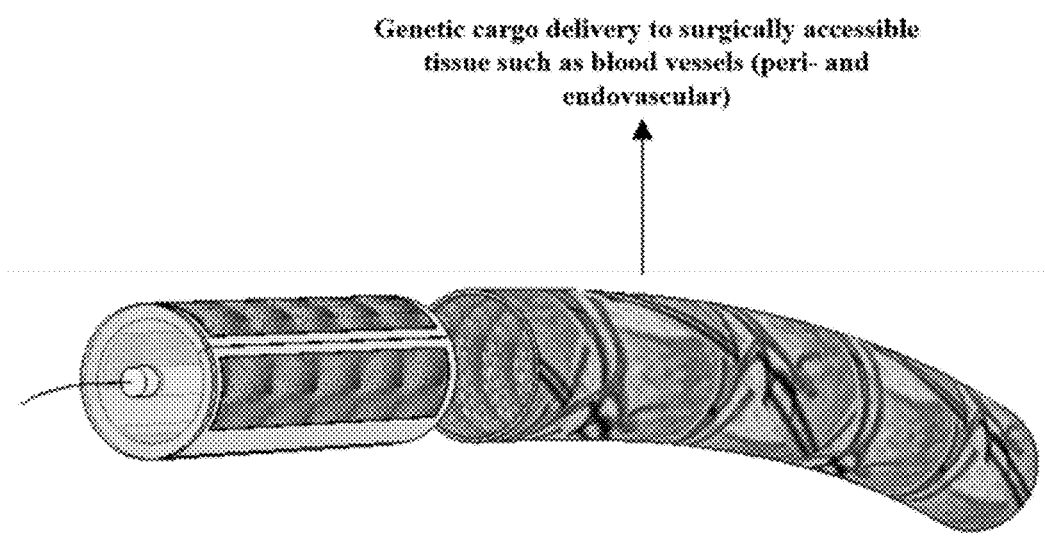

The microstructure array 100 disclosed herein can further include a stimulus (release mechanism) for translocating the cargo from the reservoir to through the channels. In some cases, this stimulus involves formation electrical field (e.g. electroporation), in which a porating electric field is applied to disrupt/deform lipid membranes and allow intracellular cargo delivery. In some embodiments, applying a porating electric field across the system results in the deformation and/or disruption of cellular membranes, which allows for cargo translocation into the intracellular space. Electric field strengths can be accommodated depending on the target tissue/system. For example, FIG. 23 illustrates use of the disclosed microstructure array 100 to deliver nucleic acids into skin tissue using electroporation.

In other embodiments, the stimulus involves mechanical force, sheer force, heat, chemical reaction, magnetic field, pressure field, ultrasonic energy, tension, diffusion injection, osmosis, concentration gradient, vacuum, pressure, or a combination thereof. In some embodiments, the cargo comprises proteins, nucleic acids, or particles. However, in some embodiments, an electrical stimuli is the cargo being delivered. Pulsed electric fields have many applications, e.g. in regenerative medicine. The disclosed microstructure array 100 could be used to deliver pulsed electric fields at different levels across the tissue thickness.

Microneedles and electroporation apparatus are described in U.S. Pat. Nos. 6,334,856; 6,331,266; 6,312,612; 6,241,701; 6,233,482; 6,181,964; 6,090,790; 6,014,584; 5,928,207; 5,869,326; 5,855,801; 5,823,993; 5,702,359; 5,697,901; 5,591,139; 5,389,069; 5,273,525; and 7,127,284, which are incorporated by reference for this teaching.

The microstructure array can comprise a first electrode in electrical contact with a second electrode, wherein the first electrode is in contact with the reservoir and the second electrode is in contact with one or more cells of a tissue while the microstructure array is in use. In order to enhance uptake of the substance, which may be a gene, other nucleic acid, protein or other large molecule, a small molecule drug, or the like, an electric field can be established between electrodes spaced apart on opposite sides of the opening. The voltage, frequency, and other electrical field parameters will be selected primarily based on the distance between the electrodes.

The microstructure array comprising electrodes can comprise a first electrode structure formed at the distal tip (108) of the microstructure, such that it comes in contact with the cells and tissue that have been punctured by the microstructure. The second electrode structure can be disposed at the reservoir. The electrodes structures can be formed as concentric bands that are connected to conductive pads. Each band and banded segment can be wired together to an electroporation power supply, wired separately to an electroporation power supply, and can be energized in a variety of geometric and timed patterns and arrangements. Moreover, the different bands and band segments can be maintained at different electrical potentials (voltages) with respect to the first electrode structure. A substance can be delivered through a channel opening (110, 112) at the distal tip (108) so that it permeates through tissue outwardly in a region. The region can coincide with the electrical field being generated between first electrode structure and second electrode structure. The electrical field enhances a cellular permeability, thus enhancing the delivery of the desired target substance to the cells.

The electroporation power supply can be a conventional power supply. The requirements and specifications of such power supplies are well described in the literature. See, for example, Neumann et al., Electroporation and Electrofusion in Cell Biology, Plenum Press, New York, N.Y., 1989; Chang et al., Guide to Electroporation and Electrofusion, Academic Press, San Diego, Calif., 1992; Jaroszeski et al., Eletrochemotherapy, Electrogenetherapy, and Transdermal Drug Delivery: Electrically Mediated Delivery of Molecules to Cells, Humana Press, Totowa, N.J., 2000; and Lynch and Davey, Electrical Manipulation of Cells, Chapman & Hall, New York, N.Y., 1996. The full disclosures of each of these publications are incorporated herein by reference.

The microstructure array capable of electroporation can comprise an alternating current power supply adapted to deliver electroporation current to the electrode structures at a desired voltage and frequency, typically selected to deliver electroporation current to the electrodes at a voltage in the range from 0.1 V to 30 kV. In some cases, the voltage is less that about 300 to 500V. The particular voltage will depend at least in part on the spacing between the first and second electrode structures. The frequency will typically be in the range from 10 Hz to 107 Hz, usually from 104 Hz to 106 Hz. The current can be applied at pulsed intervals, such as every 1, 2, 3, 4, 5, 6, 7, 8, 9, 10, 11, 12, 13, 14, 15, 16, 17, 18, 19, 20, or more milliseconds, or any amount in between. 1, 2, 3, 4, 5, 6, 7, 8, 9, 10, 11, 12, 13, 14, 15, 16, 17, 18, 19, 20, or more pulses can be applied in a given interval, and the intervals can be repeated until the desired result is achieved.

Also disclosed herein is a method for delivering one or more substances to multiple cell levels of a tissue, comprising: providing a microstructure array (100) comprising: a planar substrate (101) having a top surface (102) and a bottom surface (103); a reservoir (104) in fluid communication with the top surface of the planar substrate, wherein the reservoir comprises the substance to be delivered; and a plurality of microstructures (105) projecting from the bottom surface of the planar substrate, each of the plurality of microstructures comprising: a solid body portion (106) tapering from a base (107) to a distal tip (108) positioned at a height from the bottom surface of the planar substrate, thereby defining a microstructure surface; a first delivery channel (109) extending from the top surface of the planar substrate to a first channel opening (110) within the microstructure surface, thereby fluidly connecting the reservoir to the first channel opening; and a second delivery channel (111) extending from the top surface of the planar substrate to a second channel opening (112) within the microstructure surface, thereby fluidly connecting the reservoir to the second channel opening; delivering the one or more substances within the reservoir through the delivery channels to multiple cell levels of the tissue.

Also disclosed herein is a method for delivering extracellular vesicles from one layer of cells to another layer of cells, comprising: providing a microstructure array comprising: a planar substrate having a top surface and a bottom surface; a reservoir in fluid communication with the top surface of the planar substrate, wherein the reservoir comprises the substance to be delivered; and a plurality of microstructures projecting from the bottom surface of the planar substrate, each of the plurality of microstructures comprising: a solid body portion tapering from a base to a distal tip positioned at a height from the bottom surface of the planar substrate, thereby defining a microstructure surface; a first channel extending from the top surface of the planar substrate to a first channel opening within the microstructure surface, thereby fluidly connecting the reservoir to the first channel opening; and a second channel extending from the top surface of the planar substrate to a second channel opening within the microstructure surface, thereby fluidly connecting the reservoir to the second channel opening; isolating extracellular vesicles from a first layer of cells through the first channel; delivering the extracellular vesicles to a second layer of cells via a second channel. In one example, the first layer of cells can be closer to the external surface than the second layer of cells.

The solid body portion of the microstructure array disclosed herein, including the planar substrate and reservoir, can be formed from a variety of materials, including silicon. Disclosed herein is a method for making the microstructure array (100). This can include the steps of forming a substantially planar substrate (101); and forming a plurality of microstructures (105) projecting at an angle from the plane in which the planar substrate lies, the microstructures having a base (107) integrally connected to the substrate, a distal tip (108) connected to the base, and body portion (106) therebetween, wherein at least one of the microstructures has at least one channel (109) extending substantially from the base portion through at least a part of the body portion, the channel being open along at least part of the body portion and in fluid communication with the reservoir (104). In various embodiments, the step of forming the microstructures comprises embossing, injection molding, casting, photochemical etching, electrochemical machining, electrical discharge machining, precision stamping, high-speed computer numerically controlled milling, Swiss screw machining, soft lithography, directional chemically assisted ion etching, or a combination thereof.

Also disclosed herein is a method is provided for administering a substance to a subject in need thereof, which includes the steps of inserting into the skin of the subject the microstructures (105) of the array (100) described above, and causing the substance to be transported from the reservoir (104) through the at least one channel of the microstructure and through the stratum corneum of the skin.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Use of Tissue Nanotransfection Device for Direct Cystolic Delivery of Reprogramming Factors Disclosed herein is a device to topically and controllably deliver reprogramming factors to tissues through a nano-channeled device (FIG. 6). Such tissue nano-transfection (TNT) approach allows, for example, the direct cytosolic delivery of reprogramming factors by applying a highly intense and focused electric field through arrayed nanochannels (Gallego-Perez et al. Nanomedicine 2015; Boukany et al. Nat Nanotechnol 2011, 6(11): 747-754), which benignly nanoporates the juxtaposing tissue cell membranes, and electrophoretically drives reprogramming factors into the cells (FIG. 6 a-d). A schematic of the TNT system fabrication process and simulation results can be found in FIGS. 1 and 2. In contrast to current in vivo transfection technologies (e.g., viruses, conventional tissue bulk electroporation or BEP), in which gene delivery is highly stochastic in nature and could lead to adverse side-effects (e.g., inflammatory response, cell death) (Sen C K et al. Am J Pathol 2015, 185(10): 2629-2640), nanochannel-based delivery enables more ample, benign, instantaneous and dose-controlled reprogramming factor delivery at the single cell level, thus making this a safer and more deterministic approach for in vivo gene transfection and reprogramming.

Figure 6A:
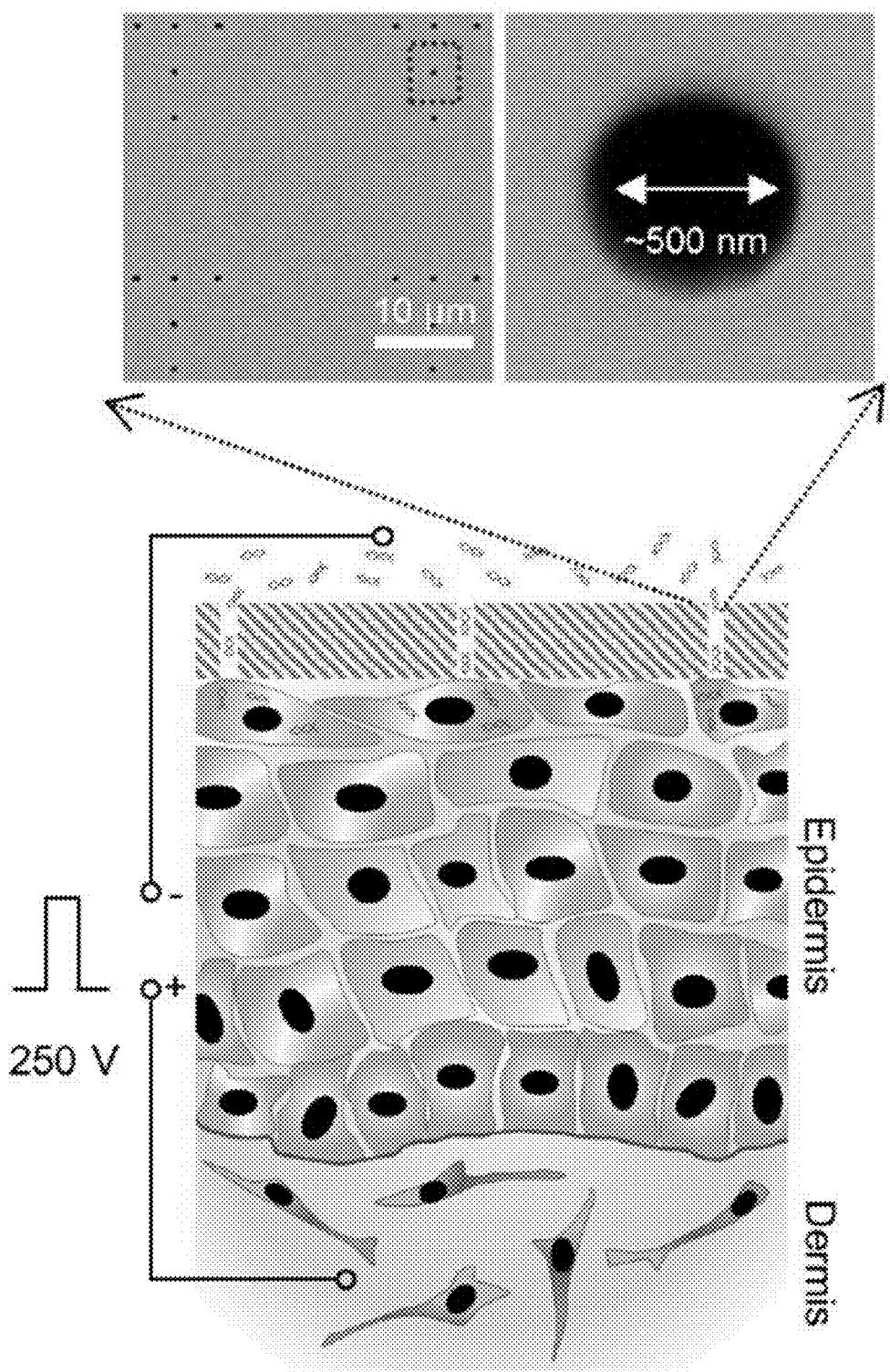
FIGS. 6a-n show TNT mediates enhanced reprogramming factor delivery and propagation beyond the transfection boundary.
Figure 6B:
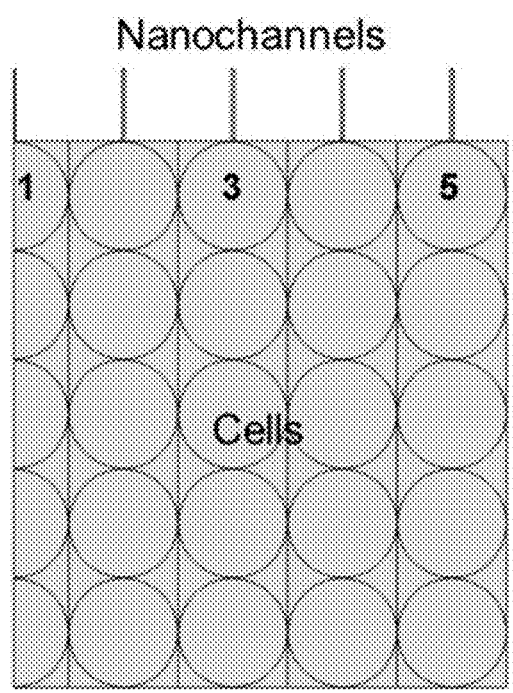
FIG. 6b shows a schematic diagram showing the boundary conditions for simulation purposes.
Figure 6C:
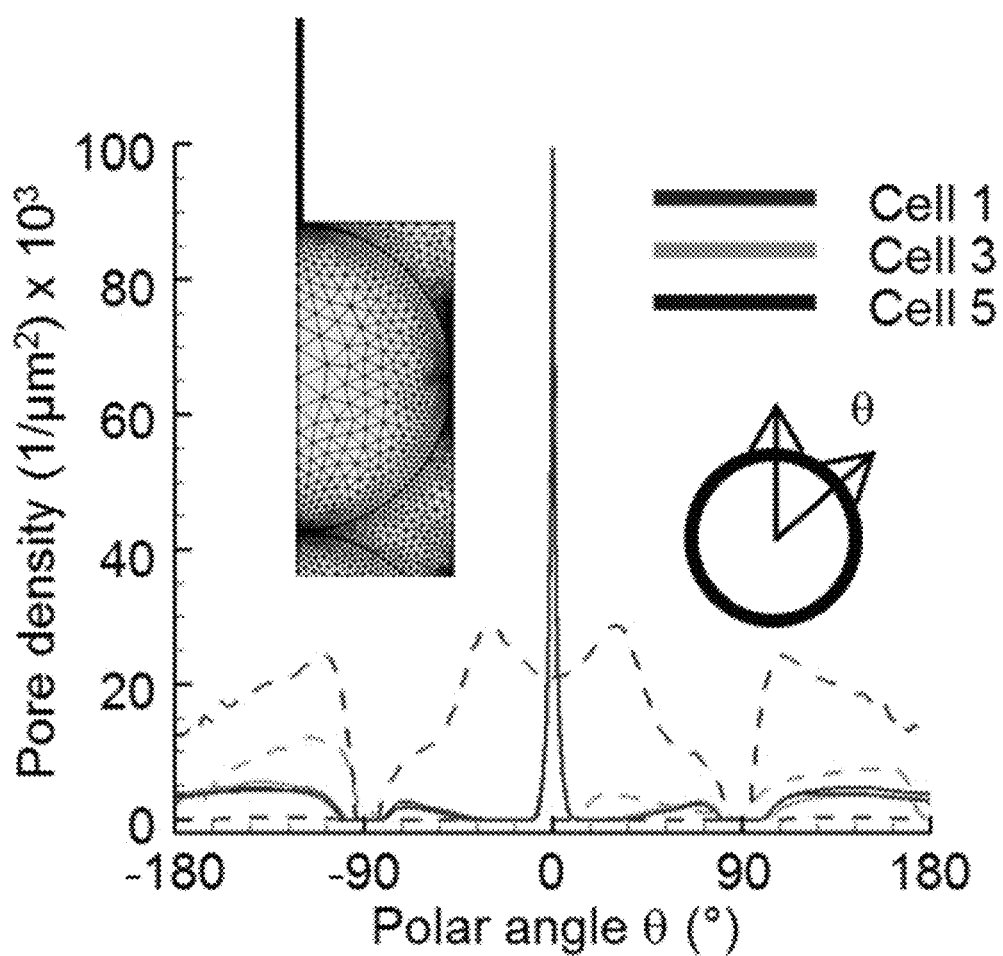
FIG. 6c shows a simulation of the poration profile for different cells undergoing TNT (solid lines) vs. BEP (dashed lines). This plot shows that TNT leads to focused poration, while BEP results in widespread poration.
Figure 6D:
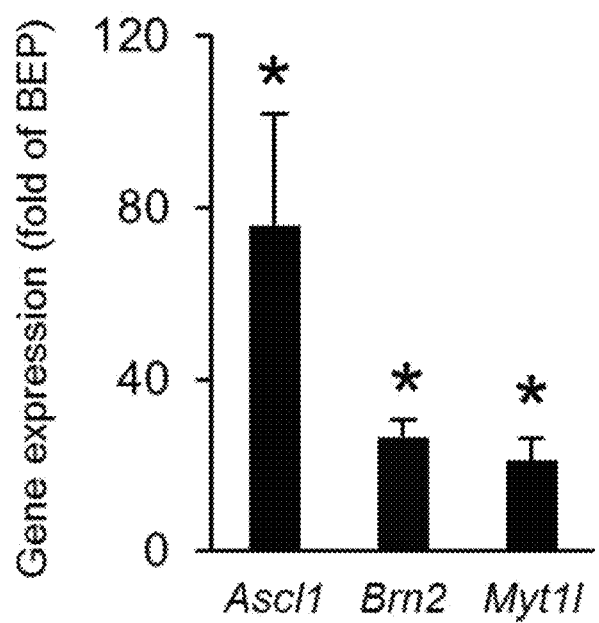
FIG. 6d shows ABM expression results for TNT vs. BEP. TNT resulted in superior ABM expression (t=24 hours)
Figure 6E:
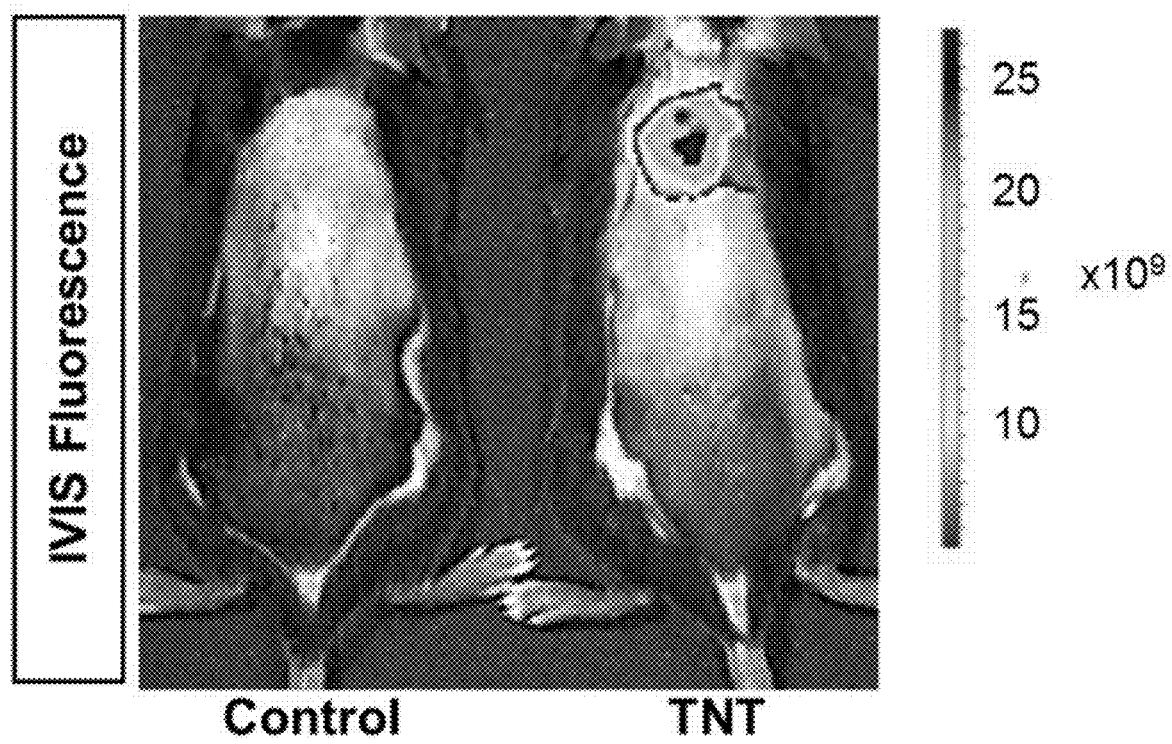
FIG. 6e shows representative IVIS fluorescence and FIG. 6f shows confocal microscopy image of mouse skin after TNT treatment with labeled DNA and the ABM factors, respectively. GFP is the reporter gene in the Ascl1 plasmid.
Figure 6F:
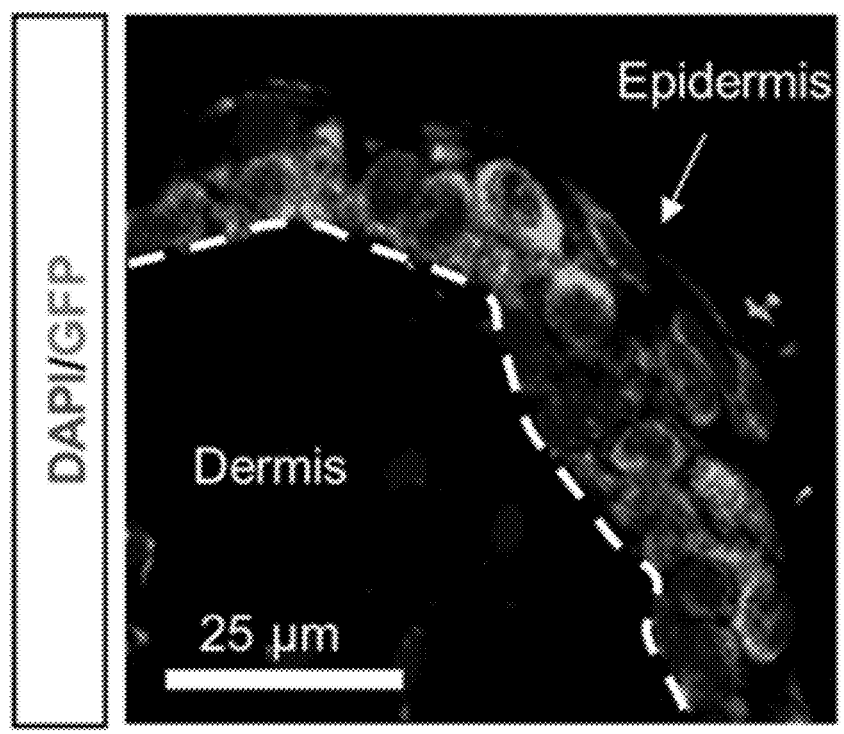
Figures 6G, 6H, 6I:
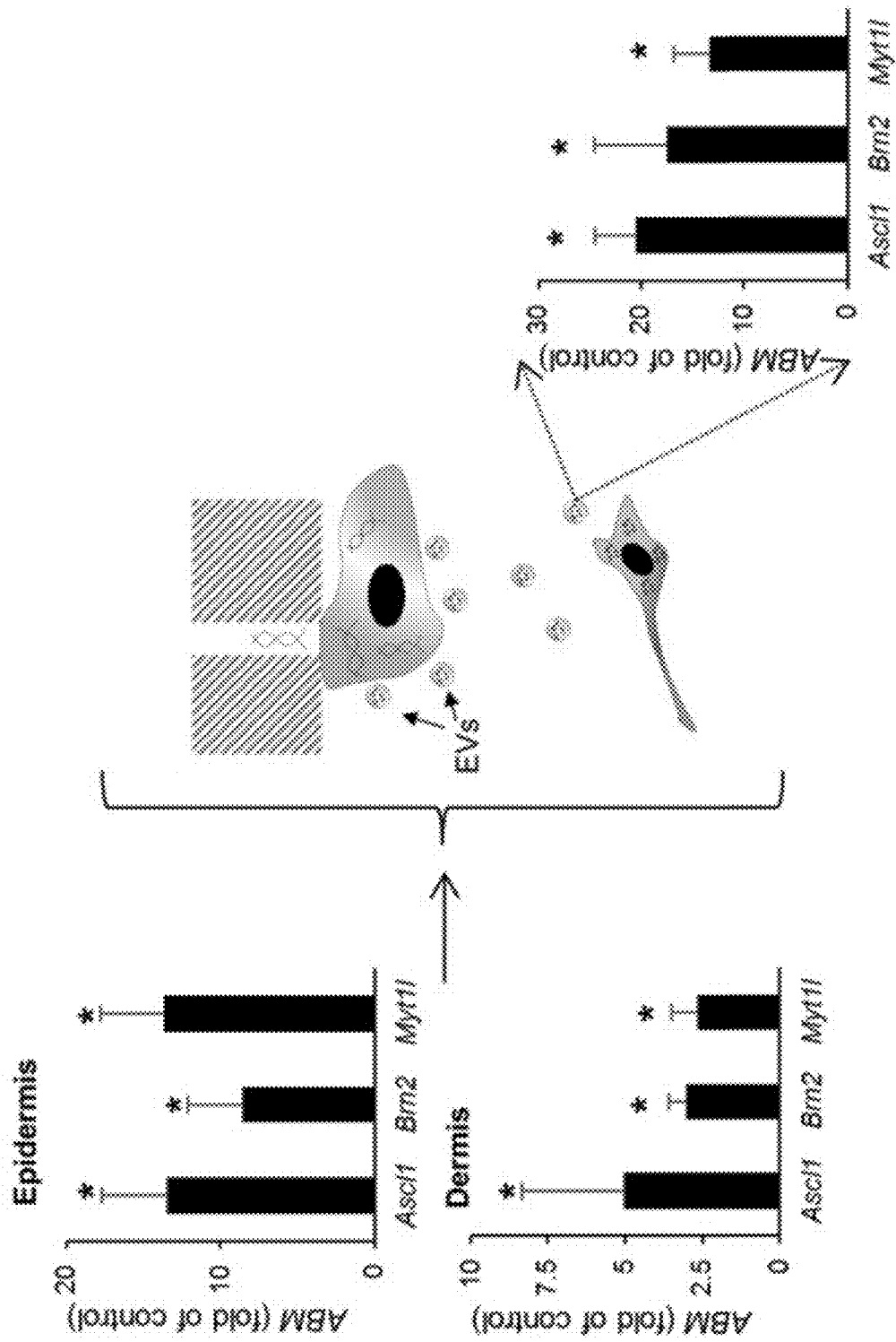
FIG. 6g shows laser Capture Microdissection (LCM) and qRT-PCR results of gene expression in epidermis and dermis (t=24 hours) showing that gene expression propagated beyond the epidermal transfection boundary.
FIG. 6h shows a schematic diagram illustrating the concept of EV-mediated transfection propagation from epidermis to dermis.
FIG. 6i shows qRT-PCR analysis of the EV cargo showing significant loading of ABM mRNAs/cDNAs.
Figure 6J:
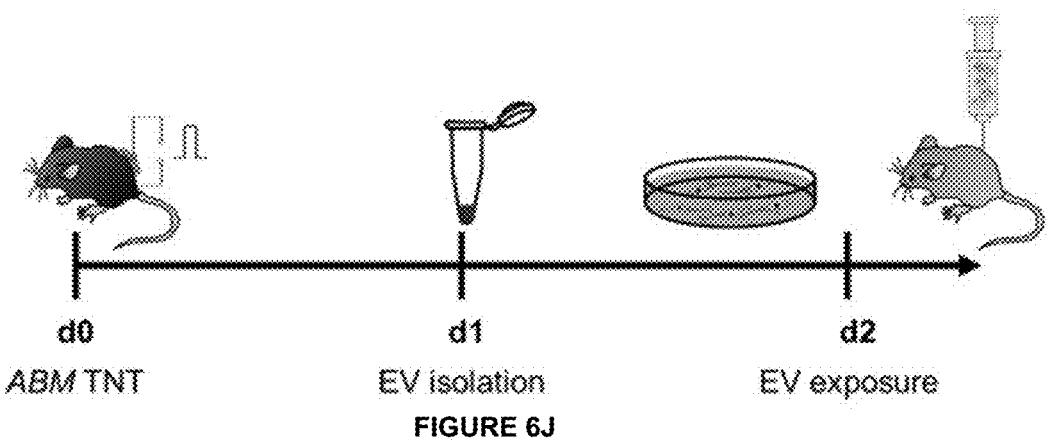
FIG. 6j shows experimental design to confirm whether EVs are a viable vehicle for propagating transfection and reprogramming.
Figure 6K:
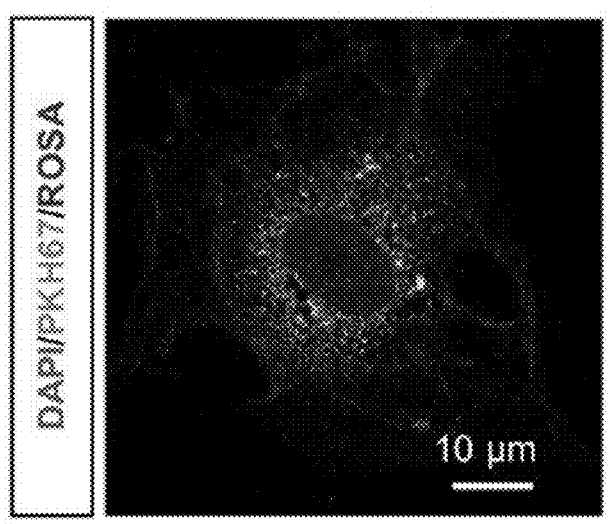
FIG. 6k shows confocal micrograph showing a mouse embryonic fibroblast that has spontaneously internalized the EVs isolated from TNT-treated skin.
Figure 6L:
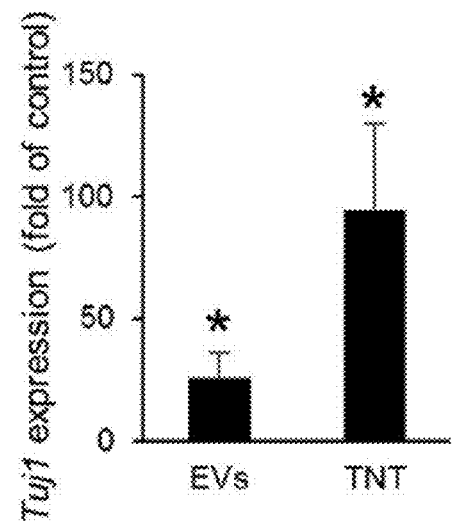
FIG. 6l shows gene expression analysis 14 days after EV injection into naïve mice compared to TNT-based transduction of ABM, Immunostaining results showing increased (m) Tuj1 (week 4)

Experiments with FAM-labeled DNA on C57BL/6 mice established that TNT can deliver cargo into the skin in a rapid (<1 second) and non-invasive/topical manner (FIG. 6e). Next, it was determined that TNT-based topical delivery of reprogramming factors can lead to successful skin reprogramming using a robust model where overexpression of Ascl1/Brn2/Myt1I (ABM) is known to directly reprogram fibroblasts into induced neurons (iNs) in vitro (Vierbuchen et al. Nature 2010, 463(7284): 1035-1041). These findings showed that TNT not only can be used for topical delivery of reprogramming factors (FIG. 6f), but it can also orchestrate a coordinated response that results in reprogramming stimuli propagation (i.e., epidermis to dermis) beyond the initial transfection boundary (i.e., epidermis) (FIG. 6g-i) possibly via dispatch of extracellular vesicles (EVs) rich in target gene mRNAs/cDNAs (FIG. 6h,i) (Valadi et al. Nat Cell Biot 2007, 9(6): 654-659). Exposing naïve cells to ABM-loaded EVs isolated from TNT-treated skin (FIG. 6j-1) established that these EVs can be spontaneously internalized by remote cells (FIG. 6k). Moreover, gene expression analysis indicated that intradermal ABM EV injection triggered changes in the skin consistent with neuronal induction (FIG. 6l), as evidenced by the approximately 25-fold increase in Tuj1 expression compared to control skin. Comparatively, ABM-TNT resulted in an approximately 94-fold increase in Tuj1 expression, which reflects the net effect of direct reprogramming factor injection combined with EV-mediated propagation. The neurotrophic effect of skin-derived ABM-loaded EVs was further confirmed in a middle cerebral artery occlusion (MCAO) stroke mouse model (FIG. 9) (Khanna et al. J Cereb Blood Flow Metab 2013, 33(8): 1197-1206).

Figure 6M:
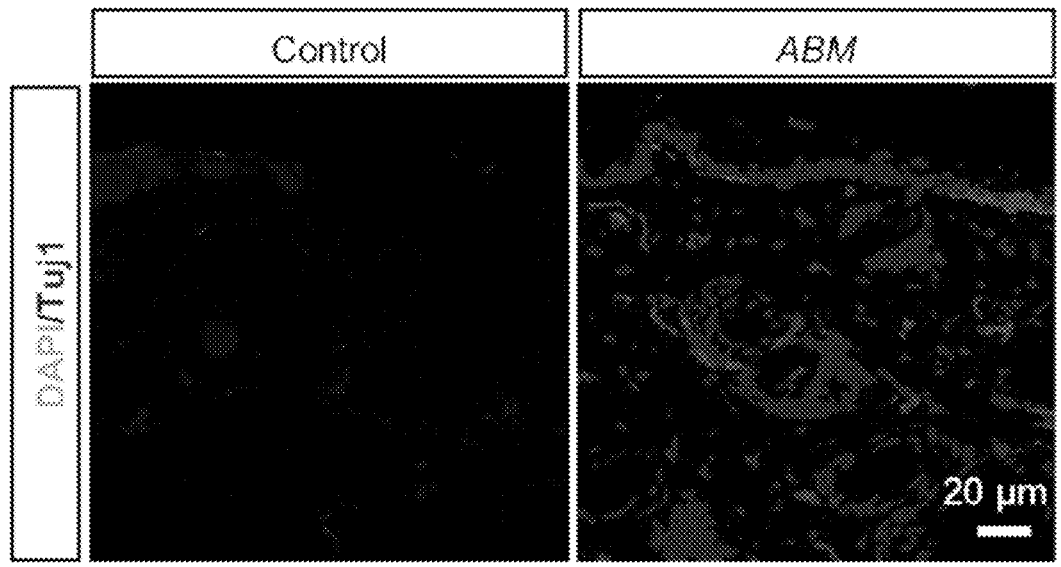
Figure 6N:
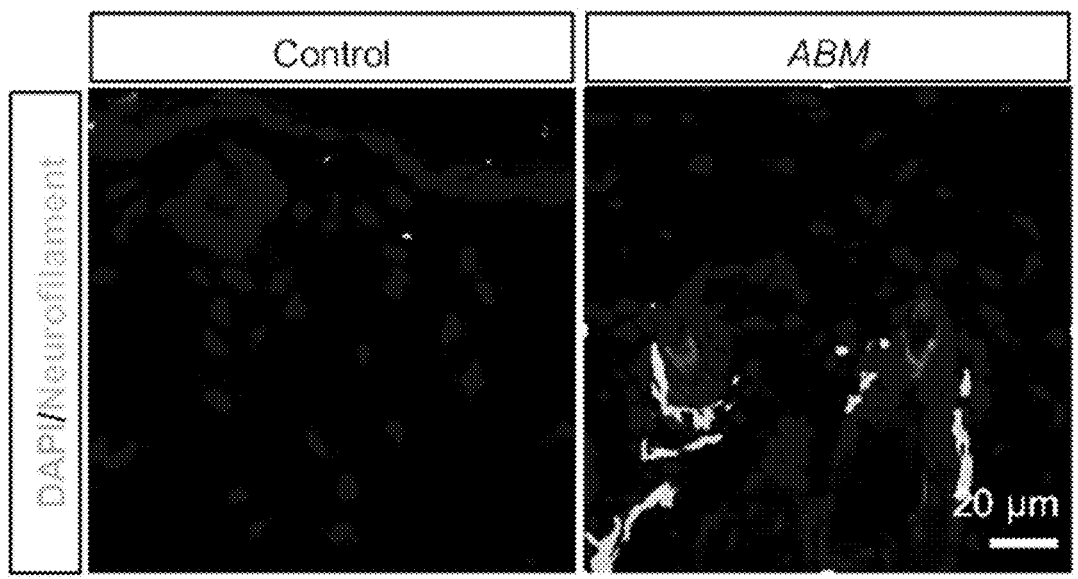
Figures 7A, 7B, 7C, 7D, 7E:
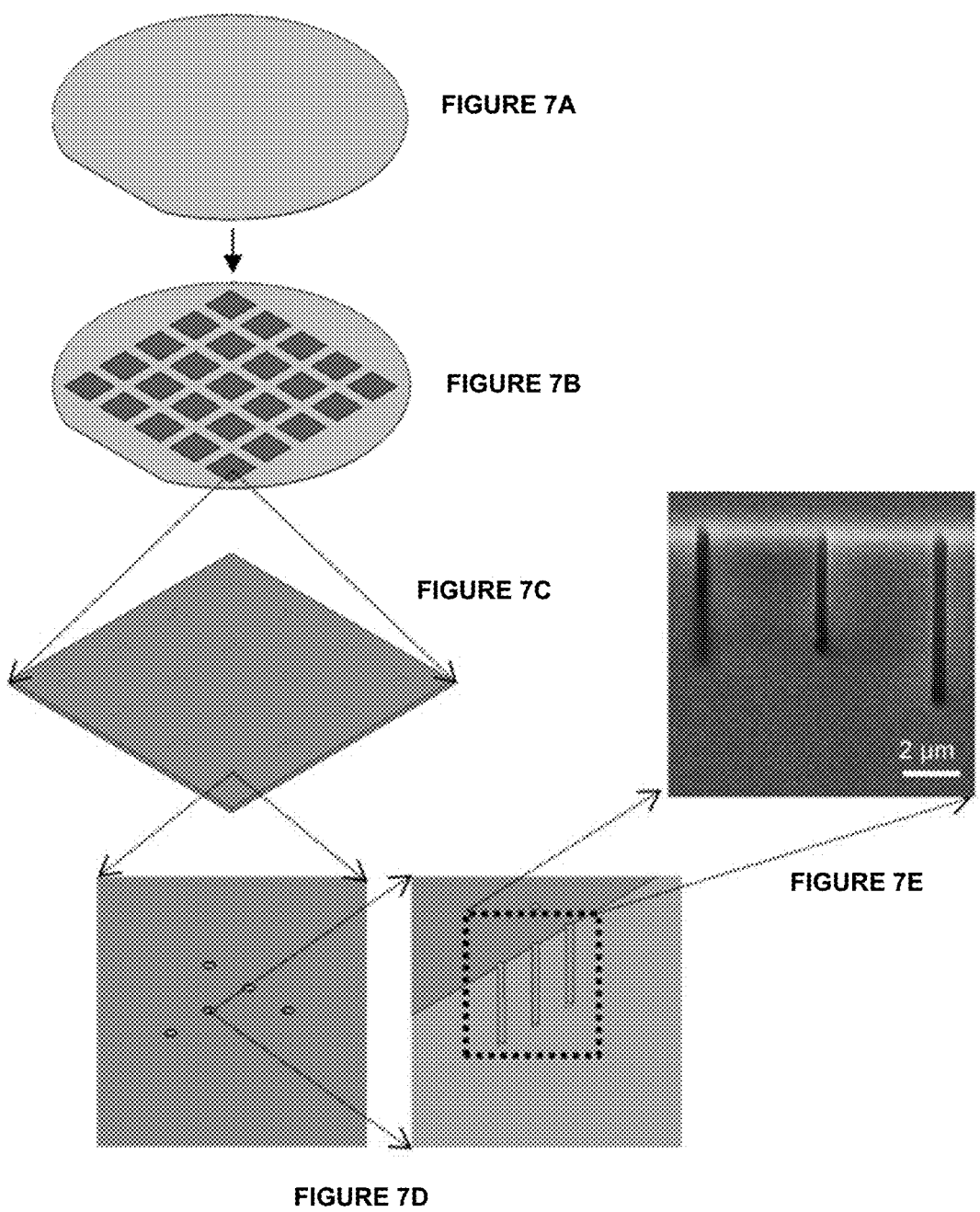
FIGS. 7a-k show TNT platform fabrication and nanochannel array simulation.
Figure 7F:
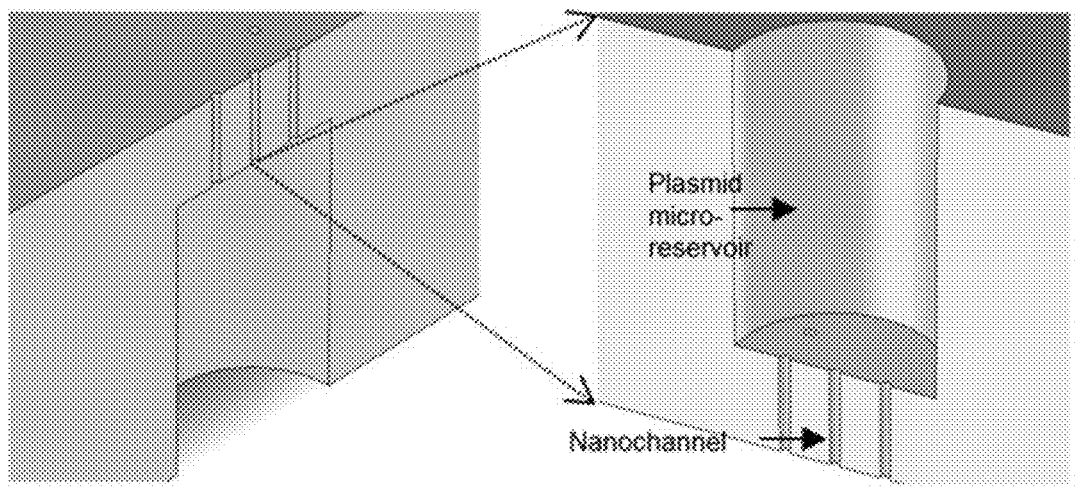
Figure 7G:
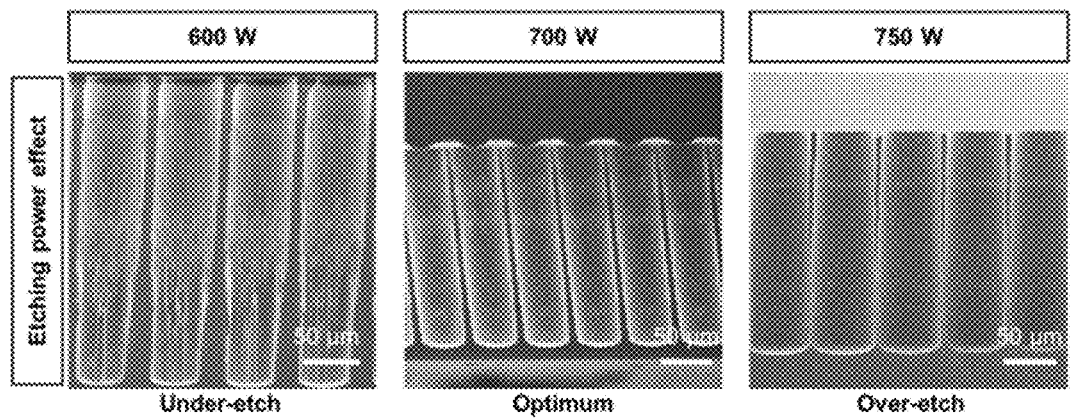
Figure 7H:
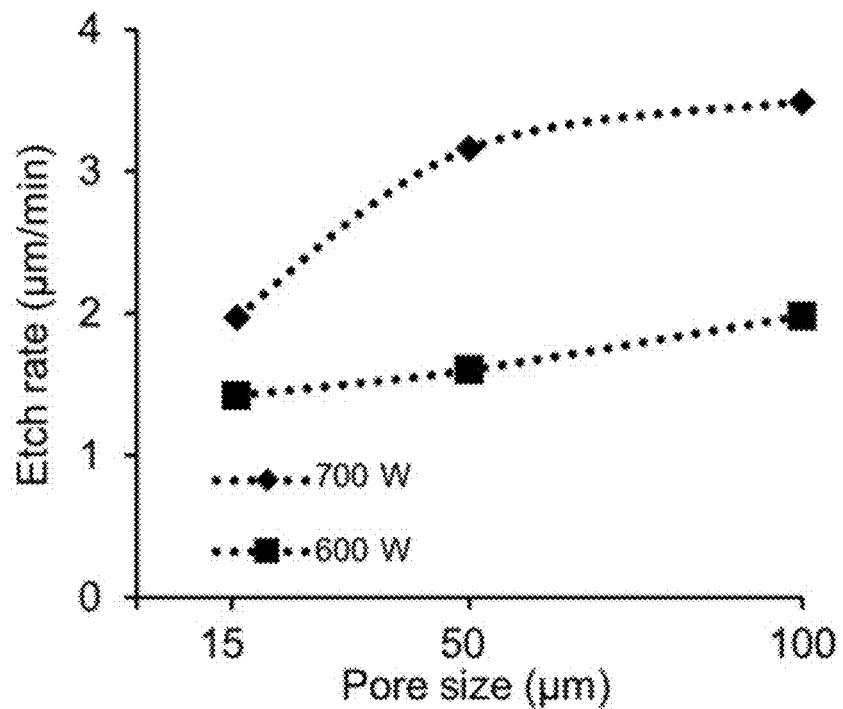
Figure 7I:
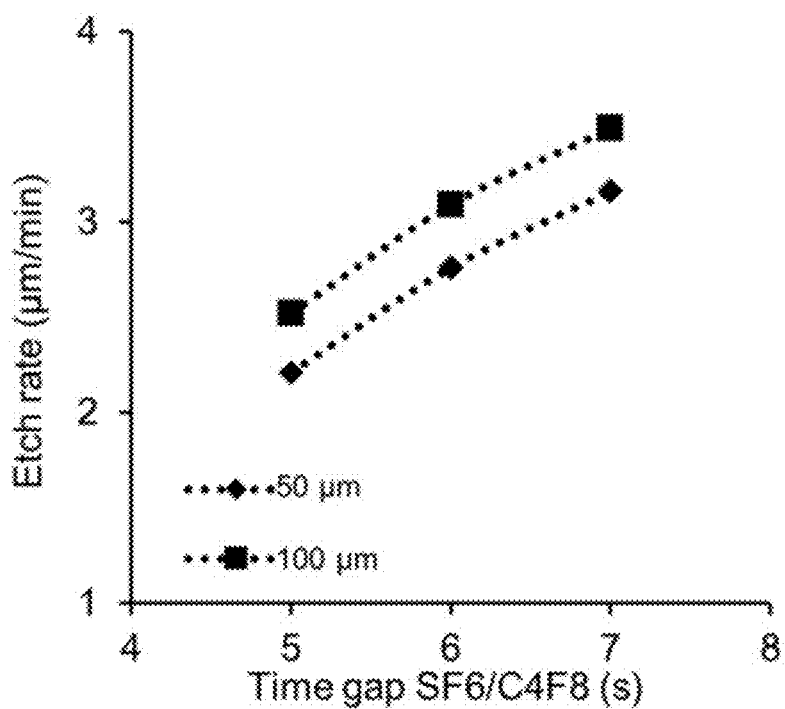
Figure 7J:
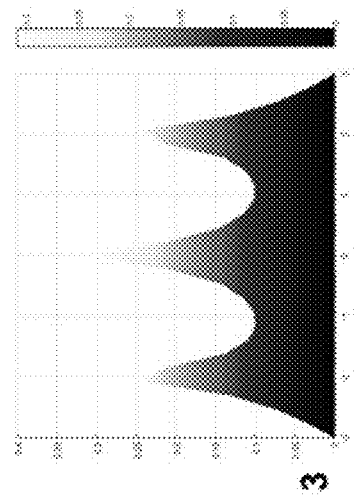
Figure 7J:
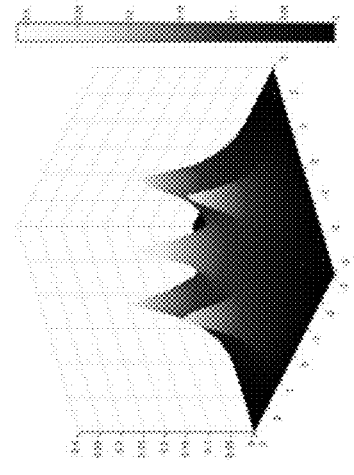
Figure 7J:
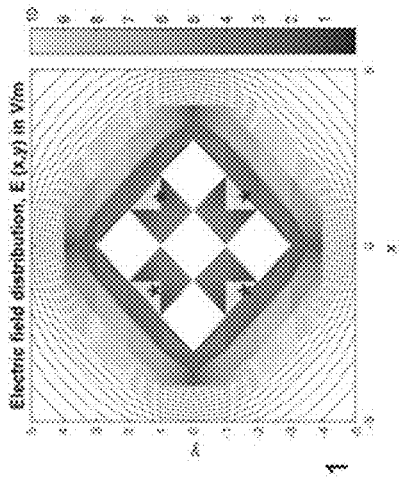
Figure 7K:
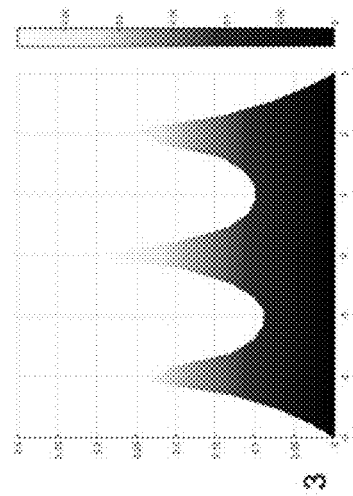
Figure 7K:
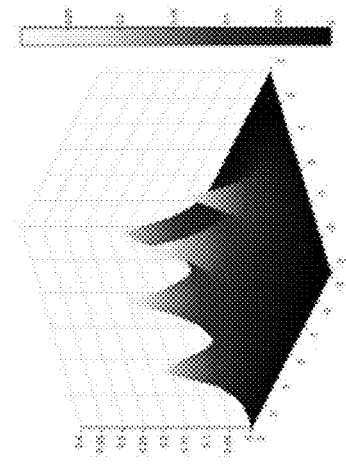
Figure 7K:
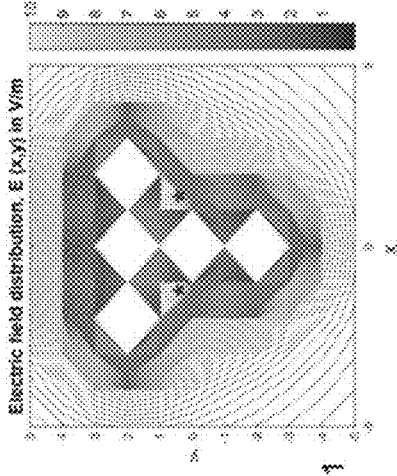
Figure 8A:
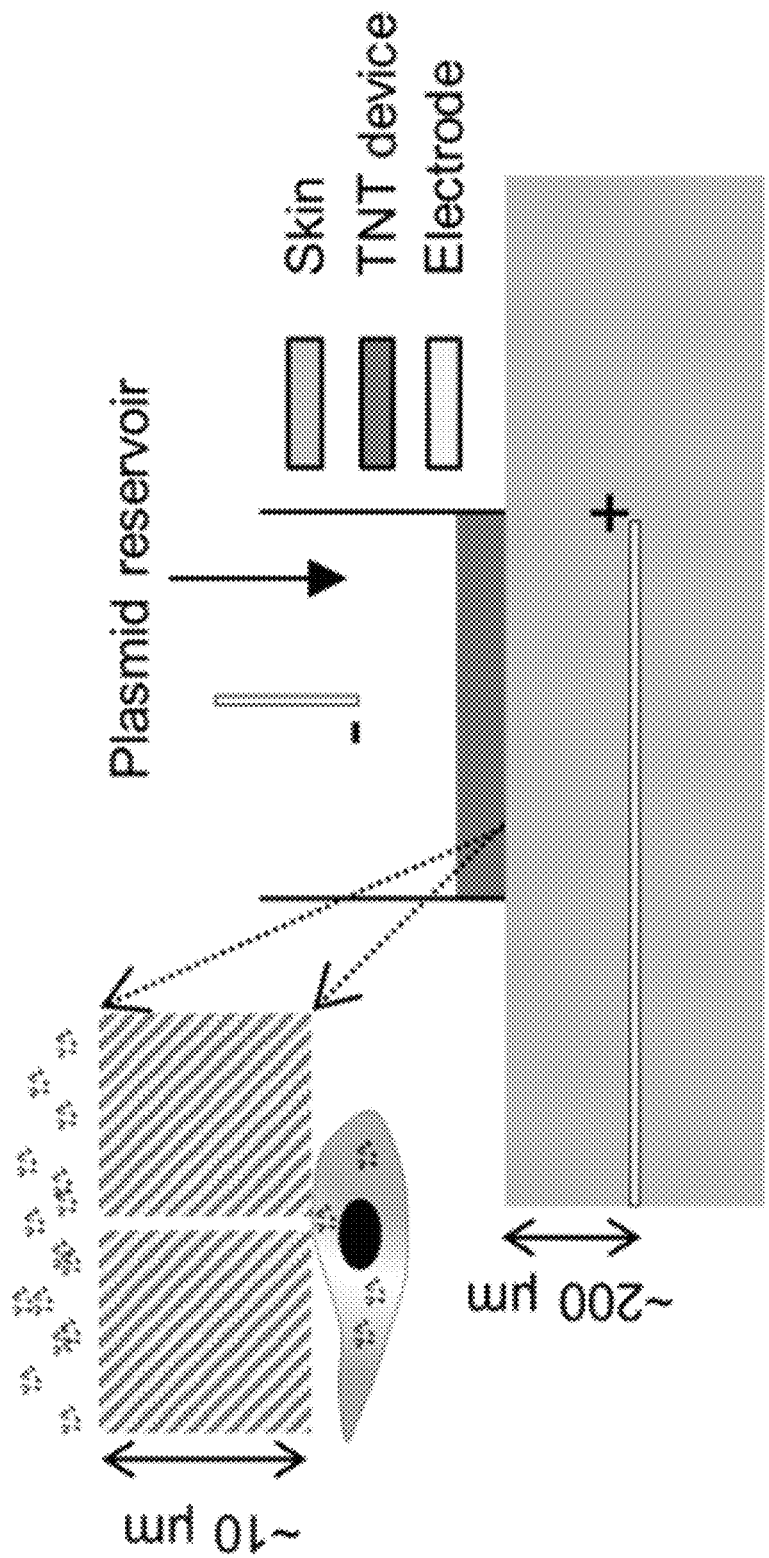
Figure 8D:
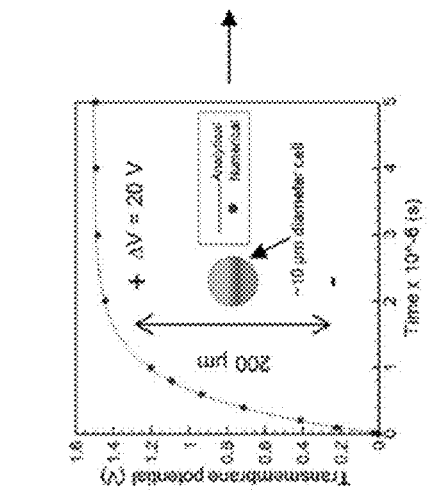
Figure 8E:
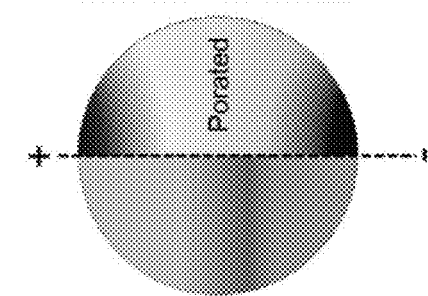
Figure 8F:
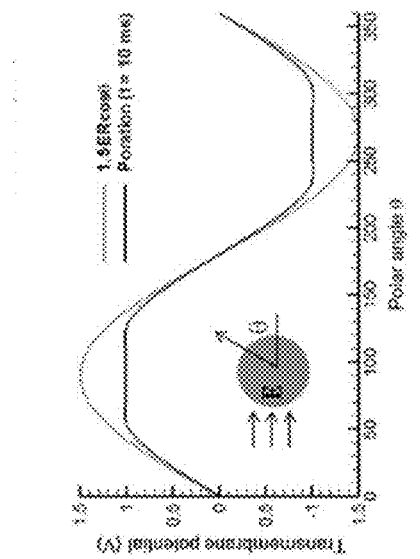
Figure 8G:
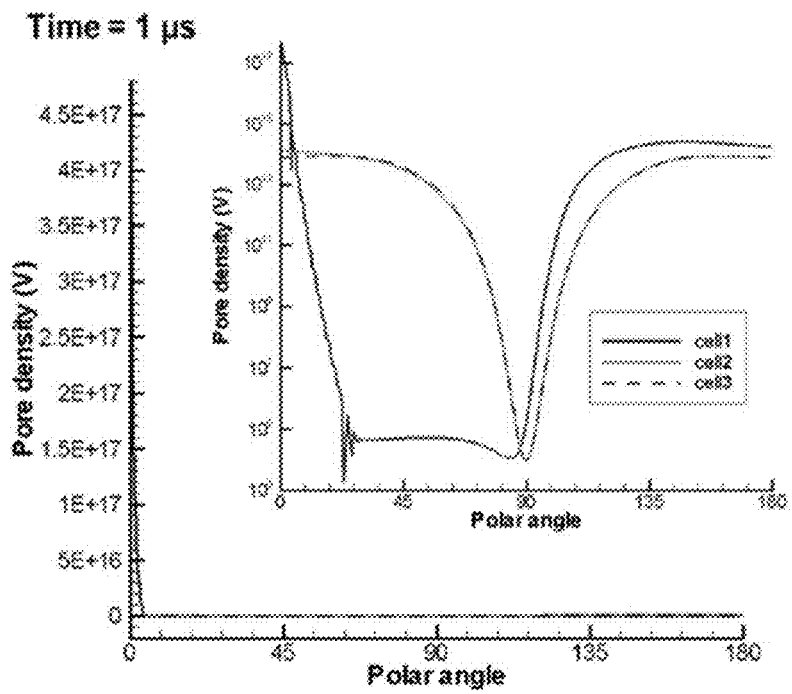
Figure 8H:
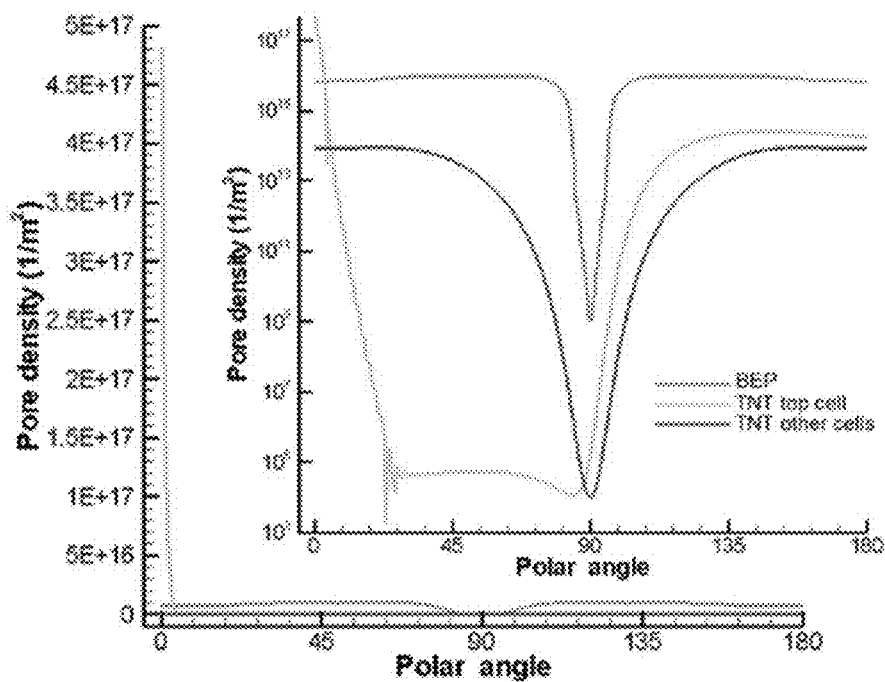
Figure 9A:
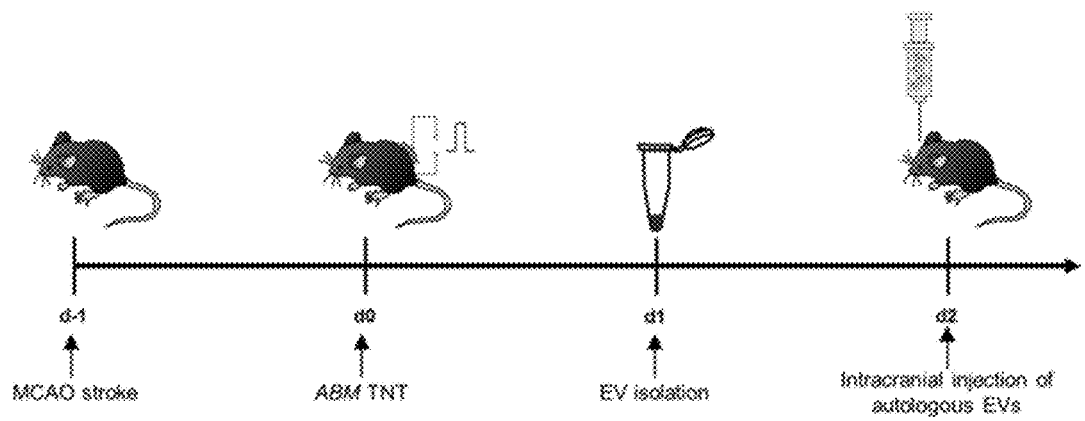
FIGS. 9a-d show autologous ABM-loaded EVs isolated from TNT-treated dorsal skin exhibit neurotrophic-like characteristics in a MCAO stroke mouse (C57BL/6) model.
Figure 9B:
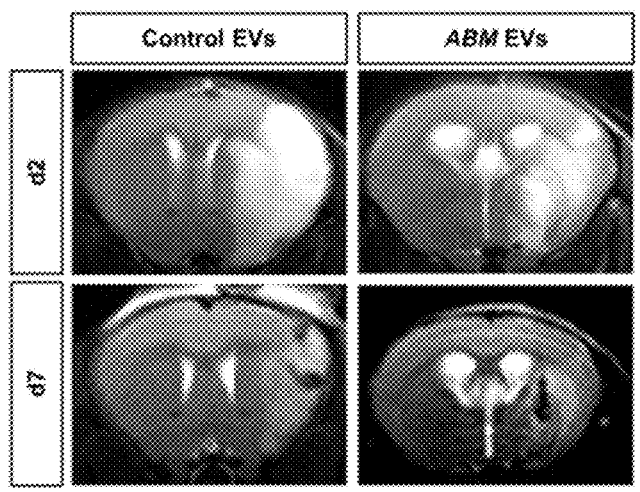
Figure 9C:
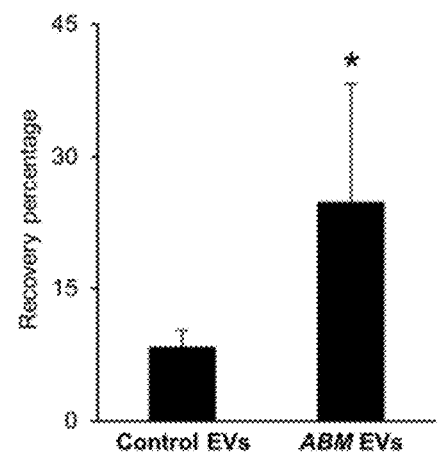
Figure 9D:
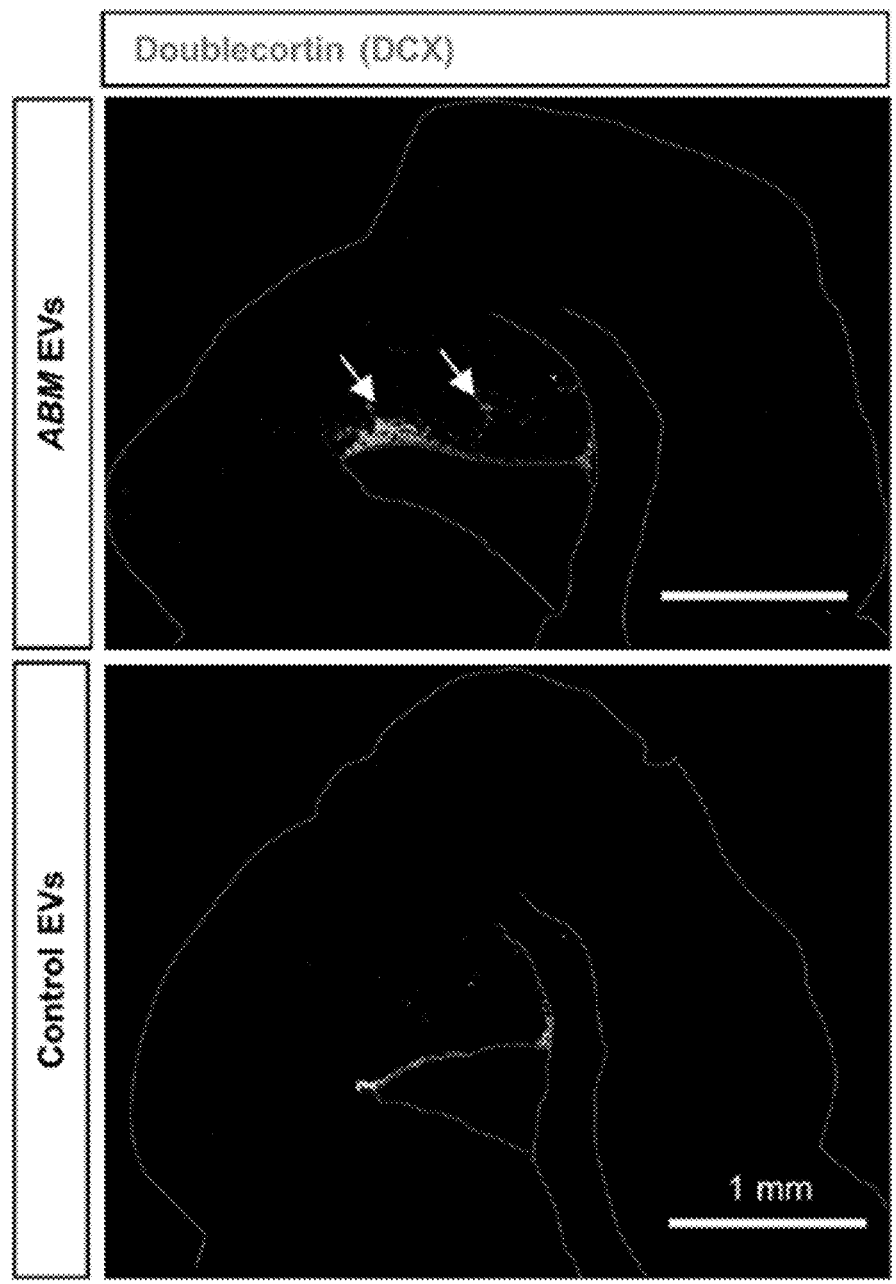
Figure 10A:
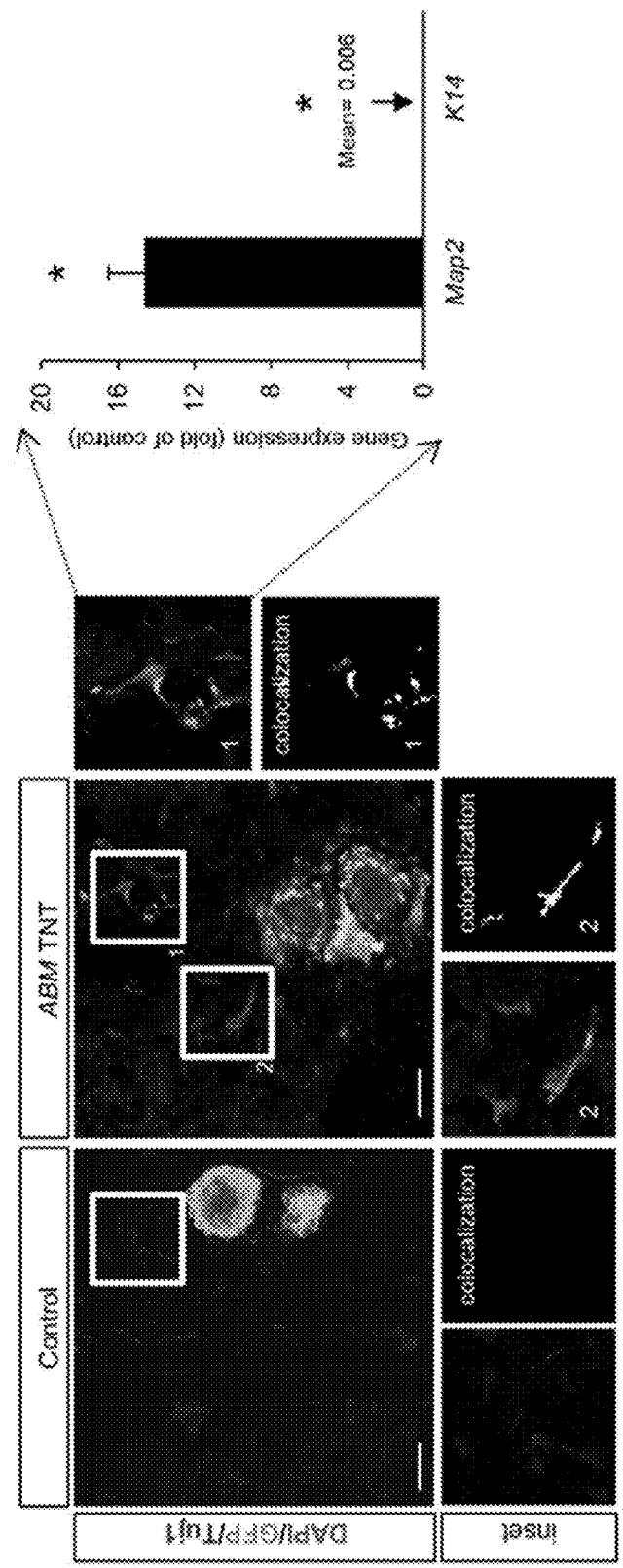
FIGS. 10a-b show iNs in the skin originate from epidermal and dermal sources. Fluorescence micrographs of ABM TNT-treated skin sections from the FIG. 10a shows K14-Cre reporter
Figure 10B:
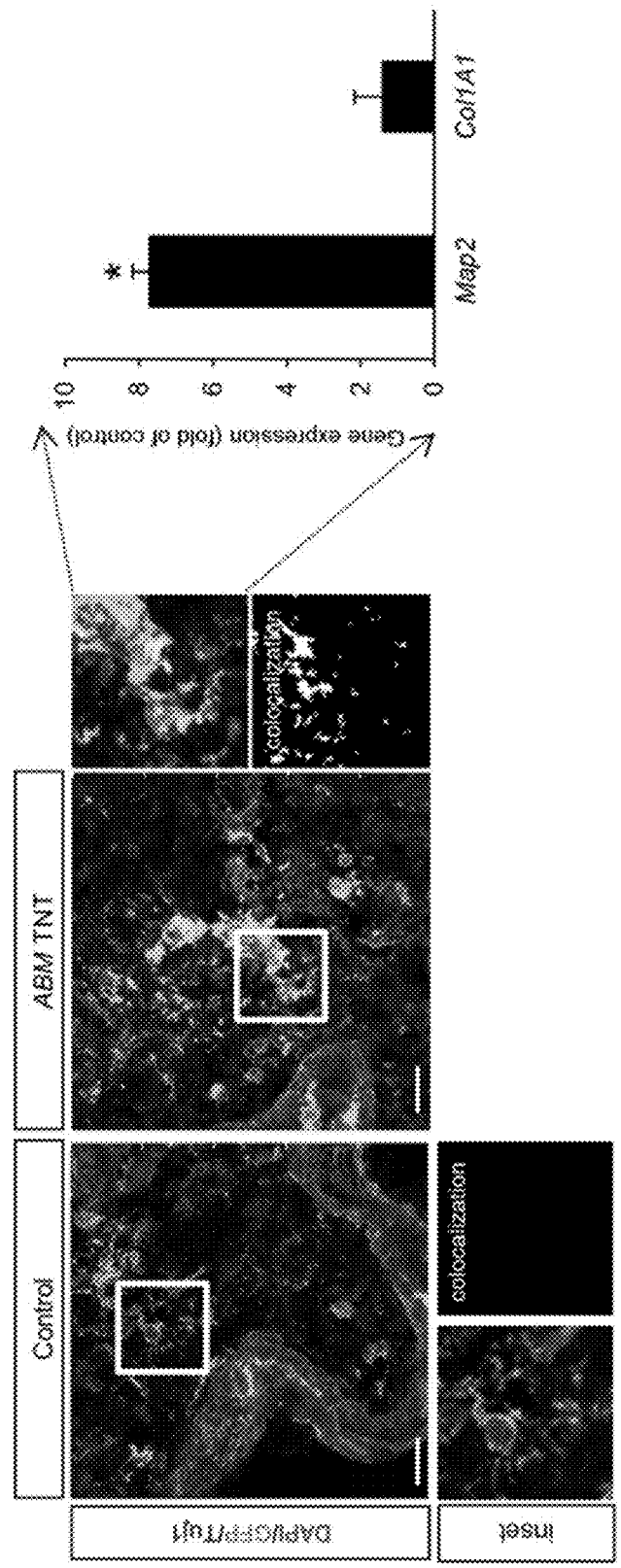
Figure 11:
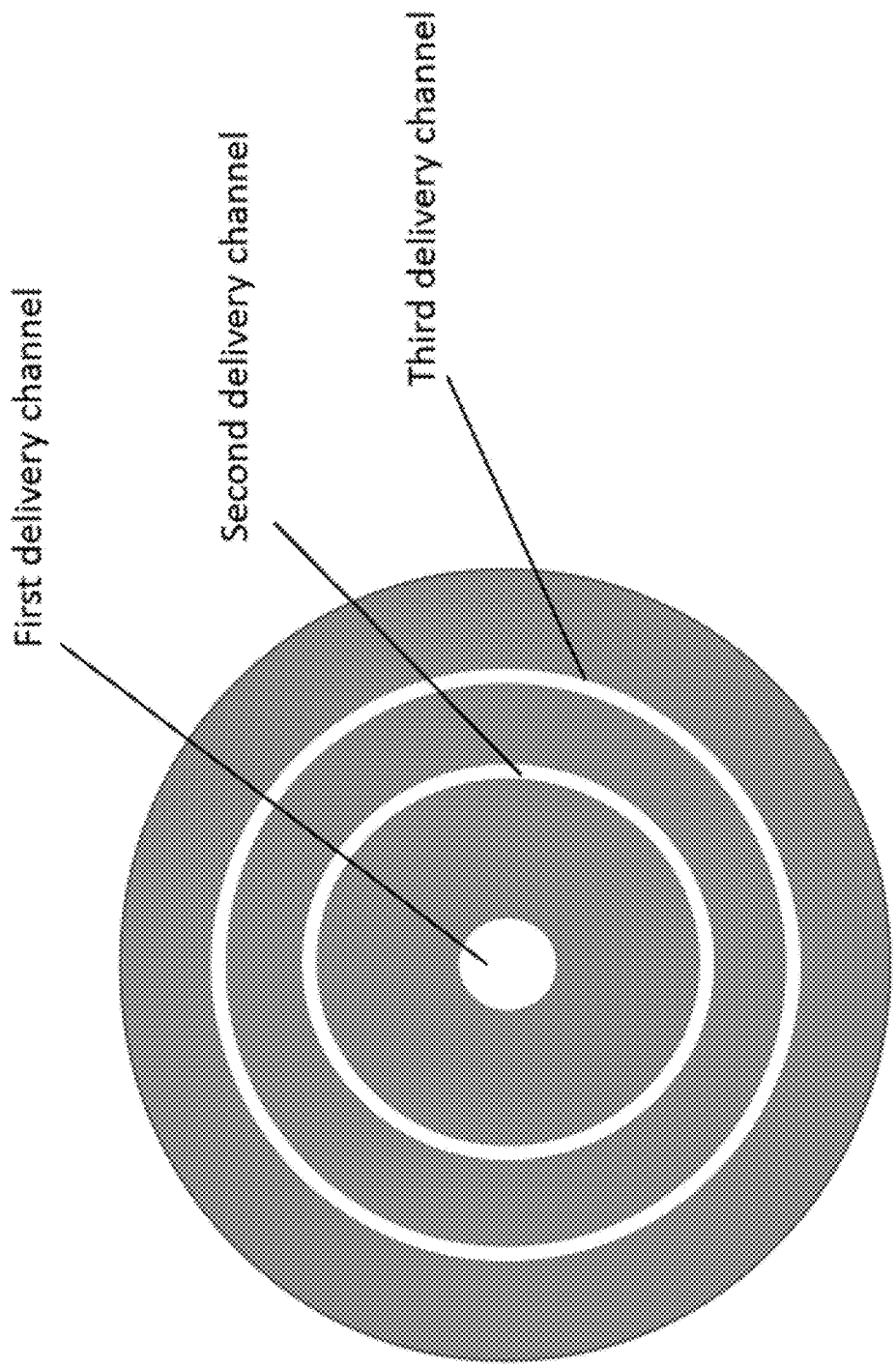
FIG. 11 is illustration of a cross-sectional view of an example microstructure embodiment.
Figure 12:
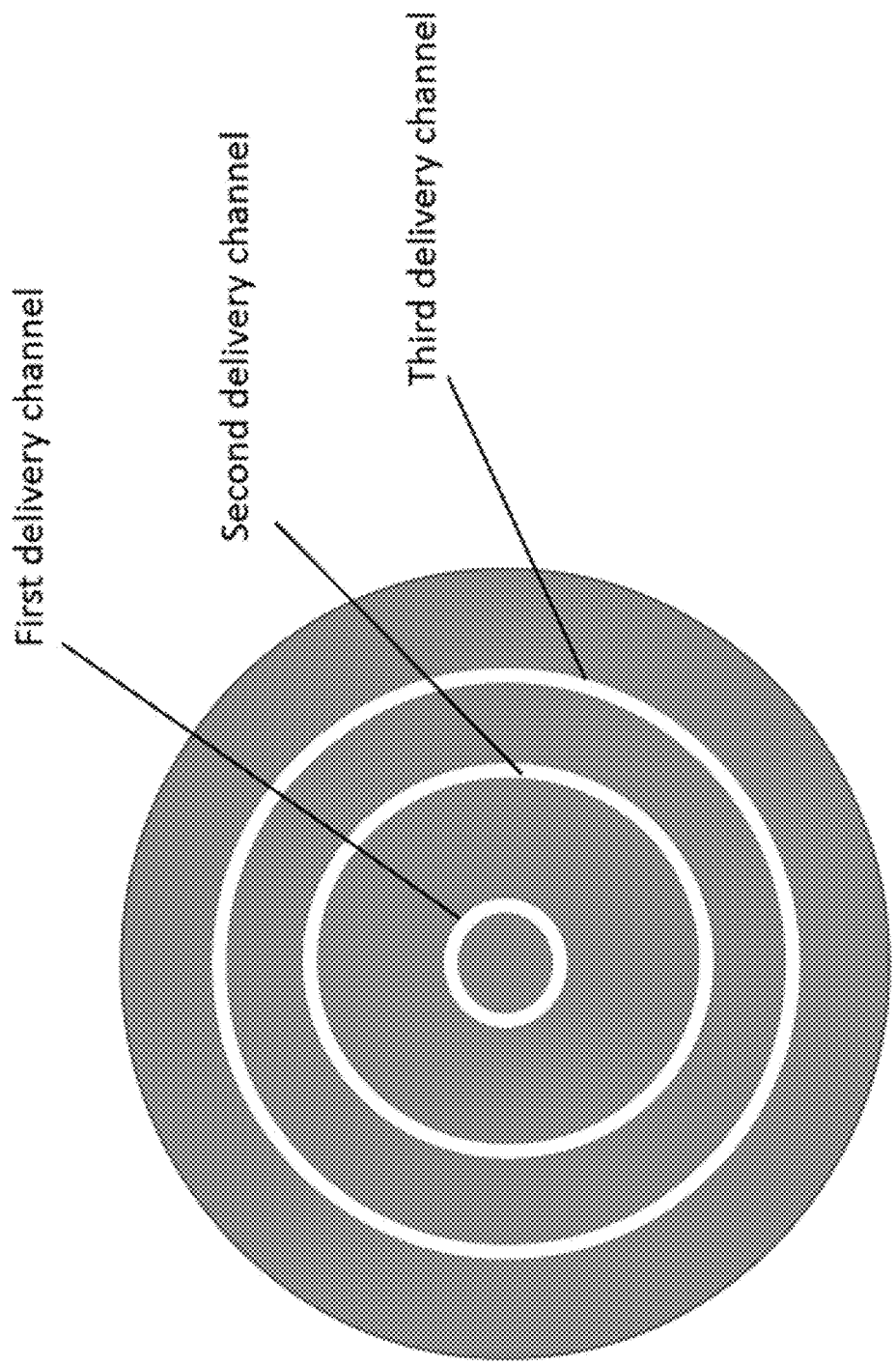
FIG. 12 is illustration of a cross-sectional view of an example microstructure embodiment.
Figure 13:
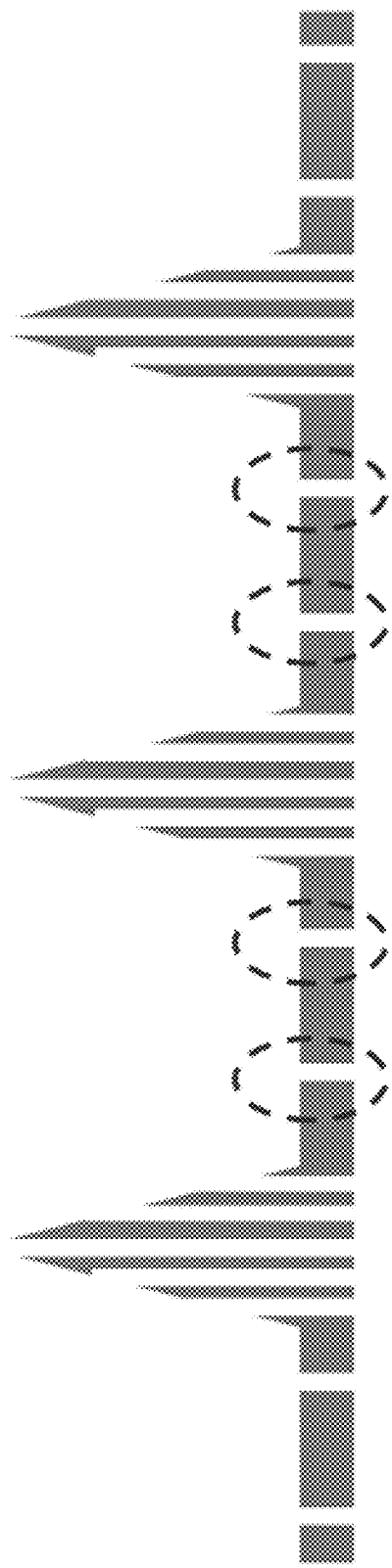
FIG. 13 is illustration of a cross-sectional view of an example microstructure embodiment.
Figure 14A:
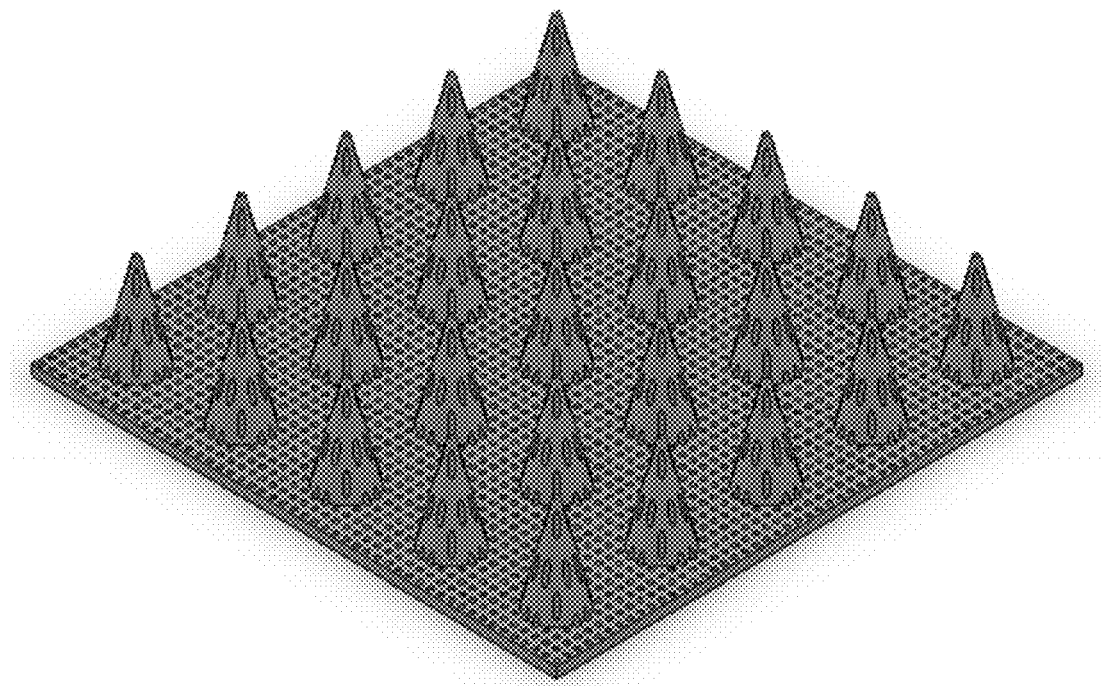
FIGS. 14A-14D show various microstructure array arrangements and embodiments.
Figure 14B:
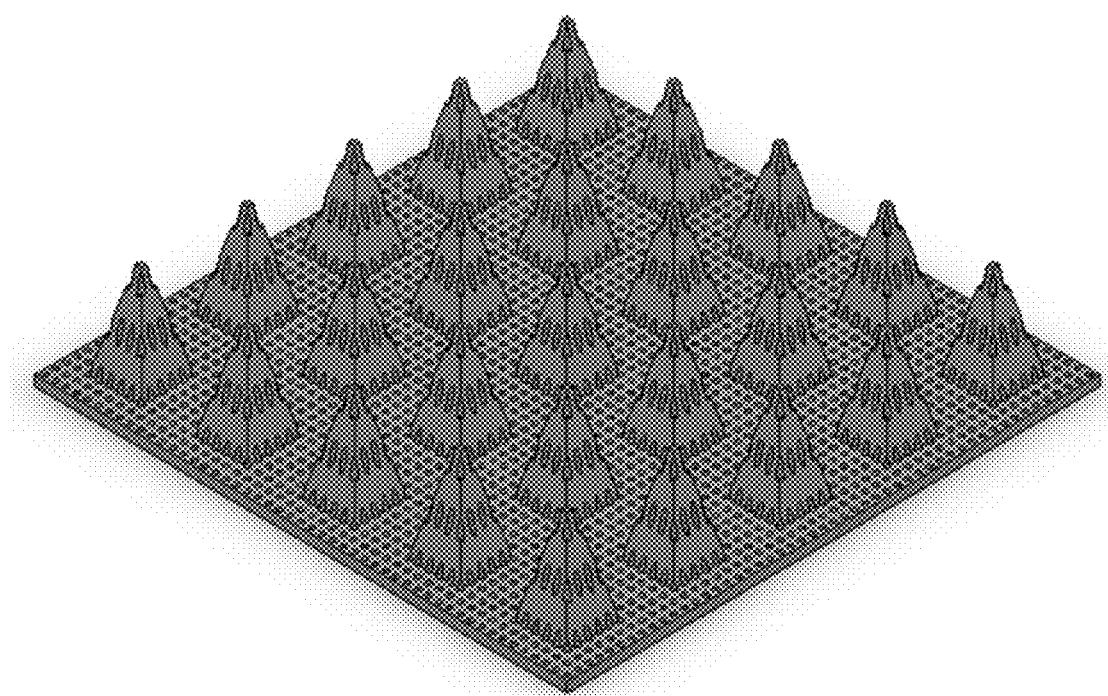
Figure 14C:
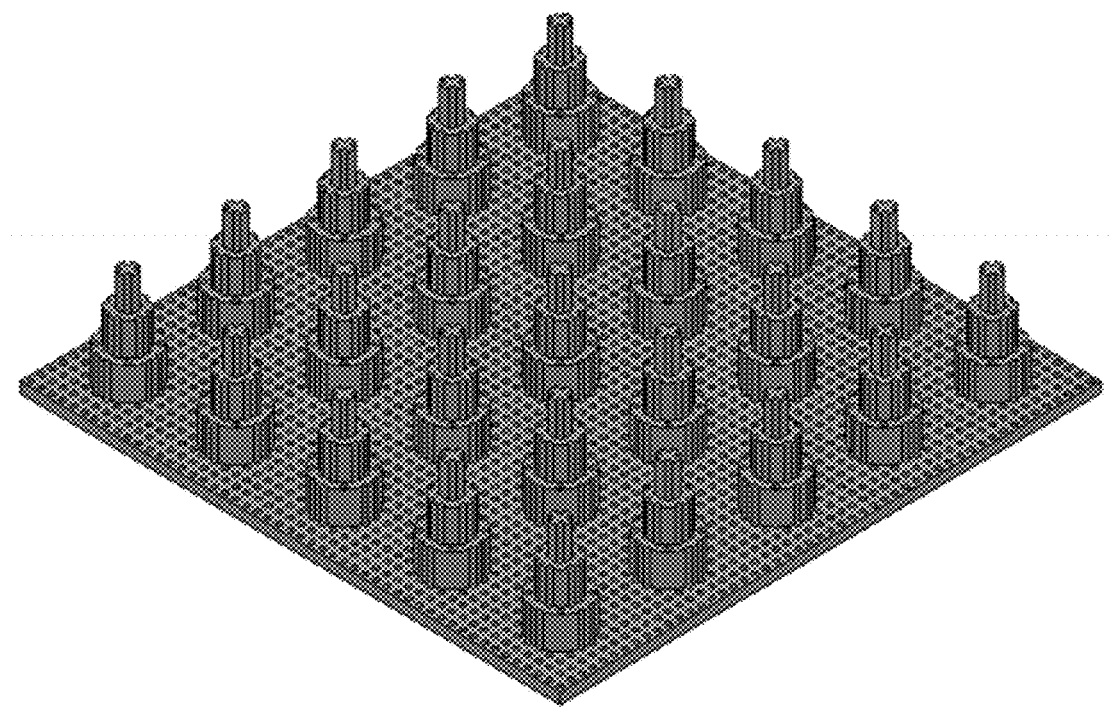
Figure 14D:
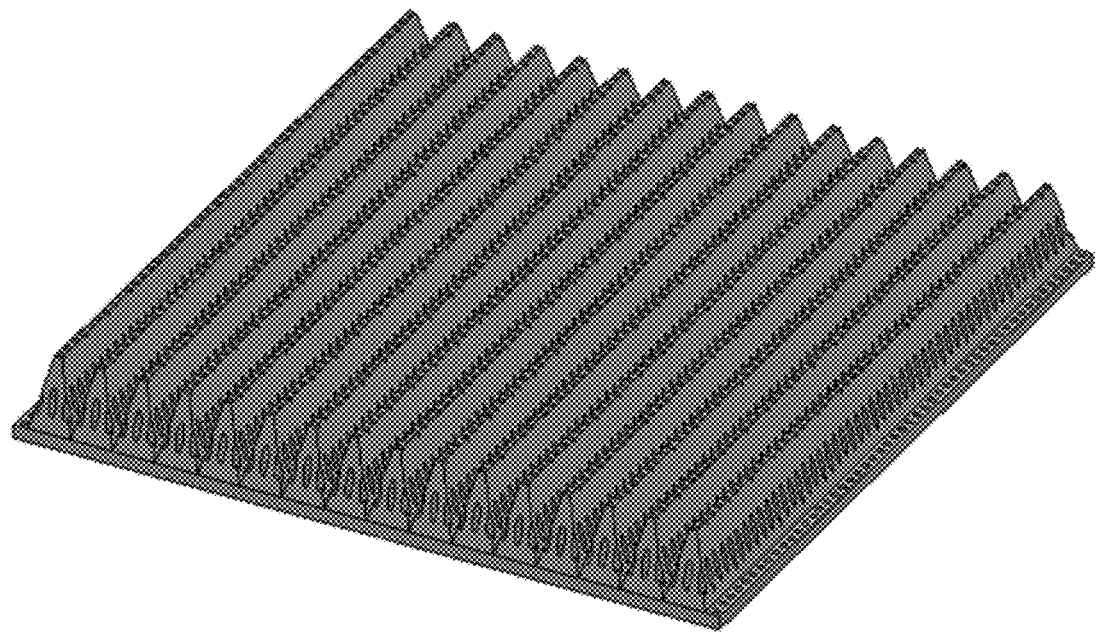
Figure 15A:
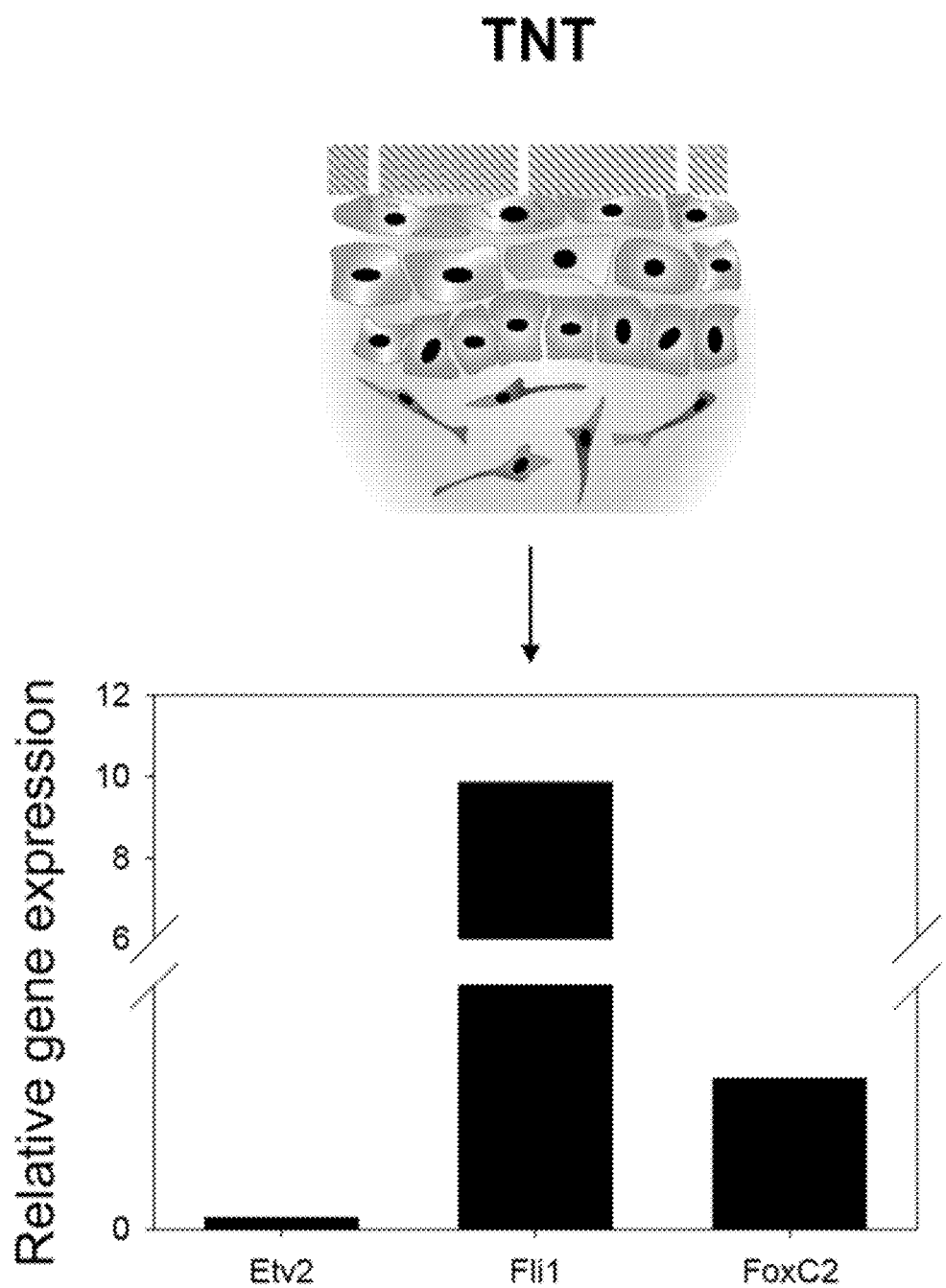
FIGS. 15A and 15B are plots comparing the relative level of gene expression observed upon delivery of example reprogramming factors to tissue using a TNT platform (FIG. 15A) and a DTN platform (FIG. 15B). Significantly higher levels of gene expression were observed in tissue when formulations were administered using the DTN platform.
Figure 15B:
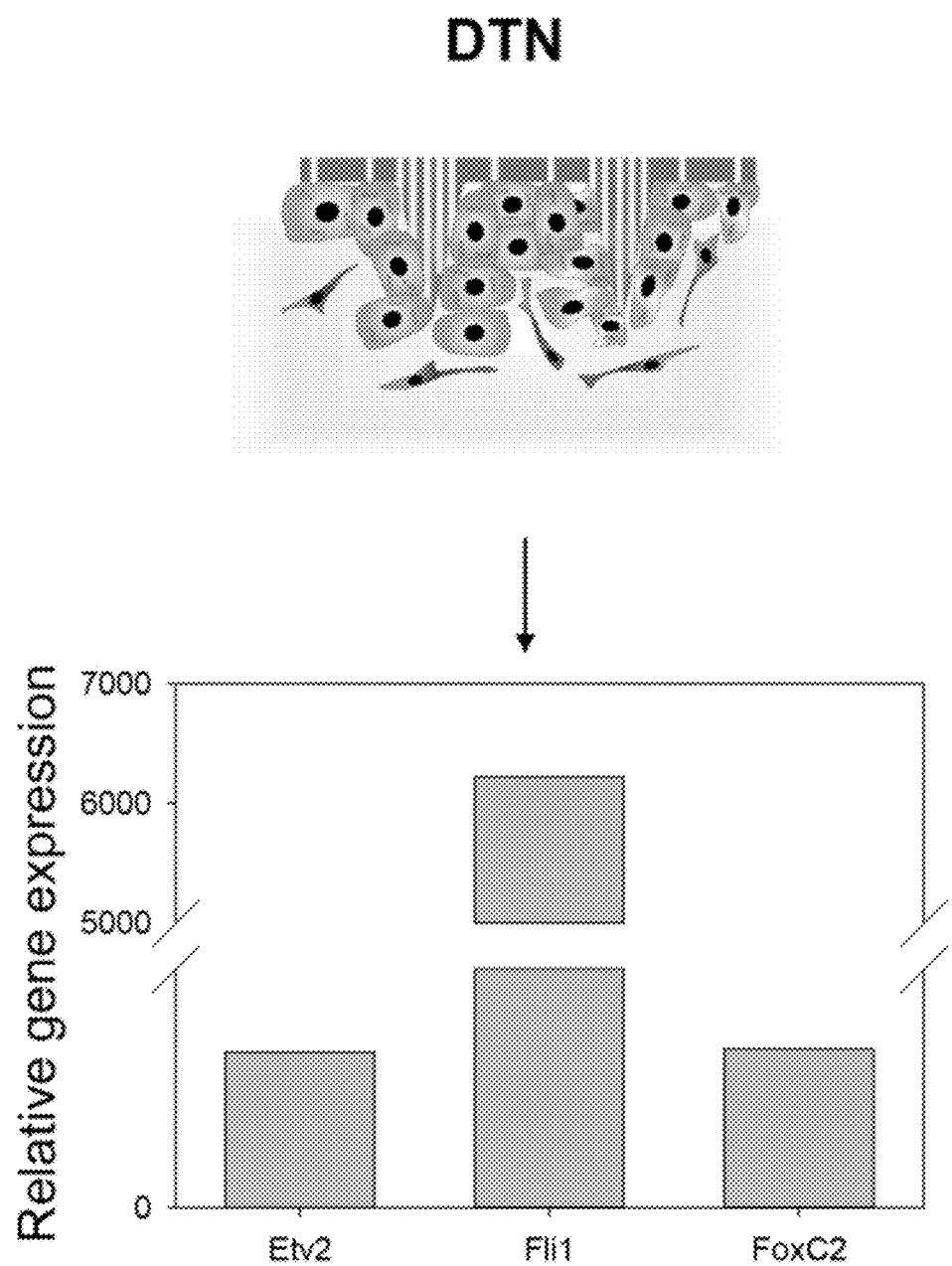
Figure 16:
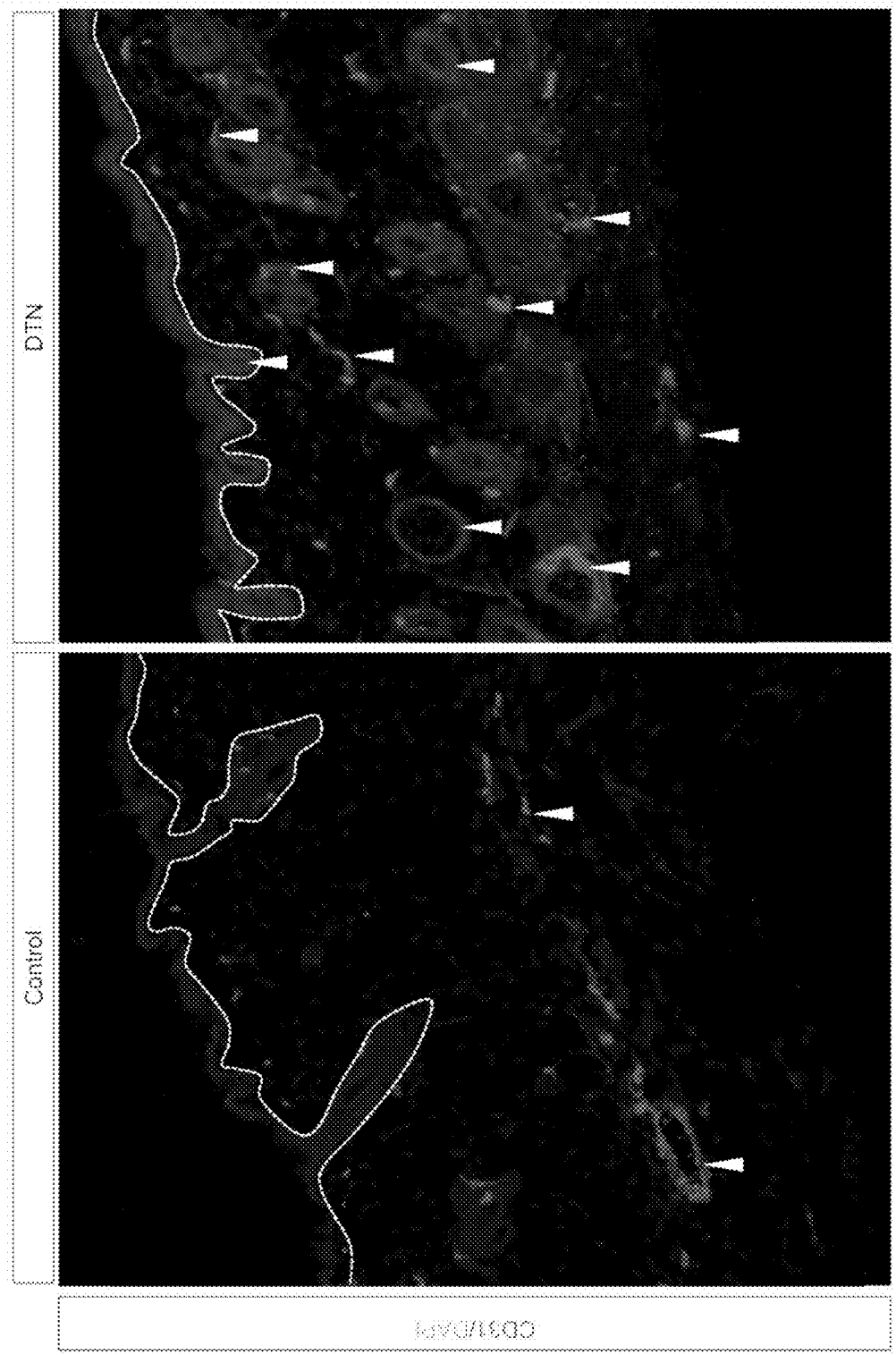
FIG. 16 shows mouse skin tissue reprogramming into an endothelial lineage (i.e., CD31+ cellular structures, stained red) using the DTN platform. A marked increase in CD31 staining across the entire thickness of the tissue section was observed compared to control skin.

Successful skin cell reprogramming was verified by immunofluorescence, which showed increased Tuft and Neurofilament expression overtime (FIG. 6m,n). Lineage tracing experiments with a K14-Cre reporter mouse model confirmed that the newly-induced neurons partly originated from K14+ skin cells (FIG. 10). Hair follicles also consistently showed marked Tuj1 immunoreactivity, suggesting that follicular cells could potentially play a role in the reprogramming process (Hunt et al. Stem Cells 2008, 26(1): 163-172; Higgins et al. J Invest Dermatol 2012, 132(6): 1725-1727). Additional experiments with a CollAI-eGFP mouse model (FIG. 10), where cells with an active CollAI promoter (e.g., dermal fibroblasts) express eGFP, showed a number of Collagen/eGFP+ cells in the dermis in a transition phase to Tuj1+, thus suggesting also a fibroblastic origin for a proportion of the reprogrammed cells in the skin.

Therefore, it has been demonstrated herein that TNT can be used to deliver reprogramming factors into the skin in a rapid, highly effective, and non-invasive manner. Such TNT delivery leads to tailored skin tissue reprogramming, as demonstrated with well-established and newly developed reprogramming models of iNs and iECs, respectively. TNT-induced skin-derived iECs rapidly formed blood vessel networks that successfully anastomosed with the parent circulatory system and restored tissue and limb perfusion in two murine models of injury-induced ischemia. This simple to implement TNT approach, which elicits and propagates powerfully favorable biological responses through a topical one-time treatment that only lasts seconds, can find applications in the development of novel interventional cell-based therapies for a wide variety of applications.

Methods

TNT Platform Fabrication

TNT devices were fabricated from thinned (approximately 200 μm) double-side polished (100) silicon wafers (FIG. 7). Briefly, approximately 1.5 μm thick layers of AZ5214E photoresist were first spin coated on the silicon wafers at approximately 3000 rpm. Nanoscale openings were subsequently patterned on the photoresist using a GCA 6100C stepper. Up to 16 dies of nanoscale opening arrays were patterned per 100-mm wafer. Such openings were then used as etch masks to drill approximately 10 μm deep nanochannels on the silicon surface using deep reactive ion etching (DRIE) (Oxford Plasma Lab 100 system). Optimized etching conditions included SF6 gas: 13 s/100 sccm gas flow/7000 W ICP power/40 W RF power/30 mT APC pressure; C4F8 gas condition: 7 s/100 sccm gas flow/700 W ICP power/10 W RF power/30 mT APC pressure. Microscale reservoirs were then patterned on the back-side of the wafers via contact photolithography and DRIE. Finally, an approximately 50 nm thick insulating/protective layer of silicon nitride was deposited on the TNT platform surface.

Animal Husbandry

C57BL/6 mice were obtained from Harlan Laboratory. B6.129(Cg)-Gt(ROSA)26Sortm4(ACTB-tdTomato,-EGFP) Luo/J mice obtained from Jackson laboratories were bred with K14cre to produce K14cre/Gt(ROSA)26Sortm4 (ACTB-tdTomato-EGFP)Luo/J mice. All mice were male and 8-12 weeks old at the time of the study. Genotyping PCR for ROSAmT/mG mice was conducted using primers oIMR7318-CTC TGC TGC CTC CTG GCT TCT (SEQ ID NO: 1), oIMR7319-CGA GGC GGA TCA CAA GCA ATA (SEQ ID NO: 2) and oIMR7320-TCA ATG GGC GGG GGT CGT T (SEQ ID NO: 3), while K-14 Cre transgene was confirmed using primers oIMRIO84-GCG GTC TGG CAG TAA AAA CTA TC (SEQ ID NO: 4); oIMRIO85-GTG AAA CAG CAT TGC TGT CAC TT (SEQ ID NO: 5). The animals were tagged and grouped randomly using a computer based algorithm.

Mammalian Cell Culture and In Vitro Reprogramming

Primary human adult dermal fibroblasts (ATCC PCS-201-012) were purchased, mycoplasma-free and certified, directly from ATCC. No further cell line authentication was conducted. These cells were expanded in fibroblast basal medium supplemented with fibroblast growth kit-serum-free (ATCC PCS 201-040) and penicillin/streptomycin. E12.5-E14 mouse embryonic fibroblasts (MEFs) were cultured in DMEM/F12 supplemented with 10% fetal bovine serum. Non-viral cell transfection and reprogramming experiments were conducted via 3D Nanochannel Electroporation (NEP). Briefly, the cells were first grown to full confluency overnight on the 3D NEP device. Subsequently, a pulsed electric field was used to deliver cocktail of plasmids (0.05 µg/µl) into the cells consisting of a 1:1:1 mixture of Fli1:Etv2:Foxc2. The cells were then harvested 24 hours after plasmid delivery, placed in EBM-2 basal medium (CC-3156, Lonza) supplemented with EGM-2 MV SingleQuot kit (CC-4147, Lonza), and further processed for additional experiments/measurements.

In Vivo Reprogramming

The areas to be treated were first naired 24-48 hours prior to TNT. The skin was then exfoliated to eliminate the dead/keratin cell layer and expose nucleated cells in the epidermis. The TNT devices were placed directly over the exfoliated skin surface. ABM or EFF plasmid cocktails were loaded in the reservoir at a concentration of 0.05-0.1 µg/µl. A gold-coated electrode (i.e., cathode) was immersed in the plasmid solution, while a 24 G needle counter-electrode (i.e., anode) was inserted intradermally, juxtaposed to the TNT platform surface. A pulsed electrical stimulation (i.e., 10 pulses of 250 V in amplitude and a duration of 10 ms per pulse) was then applied across the electrodes to nanoporate the exposed cell membranes and drive the plasmid cargo into the cells through the nanochannels. ABM plasmids were mixed at a 2:1:1 molar ratio.

MCAO Stroke Surgery and Analysis

Transient focal cerebral ischemia was induced in mice by middle cerebral artery occlusion (MCAO) was achieved by using the intraluminal filament insertion technique previously described (Khanna et al. J Cereb Blood Flow Metab 2013, 33(8): 1197-1206). MRI images were used to determine infarct size as a percentage of the contralateral hemisphere after correcting for edema.

Hindlimb Ischemia Surgery

Unilateral hind-limb ischemia was induced via occlusion and subsequent transection of the femoral artery followed by transection (Limbourg et al. Nat Protoc 2009, 4(12): 1737-1746). Briefly, 8-10 week mice were anesthetized with 1-3% isoflurane, placed supine under a stereomicroscope (Zeiss OPMI) on a heated pad. The femoral artery was exposed and separated from the femoral vein through an approximately 1 cm incision. Proximal and distal end occlusion were induced with 7-0 silk suture, which was then followed by complete transaction of the artery. Finally, a single dose of buprenorphine was administered subcutaneously to control pain. Laser speckle imaging (MoorLDI-Mark 2) was conducted 2 hours post-surgery to confirm successful blood flow occlusion.

Isolation of Extracellular Vesicles (EVs)

EVs were isolated from 12 mm diameter skin biopsies that were collected in OCT blocks and stored frozen for later use. Briefly, the blocks were thawed and washed with phosphate buffer saline (PBS) to eliminate the OCT. Following removal of the fat tissue with a scalpel, the skin tissue was minced into approximately 1 mm pieces and homogenized with a micro-grinder in PBS. After centrifugation at 3000 g, an Exoquick kit (System Biosciences) was used at a 1:5 ratio (Exoquick:supernatant) to isolate EVs from the supernatant for 12 hours at 4° C. EVs were precipitated via centrifugation at 1500 g for 30 min. Total RNA was then extracted from pellet using the mirvana kit (Life technologies) following the recommendations provided by the manufacturer.

DNA Plasmid Preparation

ABM and EFF plasmids were prepared using plasmid DNA purification kit (Qiagen Maxi-prep, catalogue number 12161, and Clontech Nucleobond catalogue number 740410). DNA concentrations were obtained from a Nanodrop 2000c Spectrophotemeter (Thermoscientific). A list of plasmid DNA constructs and their original sources can be found Table 1.

TABLE 1

Plasmid cDNA

| Construct Name | Gene Insert | Plasmid Backbone |
| --- | --- | --- |
| Brn2-RFP | Brn2 | pCAGGs |
| Myt1l-CFP | Myt1l | pCAGGs |
| Ascl1-GFP | Ascl1 | pCAGGs |
| pIRES-ER71(HA)3 | Etsvp71 (ER71) | pIRES-hrGFP-2a |
| pAd -HA-Fli1-IRES-hrGFP | HA-Fli1 | pAd-IRES-GFP |
| mFoxc2 | mFoxc2 | pCDNA3.0 |

LCM was performed using a laser microdissection system from PALM Technologies (Bernreid, Germany). Specific regions of tissue sections, identified based on morphology and/or immunostaining, were cut and captured under a 20× ocular lens. The samples were catapulted into 25 µl of cell direct lysis extraction buffer (Invitrogen). Approximately 1,000,000 µm² of tissue area was captured into each cap and the lysate was then stored at −80° C. for further processing. qRT-PCR of the LCM samples were performed from cell direct lysis buffer following manufacture's instruction. A list of primers can be found in Table 2.

TABLE 2

List of Primers

| Primer/probe Name | Primer Sequence |
|---|---|
| Ascl1_q_F | 5'-CGACGAGGGATCCTACGAC-3' (SEQ ID NO: 6) |
| Ascl1_q_R | 5'-CTTCCTCTGCCCTCGAAC-3' (SEQ ID NO: 7) |
| Brn2_q_F | 5'-GGTGGAGTTCAAGTCCATCTAC-3' (SEQ ID NO: 8) |
| Brn2_q_R | 5'-TGGCGTCCACGTAGTAGTAG-3' (SEQ ID NO: 9) |
| Myt1L_q_F | 5'-ATACAAGAGCTGTTCAGCTGTC-3' (SEQ ID NO: 10) |
| Myt1L_q_R | 5'-GTCGTGCATATTTGCCACTG-3' (SEQ ID NO: 11) |
| PECAM1_F | 5'-GGACCAGTCCCCGAAGCAGC-3' (SEQ ID NO: 12) |
| PECAM1_R | 5'-AGTGGAGCAGCTGGCCTGGA-3' (SEQ ID NO: 13) |
| VEGFR2_F | 5'-AGCGCTGTGAACGCTTGCCT-3' (SEQ ID NO: 14) |
| VEGFR2_R | 5'-CATGAGAGGCCCTCCCGGCT-3' (SEQ ID NO: 15) |
| EGFP-N | 5'-CCGTCCAGCTCGACCAG-3' (SEQ ID NO: 16) |
| EGFP-C | 5'-GATCACATGGTCCTGCTG-3' (SEQ ID NO: 17) |
| Cdh5_F | 5'-GTGCAACGAGCAGGGCGAGT-3' (SEQ ID NO: 18) |
| Cdh5_R | 5'-GGAGCCACCGCGCACAGAAT-3' (SEQ ID NO: 19) |
| m-K14_F | 5'-GCTGGTGCAGAGCGGCAAGA-3' (SEQ ID NO: 20) |
| m-K14_R | 5'-AGACGGCGGTAGGTGGCGAT-3' (SEQ ID NO: 21) |
| m-Tuj1_F | 5'-TACACGGGCGAGGGCATGGA-3' (SEQ ID NO: 22) |
| m-Tuj1_R | 5'-TCACTTGGGCCCCTGGGCTT-3' (SEQ ID NO: 23) |
| m-Col1A1_F | 5'-GTGTGATGGGATTCCCTGGACCTA-3' (SEQ ID NO: 24) |
| m-Col1A1_R | 5'-CCTGAGCTCCAGCTTCTCCATCTT-3' (SEQ ID NO: 25) |
| m-MAP2_F | 5'-AGGCCAGGTGGTGGACGTGT-3' (SEQ ID NO: 26) |
| m-MAP2_R | 5'-CACGCTGGACCTGCTTGGGG-3' (SEQ ID NO: 27) |
| m-GAPDH_F | 5'-GTGCAGTGCCAGCCTCGTCC-3' (SEQ ID NO: 28) |
| m-GAPDH_R | 5'-GCACCGGCCTCACCCCATTT-3' (SEQ ID NO: 29) |

Immunohistochemistry and Confocal Microscopy

Tissue immunostaining was carried out using specific antibodies and standard procedures. Briefly, OCT-embedded tissue was cryosectioned at 10 μm thick, fixed with cold acetone, blocked with 10% normal goat serum and incubated with specific antibodies. Signal was visualized by subsequent incubation with fluorescence-tagged appropriate secondary antibodies (Alexa 488-tagged a-guinea pig, 1:200, Alexa 488-tagged a-rabbit, 1:200; Alexa 568-tagged a-rabbit, 1:200) and counter stained with DAPI. Images were captured by laser scanning confocal microscope (Olympus FV 1000 filter/spectral).

IVIS Imaging

The animals were imaged with anesthesia 24 h after FAM-DNA transfection using IVIS Lumina II optical imaging system. Overlay images with luminescence images were made using Living Image software.

Magnetic Resonance Imaging (MRI) of Stroked Brains

Magnetic resonance angiography was used to validate our MCAO model in mice and to optimize the occluder size and the internal carotid artery insertion distance for effective MCAO. T2-weighted MRI was performed on anesthetized mice 48 h after MCA-reperfusion using 9.4 T MRI (Bruker Corporation, Bruker BioSpin Corporation, Billerica, MA, USA). MR images were acquired using a Rapid Acquisition with Relaxation Enhancement (RARE) sequence using the following parameters: field of view (FOV) 30×30 mm, acquisition matrix 256×256, TR 3,500 ms, TE 46.92 ms, slice gap 1.0 mm, rare factor 8, number of averages 3. Resolution of 8.5 pixels per mm. Raw MR images were converted to the standard DICOM format and processed. After appropriate software contrast enhancement of images using Osirix v3.4, digital planimetry was performed by a masked observer to delineate the infarct area in each coronal brain slice. Infarct areas from brain slices were summed, multiplied by slice thickness, and corrected for edema-induced swelling as previously described to determine infarct volume (Khanna S, et al. J Cereb Blood Flow Metab 2013, 33(8):1197-1206).

Analysis of Muscle Energetics

Muscle energetics was evaluated NMR spectroscopy measurements on a 9.4 Tesla scanner (Bruker BioSpec)

using a volume coil for RF transmission and a 31P coil for reception (Fiedler et al. MAGMA 2015, 28(5): 493-501.). In vivo imaging was conducted in a custom-made 1H/31P transceiver coil array. Data were acquired using single pulse sequence. The raw data were windowed for noise reduction and Fourier transformed to spectral domain.

Ultrasound-Based Imaging and Characterization of Blood Vessels

Blood vessel formation was parallely monitored via ultrasound imaging. Briefly, a Vevo 2100 system (Visual Sonics, Toronto, ON, Canada) was used to obtain ultrasound images on B-mode with a MS 250 linear array probe (Gnyawali et al. J Vis Exp 2010(41). Doppler color flow imaging was implemented to monitor and quantify blood flow characteristics under systole and diastole.

Statistical Analysis

Samples were coded and data analysis was performed in a blinded fashion. For animal studies, data are reported as mean±SD of 3 animals (i.e., biological replicates). No animals were excluded from the analysis. Likewise, in vitro reprogramming data are reported as mean±SD of at least 3 experiments. Experiments were replicated at least twice to confirm reproducibility. Comparisons between groups were made by analysis of variance (ANOVA). Statistical differences were determined via parametric/non-parametric tests as appropriate with SigmaPlot version 13.0.

The disclosed results using TNT-based approach are indicative of what can be accomplished using nanochannel-based delivery, including the microstructure array disclosed herein.

Example 2

In a particular embodiment, arrayed interpenetrating nanochannels can be fabricated from silicon-based materials using cleanroom methods such as photolithography and wet or dry etching. First, an array of conical or pyramidal interpenetrating microstructures (approximately 20-500 microns tall) is defined on a silicon surface using photolithography and wet or dry etching. Subsequently, the silicon substrate is patterned on the backside with an array of nanowells (approximately 300-1000 nm diameter) using projection lithography. Next a highly anisotropic deep reactive ion etch (DRIE) to drill nanochannels through the silicon substrate and the interpenetrating microstructures.

The following is an example method for fabrication of nanochanneled microneedle arrays on silicon (1) Fabrication of 3D Nanochannel Array 1. Select 4 inch silicon wafer: 500 µm, DSP, Prime grade.
2. Thin the wafer to 250 µm thick by wet etching (KOH, 45%, 80 Degree C.)
3. Pattern AZ-5214 nano-circle array (400 nm in diameter, spacing: 25 µm) using Stepper (NTW).
4. DRIE Etch the silicon wafer masked by AZ-5214 pattern.
   System: Oxford Plasma Lab 100 in Dreese Lab
   Recipe Name: Lingqian_Bosch
   SF6 Protocol: 100 sccm/13 s/ICP 700 W/RF 30 W/Chamber Pressure 30 mT (double check)
   C4F8 Protocol: 100 sccm/7 s/ICP 700 W/RF 10 W/Chamber Pressure 30 mT (double check)
   Etching Procedure: Running 40 cycles; Stop 5 minutes; Running another 5 cycles; Stop 5 minutes and check if there is still photoresist remained. If yes, run another 5 cycles. Check again. Usually, the PR are totally gone with 55-60 cycles. (Please be aware, don't directly run 60 cycles instead of 40+5+5+5+5. Otherwise, the PR will be burned after 60 cycles)
5. Clean the silicon wafer/AZ5214 completely using TMP; Clean the wafer in Piranha solution for 5 minutes (120 Degree C.). Check if the nanochannel array is visible using Olympus Microscope in Bay 1 (NTW)
6. Standard Photolithography procedure for pattern microchannel array (50 µm in diameter; Center to Center distance: 70 µm) on the other side of the silicon wafer. Photoresist: SPR 220-7; Thickness: 10 µm. In the patterning procedure: Make sure the array of microchannel is generally with same direction to the nanochannel array.
7. Prepare another silicon wafer with 250 µm in thickness.
8. Fully coat the pump oil (used for ETC04 in Bay 4, NTW) on the side of the nanochannel. Key: oil all over the surface of the silicon wafer rather than a droplet. Otherwise, the area without oil will cook the SPR 220 PR in DRIE procedure.
9. Carefully and fully bond the 250 µm thick silicon wafer with nanochannel side, interfaced with oil. This way is to reduce the heat in long time DRIE system while keep silicon wafer rigid enough to the helium force in DRIE procedure.
10. DRIE Etch the silicon wafer masked by SPR 220-7.
    System: Oxford Plasma Lab 100 in Dreese Lab
    Recipe Name: Lingqian_Bosch
    SF6 Protocol: 100 sccm/13 s/ICP 700 W/RF 30 W/Chamber Pressure 30 mT (double check)
    C4F8 Protocol: 100 sccm/7 s/ICP 700 W/RF 10 W/Chamber Pressure 30 mT (double check)
    Etching Procedure: Running 250 cycles; Stop 5 minutes; Running another 20 cycles; Stop 5 minutes and check if there is still photoresist remained. If yes, run another 10 cycles. Check again. In experience, microchannel will connect nanochannel after about 280 cycles. However, the precise cycle is impossible to fix as the Oxford Plasma system is always drifting. Therefore, after 270 cycles, SEM should be used to check the cross-section of microchannel in any stop time, to evaluate that if all microchannel has connected with nanochannel (This part is the mostly time consuming, which need about 3-5 days, depending on availability)
11. Slowly and carefully remove the sample from
12. Clean the wafer in Piranha solution for 5 minutes (120 Degree C.). Check if the nanochannel array and microchannel array using Olympus Microscope in Bay 1 (NTW)
13. Depends on the design of nanochannel, the silicon wafer was diced into small pieces.

(2) Fabrication of Microneedles Using DRIE

1. Pick up one silicon sample with the dimension of 1 cm×1 cm and thoroughly clean the sample with piranha solution.
2. Pattern micro-circle array on the nanochannel side: SPR 220-7 photoresist, 10 µm in thickness. Micro-circle pattern: 15 µm in diameter, which finally determined the dimension of the volcano-shaped needle. Spacing: center-center 25 µm. Ideal Condition: align micro-circle with nanochannel array in photolithography, which can increase the hollow needle percentage.
3. Stick small sample on a fresh 4 inch wafer with oil (full-area coated with oil)
4. DRIE Procedure: Oxford Plasma Lab 100
   Recipe: Lingqian_Isotropic Etch (double check)
   Protocol: SF6: 40 sccm/ICP power: 600 W/RF power 5 W-10 W (which determine the shape of the volcano).
   Etching time: 2 mins; stop and check if there are PR remained; IF yes, 1 more minutes and check if PR is remained; If Yes, one more minutes. If gone, check the microscope or SEM. If needle is not shown, continue etching 1 minute without mask.

5. Under the optimized protocol above, the micro-needle will be fabricated with ~2+1+1 minutes.

Example 3

In one particular embodiment, arrayed interpenetrating nanochannels can be fabricated from a premade nanochanneled substrate platform that can either be silicon-based or made from anodized alumina via selective surface etching. Selective surface etching is used to define interpenetrating microstructures Example 4

In a preferred embodiment, a method delivering cargo to biological tissues at multiple levels is performed using an interpenetrating nanochannel array. The interpenetrating nanochannel array is placed in contact with exfoliated skin tissue. A positive electrode is inserted intradermally, while a negative electrode is put in contact with the cargo solution. A pulsed electric field (250 V, 10 ms pulses, 10 pulses) is then applied across the electrodes to nanoporate exposed cell membranes and inject the cargo directly into the cytosol.

The cargo solution comprised a mixture of three plasmids, encoding for Etv2, Foxc2 and F11. Small tissue biopsies were collected 24 h after delivery and analyzed by qRT-PCR. Additional biopsies were collected 7 days post-delivery and analyzed via immunohistochemistry for endothelial markers. DTN-based delivery results in superior transgene expression as well as widely distributed reprogramming responses across the entire tissue thickness Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

Rosova I, Dao M, Capoccia B, Link D, Nolta J A. Hypoxic preconditioning results in increased motility and improved therapeutic potential of human mesenchymal stem cells. Stem Cells 2008, 26(8): 2173-2182.

Kinoshita M, Fujita Y, Katayama M, Baba R, Shibakawa M, Yoshikawa K, et al. Long-term clinical outcome after intramuscular transplantation of granulocyte colony stimulating factor-mobilized CD34 positive cells in patients with critical limb ischemia. Atherosclerosis 2012, 224(2): 440-445.

Losordo D W, Dimmeler S. Therapeutic angiogenesis and vasculogenesis for ischemic disease: part II: cell-based therapies. Circulation 2004, 109(22): 2692-2697.

Lee A S, Tang C, Rao M S, Weissman I L, Wu J C. Tumorigenicity as a clinical hurdle for pluripotent stem cell therapies. Nat Med 2013, 19(8): 998-1004.

Cunningham J J, Ulbright T M, Pera M F, Looijenga L H. Lessons from human teratomas to guide development of safe stem cell therapies. Nat Biotechnol 2012, 30(9):849-857.

Leduc P R, Wong M S, Ferreira P M, Groff R E, Haslinger K, Koonce M P, et al. Towards an in vivo biologically inspired nanofactory. Nat Nanotechnol 2007, 2(1): 3-7.

Heinrich C, Spagnoli F M, Beminger B. In vivo reprogramming for tissue repair. Nat Cell Biol 2015, 17(3): 204-211.

Karagiannis P, Yamanaka S. The fate of cell reprogramming. Nat Methods 2014, 11(10): 1006-1008.

Grande A, Sumiyoshi K, Lopez-Juarez A, Howard J, Sakthivel B, Aronow B, et al. Environmental impact on direct neuronal reprogramming in vivo in the adult brain. Nat Commun 2013, 4: 2373.

Morita R, Suzuki M, Kasahara H, Shimizu N, Shichita T, Sekiya T, et al. ETS transcription factor ETV2 directly converts human fibroblasts into functional endothelial cells. Proc Natl Acad Sci USA 2015, 112(1): 160-165.

Gallego-Perez D, Otero J J, Czeisler C, Ma J, Ortiz C, Gygli P, et al. Deterministic transfection drives efficient nonviral reprogramming and uncovers reprogramming barriers. Nanomedicine 2015.

Marx V. Cell biology: delivering tough cargo into cells. Nat Meth 2016, 13(1): 37-40. Boukany P E, Morss A, Liao W C, Henslee B, Jung H, Zhang X, et al. Nanochannel electroporation delivers precise amounts of biomolecules into living cells. Nat Nanotechnol 2011, 6(11): 747-754.

Sen C K, Ghatak S. miRNA control of tissue repair and regeneration. Am J Pathol 2015, 185(10): 2629-2640.

Vierbuchen T, Ostermeier A, Pang Z P, Kokubu Y, Sudhof T C, Wernig M. Direct conversion of fibroblasts to functional neurons by defined factors. Nature 2010, 463 (7284): 1035-1041.

Valadi H, Ekstrom K, Bossios A, Sjostrand M, Lee J J, Lotvall J O. Exosome-mediated transfer of mRNAs and microRNAs is a novel mechanism of genetic exchange between cells. Nat Cell Biol 2007, 9(6): 654-659.

Khanna S, Rink C, Ghoorkhanian R, Gnyawali S, Heigel M, Wijesinghe D S, et al. Loss of miR-29b following acute ischemic stroke contributes to neural cell death and infarct size. J Cereb Blood Flow Metab 2013, 33(8): 1197-1206.

Hunt D P, Morris P N, Sterling J, Anderson J A, Joannides A, Jahoda C, et al. A highly enriched niche of precursor cells with neuronal and glial potential within the hair follicle dermal papilla of adult skin. Stem Cells 2008, 26(1): 163-172.

Higgins C A, Itoh M, Inoue K, Richardson G D, Jahoda C A, Christiano A M. Reprogramming of human hair follicle dermal papilla cells into induced pluripotent stem cells. J Invest Dermatol 2012, 132(6): 1725-1727.

Helisch A, Wagner S, Khan N, Drinane M, Wolfram S, Heil M, et al. Impact of mouse strain differences in innate hindlimb collateral vasculature. Arterioscler Thromb Vasc Biol 2006, 26(3): 520-526.

Chalothorn D, Clayton J A, Zhang H, Pomp D, Faber J E. Collateral density, remodeling, and VEGF-A expression differ widely between mouse strains. Physiol Genomics 2007, 30(2): 179-191.

Limbourg A, Korff T, Napp L C, Schaper W, Drexler H, Limbourg F P. Evaluation of postnatal arteriogenesis and angiogenesis in a mouse model of hind-limb ischemia. Nat Protoc 2009, 4(12): 1737-1746.

Fiedler G B, Meyerspeer M, Schmid A I, Goluch S, Schewzow K, Laistler E, et al. Localized semi-LASER dynamic (31)P magnetic resonance spectroscopy of the soleus during and following exercise at 7 T. MAGMA 2015, 28(5): 493-501.

Gnyawali S C, Roy S, Driggs J, Khanna S, Ryan T, Sen C K. High-frequency high-resolution echocardiography: first evidence on non-invasive repeated measure of myocardial strain, contractility, and mitral regurgitation in the ischemia-reperfused murine heart. J Vis Exp 2010(41).

Geng, T. & Lu, C. Lab Chip 13, 3803-3821 (2013).

Boukany, P. E. et al. Nat Nanotechnol 6, 747-754 (2011).

Morita, R. et al. Proc Natl Acad Sci USA 112, 160-165 (2015).

De Val, S. & Black, B. L. Dev Cell 16, 180-195 (2009).

What is claimed is:

1. A method for obtaining a sample from cells within a tissue, the method comprising:
   a) providing a microstructure array that comprises:
      a planar substrate having a top surface and a bottom surface;
      a reservoir in fluid communication with the top surface of the planar substrate; and
      a plurality of microstructures projecting from the bottom surface of the planar substrate, each of the plurality of microstructures comprising:
         a solid body portion tapering from a base to a distal tip positioned at a height from the bottom surface of the planar substrate, thereby defining a microstructure surface;
         a first sampling channel or slit extending from the top surface of the planar substrate to a first channel opening or slit within the microstructure surface, thereby fluidly connecting the reservoir to the first channel opening or slit; and
         a second sampling channel or slit extending from the top surface of the planar substrate to a second channel opening or slit within the microstructure surface, thereby fluidly connecting the reservoir to the second channel opening or slit; and
      a first electrode in electrical contact with the reservoir and a second electrode configured to electrically contact a tissue positioned against the bottom surface of the planar substrate,
      wherein the solid body portion of each of the plurality of microstructures is formed from silicon using photolithography and etching,
      wherein the first sampling channel or slit and second sampling channel or slit have an inner diameter of 1 to 999 nm,
      wherein the first channel opening or slit of each of the plurality of microstructures is positioned within a first plane parallel to the planar substrate, wherein the second channel opening or slit of each of the plurality of microstructures is positioned within a second plane parallel to the planar substrate, and wherein the first plane is distally spaced apart from the second plane,
      wherein the first plane is distally spaced apart from the second plane by a distance of from 20% to 60% of the height from the bottom surface of the planar substrate, and
      wherein the first channel opening or slit is positioned at the distal tip of each of the plurality of microstructures;
   b) applying the microstructure array to the tissue, wherein the bottom surface of the planar substrate is positioned against the tissue and the plurality of microstructures extend into the tissue; and
   c) sampling a substance from the cells within a tissue through the first sampling channel and the second sampling channel of each of the plurality of microstructures to the reservoir by applying an electric field through the first electrode and second electrode.

2. The method of claim 1, wherein the each of the plurality of microstructures further comprises a third sampling channel extending from the top surface of the planar substrate to a third channel opening or slit within the microstructure surface, thereby fluidly connecting the reservoir to the third channel opening or slit.

3. The method of claim 2, wherein the first channel opening or slit is positioned within a first plane parallel to the planar substrate, wherein the second channel opening or slit is positioned within a second plane parallel to the planar substrate, wherein the third channel opening or slit is positioned within a third plane parallel to the planar substrate;

and wherein the first plane is distally spaced apart from the second plane and the second plane is distally spaced apart from the third plane.

4. The method of claim 1, wherein the height of the microstructure surface is from 5 microns to 1000 microns, and wherein the width of the base of the microstructure is from 5 microns to 500 microns.

5. The method of claim 1, wherein the base of the microstructure has a substantially circular shape or rectangular shape.

6. The method of claim 1, wherein the plurality of microstructures comprise parallel ridges, ridges arrayed in a herringbone pattern, ridges arrayed in a waveform pattern, cones, or pyramids.

7. The method of claim 1, wherein the distal tip of the microstructure is pointed, rounded, slanted, flared, tapered, blunted or combinations thereof.

8. The method of claim 1, wherein the first sampling channel and the second sampling channel each have a substantially circular or rectangular cross-section in a plane parallel to the planar substrate.

9. The method of claim 1, wherein the first sampling channel and the second sampling channel each have a substantially toroidal cross-section in a plane parallel to the planar substrate; and
wherein the second sampling channel is coaxially disposed around the first sampling channel.

10. The method of claim 1, wherein the first sampling channel has a substantially circular cross-section in a plane parallel to the planar substrate and the second sampling channel has a substantially toroidal cross-section in a plane parallel to the planar substrate; and
wherein the second sampling channel is coaxially disposed around the first sampling channel.

11. The microstructure array of claim 1, wherein each of the plurality of microstructures comprises a solid body portion tapering in a stepwise fashion from the base to the distal tip.

12. The method of claim 1, wherein each of the plurality of microstructures comprises a solid body portion having a frustoconical shape.

13. The method of claim 1, wherein the planar substrate further comprises a plurality of sampling channels, each of which extends from the top surface of the planar substrate to a channel opening within the bottom surface of the planar substrate, thereby fluidly connecting the reservoir to the channel opening within the bottom surface of the planar substrate.

14. The method of claim 1, wherein the substance is simultaneously sampled from multiple cell levels of the tissue.

15. The method of claim 1, wherein the electric field is applied at a potential of from 1 V to 500 V.

16. The method of claim 15, wherein the electric field comprises a pulsed electric field.

17. The method of claim 16, wherein the pulsed electric field comprises a plurality of pulses having a duration of from 0.1 millisecond to 100 milliseconds.

18. The method of claim 17, wherein the pulsed electric field comprises from 1 to 500 pulses.

19. The method of claim 1, wherein the substance comprises an extracellular material.

20. The method of claim 19, wherein the extracellular material comprises interstitial fluid.

21. The method of claim 19, wherein the extracellular material comprises intracellular material.

* * * * *